United States Patent
Takebe et al.

(10) Patent No.: US 11,603,520 B2
(45) Date of Patent: Mar. 14, 2023

(54) METHOD FOR INTEGRATING BIOLOGICAL TISSUES WITH A VASCULAR SYSTEM

(71) Applicant: Public University Corporation Yokohama City University, Yokohama (JP)

(72) Inventors: Takanori Takebe, Yokohama (JP); Hideki Taniguchi, Yokohama (JP); Yoshinobu Takahashi, Yokohama (JP)

(73) Assignee: Public University Corporation Yokohama City University, Yokohama (JP)

( * ) Notice: Subject to any disclaimer, the term of this patent is extended or adjusted under 35 U.S.C. 154(b) by 0 days.

(21) Appl. No.: 17/345,825

(22) Filed: Jun. 11, 2021

(65) Prior Publication Data

US 2022/0167597 A1    Jun. 2, 2022

Related U.S. Application Data

(63) Continuation of application No. 14/906,699, filed as application No. PCT/JP2014/068808 on Jul. 15, 2014.

(30) Foreign Application Priority Data

Jul. 23, 2013 (JP) ................. 2013-153056

(51) Int. Cl.
| | |
|---|---|
| A01K 67/027 | (2006.01) |
| C12N 5/00 | (2006.01) |
| C12N 5/071 | (2010.01) |
| G01N 33/50 | (2006.01) |
| C07D 499/21 | (2006.01) |
| A61L 27/38 | (2006.01) |
| A61K 35/28 | (2015.01) |
| A61K 35/44 | (2015.01) |
| A61K 49/00 | (2006.01) |

(52) U.S. Cl.
CPC ........ *C12N 5/0691* (2013.01); *A01K 67/0271* (2013.01); *A61K 35/28* (2013.01); *A61K 35/44* (2013.01); *A61K 49/0008* (2013.01); *A61L 27/3808* (2013.01); *A61L 27/3834* (2013.01); *A61L 27/3886* (2013.01); *C07D 499/21* (2013.01); *C12N 5/0062* (2013.01); *C12N 5/0677* (2013.01); *G01N 33/5082* (2013.01); *A01K 2207/12* (2013.01); *A01K 2227/105* (2013.01); *A01K 2267/035* (2013.01); *A01K 2267/0325* (2013.01); *A01K 2267/0331* (2013.01); *A01K 2267/0362* (2013.01); *C12N 2502/13* (2013.01); *C12N 2506/1346* (2013.01); *C12N 2506/28* (2013.01); *C12N 2513/00* (2013.01)

(58) Field of Classification Search
None
See application file for complete search history.

(56) References Cited

U.S. PATENT DOCUMENTS 7,029,838 B2 * 4/2006 Williams ............. C12N 5/0691
                                              424/93.1

FOREIGN PATENT DOCUMENTS

WO    WO-2013047639 A1 * 4/2013 ............. A61K 35/28

OTHER PUBLICATIONS

Jung, et al. (2011) "Bone marrow-derived mesenchymal stromal cells support rat pancreatic islet survival and insulin secretory function in vitro", Cytotherapy, 13(1): 19-29. (Year: 2011).*

(Continued)

*Primary Examiner* — Robert M Kelly
(74) *Attorney, Agent, or Firm* — Morgan, Lewis & Bockius LLP

(57) ABSTRACT

The present invention provides a method of constituting a tissue construct in vitro using a tissue without depending on scaffold materials.

A method of integrating a biological tissue with a vascular system in vitro, comprising coculturing a biological tissue with vascular cells and mesenchymal cells. A biological tissue which has been integrated with a vascular system by the above-described method. A method of preparing a tissue or an organ, comprising transplanting the biological tissue described above into a non-human animal and differentiating the biological tissue into a tissue or an organ in which vascular networks have been constructed. A method of regeneration or function recovery of a tissue or an organ, comprising transplanting the biological tissue described above into a human or a non-human animal and differentiating the biological tissue into a tissue or an organ in which vascular networks have been constructed. A method of preparing a non-human chimeric animal, comprising transplanting the biological tissue described above into a non-human animal and differentiating the biological tissue into a tissue or organ in which vascular networks have been constructed. A method of evaluating a drug, comprising using at least one member selected from the group consisting of the biological tissue described above, the tissue or organ prepared by the method described above, and the non-human chimeric animal prepared by the method described above. A composition for regenerative medicine, comprising a biological tissue which has been integrated with a vascular system by the method described above.

12 Claims, 30 Drawing Sheets

(56) References Cited

OTHER PUBLICATIONS

Johansson, et al. (2008) "Formation of Composite Endotheilal Cell-Mesenchymal Stem Cell Islets", Diabetes, 57: 2393-401. (Year: 2008).*

Lee, et al. (2005) "The Effect of Pancreatic Islet Transplantation on Progression of Diabetic Retinopathy and Neuropathy", Transplantation Proceedings, 37: 2263-2265. (Year: 2005).*

* cited by examiner

Scale bar: 200 μm

Fig. 1J

| Gene | Genes with increased expression by co-culture (more than double) | GeneSymbol | GenbankAccession |
|---|---|---|---|
| angiopoietin 2 | 86404010298 | ANGPT2 | NM_001147 |
| chemokine (C-C motif) ligand 14 | 12485228642 | CCL14 | NM_032963 |
| von Willebrand factor | 9723989921 | VWF | NM_000552 |
| spondin 2, extracellular matrix protein | 5173085781 | SPON2 | AK124606///NM_012445 |
| interleukin 1 receptor-like 1 | 2871116401 | IL1RL1 | AB029084///NM_016232 |
| insulin-like growth factor binding protein 3 | 1732005234 | IGFBP3 | NM_001013398 |
| platelet/endothelial cell adhesion molecule | 1200911766 | PECAM1 | NM_000442 |
| MFNG O-fucosylpeptide 3-beta-N-acetylglucosaminyltransferase | 737585210.5 | MFNG | NM_002405 |
| decorin | 62323314.06 | DCN | NM_133507 |
| desert hedgehog | 44521819.03 | DHH | NM_021044 |
| thrombomodulin | 13577375.84 | THBD | NM_000361 |
| jagged 2 | 9178351.802 | JAG2 | NM_002226 |
| apelin | 9075195.72 | APLN | NM_017413 |
| aggrecan | 6258112.989 | ACAN | NM_013227///NM_001135 |
| retinol binding protein 4, plasma | 5501722.736 | RBP4 | NM_006744 |
| collagen, type VI, alpha 3 | 5342235.144 | COL6A3 | NM_004369 |
| interleukin 33 | 4920010.165 | IL33 | NM_033439 |
| receptor (G protein-coupled) activity modifying protein 1 | 4884056.732 | RAMP1 | NM_005855 |
| tumor necrosis factor (ligand) superfamily, member 10 | 4362487.545 | TNFSF10 | NM_003810 |
| interleukin 11 | 3248955.777 | IL11 | NM_000641 |
| matrix Gla protein | 3002928.557 | MGP | NM_001190839///NM_000900 |
| endothelin 1 | 2616534.708 | EDN1 | NM_001955 |
| collagen, type III, alpha 1 | 2391112.666 | COL3A1 | NM_000090 |
| pro-melanin-concentrating hormone | 2339702.828 | PMCH | NM_002674 |
| ephrin-A1 | 2101511.157 | EFNA1 | NM_004428 |
| glypican 5 | 569311.688 | GPC5 | NM_004466 |
| chemokine (C-X-C motif) ligand 11 | 509934.3879 | CXCL11 | NM_005409 |
| collagen, type VI, alpha 2 | 408334.8057 | COL6A2 | NM_058174///NM_058175 |
| contactin associated protein-like 4 | 319100.5847 | CNTNAP4 | NM_033401///NM_138994 |
| chitinase 3-like 1 (cartilage glycoprotein-39) | 281018.1044 | CHI3L1 | NM_001276 |

Fig. 1 J (CONTINUED)

| | | | |
|---|---|---|---|
| wingless-type MMTV integration site family, member 5A | 263620.0876 | WNT5A | NM_003392 |
| selectin P (granule membrane protein 140kDa, antigen CD62) | 216688.0693 | SELP | NM_003005 |
| stimulator of chondrogenesis 1 | 185152.0394 | SCRG1 | NM_007281 |
| protease, serine, 2 (trypsin 2) | 128606.6424 | PRSS2 | NM_002770 |
| CD40 molecule, TNF receptor superfamily member 5 | 127056.3281 | CD40 | NM_001250 |
| matrix metallopeptidase 7 (matrilysin, uterine) | 97987.22531 | MMP7 | NM_002423 |
| placental growth factor | 72232.24283 | PGF | NM_002632///AK023843 |
| lymphotoxin beta (TNF superfamily, member 3) | 68001.8926 | LTB | NM_002341 |
| gremlin 2 | 65322.89144 | GREM2 | NM_022469 |
| slit homolog 3 (Drosophila) | 62653.46582 | SLIT3 | NM_003062 |
| chemokine (C-C motif) ligand 23 | 54595.494 | CCL23 | NM_005064 |
| periostin, osteoblast specific factor | 50697.9268 | POSTN | NM_006475 |
| glia maturation factor, gamma | 49956.96545 | GMFG | NM_004877 |
| bone morphogenetic protein 6 | 47659.98363 | BMP6 | NM_001718 |
| fibroblast growth factor 16 | 46350.68961 | FGF16 | NM_003868 |
| EGF-like-domain, multiple 7 | 41728.96374 | EGFL7 | NM_201446 |
| vasohibin 1 | 35824.32614 | VASH1 | NM_014909 |
| colony stimulating factor 3 (granulocyte) | 35820.32319 | CSF3 | NM_000759 |
| fibroblast growth factor 1 (acidic) | 16579.67068 | FGF1 | NR_026696 ///NM_000800 |
| bone morphogenetic protein 4 | 14963.88993 | BMP4 | NM_001202 |
| interleukin 1, beta | 10718.08014 | IL1B | NM_000576 |
| interleukin 8 | 8641.750034 | IL8 | NM_000584 |
| cholesteryl ester transfer protein, plasma | 7269.850836 | CETP | NM_000078 |
| gremlin 1 | 6841.392387 | GREM1 | NM_013372 |
| complement factor I | 6413.055523 | CFI | NM_000204 |
| v-kit Hardy-Zuckerman 4 feline sarcoma viral oncogene homolog | 6212.681649 | KIT | NM_001093772/// NM_000222 |
| endothelial cell-specific molecule 1 | 5393.69395 | ESM1 | NM_007036 |
| leukemia inhibitory factor (cholinergic differentiation factor) | 4950.039677 | LIF | NM_002309 |
| tubulin, alpha 8 | 3636.752952 | TUBA8 | NM_018943 |
| cysteine-rich secretory protein LCCL domain containing 2 | 3117.885771 | CRISPLD2 | NM_031476 |

Fig. 1J (CONTINUED)

| | | | |
|---|---|---|---|
| epithelial mitogen homolog (mouse) | 3080.182152 | EPGN | NM_001013442 |
| alpha-2-macroglobulin | 2091.158733 | A2M | NM_000014 |
| chemokine (C-X-C motif) ligand 2 | 2041.672598 | CXCL2 | NM_002089 |
| family with sequence similarity 3, member D | 1982.131667 | FAM3D | NM_138805 |
| WNT1 inducible signaling pathway protein 3 | 1893.120682 | WISP3 | NM_198239 |
| bone morphogenetic protein 3 | 1775.228248 | BMP3 | NM_001201 |
| insulin-like growth factor binding protein 6 | 1705.390738 | IGFBP6 | NM_002178 |
| laminin, alpha 4 | 1701.743498 | LAMA4 | NM_001105206 ///NM_001105209 ///NM_001105207 |
| RAB3D, member RAS oncogene family | 1695.062164 | RAB3D | NM_004283 |
| sema domain, immunoglobulin domain (Ig), short basic domain, secreted, (semaphorin) 3C | 1663.817163 | SEMA3C | NM_006379 |
| dedicator of cytokinesis 4 | 1642.331414 | DOCK4 | NM_014705 |
| selectin E | 1307.998473 | SELE | NM_000450 |
| solute carrier family 6 (neurotransmitter transporter, dopamine), member 3 | 1192.381145 | SLC6A3 | NM_001044 |
| threonine synthase-like 2 (S. cerevisiae) | 1098.132133 | THNSL2 | NM_018271 ///HM185274 |
| nerve growth factor (beta polypeptide) | 1079.932805 | NGF | NM_002506 |
| proprotein convertase subtilisin/kexin type 1 | 994.7088227 | PCSK1 | NM_000439 |
| microseminoprotein, beta- | 878.5637296 | MSMB | NM_002443 |
| cytokine-like 1 | 863.3098578 | CYTL1 | NM_018659 |
| interleukin 22 receptor, alpha 2 | 747.6728319 | IL22RA2 | NM_181310 ///NM_052962 |
| tissue factor pathway inhibitor (lipoprotein-associated coagulation inhibitor) | 613.9723312 | TFPI | NM_001032281 |
| tumor necrosis factor (ligand) superfamily, member 18 | 437.1089511 | TNFSF18 | NM_005092 |
| urocortin 2 | 415.0944245 | UCN2 | NM_033199 |
| progastricsin (pepsinogen C) | 403.8345759 | PGC | NM_001166424 ///NM_002630 |
| neuregulin 3 | 336.9189511 | NRG3 | NM_001010848 |
| chemokine (C-C motif) ligand 25 | 312.2950065 | CCL25 | NM_005624 |
| sushi-repeat containing protein, X-linked 2 | 303.6426689 | SRPX2 | NM_014467 |
| ADAM metallopeptidase with thrombospondin type 1 motif, 4 | 303.5576625 | ADAMTS4 | BC030812 |

Fig. 1J (CONTINUED)

| Description | Value | Symbol | Accession |
|---|---|---|---|
| selectin P ligand | 293.1140863 | SELPLG | NM_001206609 |
| lysyl oxidase | 272.618485 | LOX | NM_002317 |
| fibroblast growth factor 5 | 259.9950921 | FGF5 | NM_004464 ///NM_033143 |
| chemokine (C-C motif) ligand 16 | 238.9045109 | CCL16 | NM_004590 |
| dedicator of cytokinesis 5 | 221.0027104 | DOCK5 | NM_024940 |
| apolipoprotein D | 185.1239891 | APOD | NM_001647 |
| dedicator of cytokinesis 9 | 142.42849 | DOCK9 | NM_001130048 ///AK090793 |
| interleukin 15 receptor, alpha | 111.072268 | IL15RA | NM_002189 ///NM_172200 |
| elastin microfibril interfacer 1 | 100.1885866 | EMILIN1 | NM_007046 |
| c-fos induced growth factor (vascular endothelial growth factor D) | 95.29124914 | FIGF | NM_004469 |
| follistatin-like 3 (secreted glycoprotein) | 88.64529712 | FSTL3 | NM_005860 |
| interleukin 17B | 84.81534637 | IL17B | NM_014443 |
| serpin peptidase inhibitor, clade B (ovalbumin), member 2 | 79.84232039 | SERPINB2 | NM_002575 |
| purinergic receptor P2X, ligand-gated ion channel, 7 | 74.58845991 | P2RX7 | NM_002562 |
| neuregulin 2 | 71.43796095 | NRG2 | NM_013982 |
| chemokine (C-C motif) ligand 4 | 70.57004592 | CCL4 | NM_002984 |
| interleukin 1, alpha | 70.32970569 | IL1A | NM_000575 |
| insulin-like growth factor binding protein 1 | 70.02643222 | IGFBP1 | NM_000596 |
| CD97 molecule | 60.1517449 | CD97 | NM_078481 |
| chemokine (C-C motif) receptor 3 | 58.8548287 | CCR3 | NM_001837 |
| brevican | 58.37805213 | BCAN | NM_198427 |
| dedicator of cytokinesis 6 | 55.97183175 | DOCK6 | NM_020812 |
| C-type lectin domain family 3, member B | 55.52562299 | CLEC3B | NM_003278 |
| interleukin 21 | 53.40043564 | IL21 | NM_021803 |
| sema domain, immunoglobulin domain (Ig), short basic domain, secreted, (semaphorin) 3F | 47.83718329 | SEMA3F | NM_004186 |
| metastasis suppressor 1 | 45.71291541 | MTSS1 | NM_014751 |
| coagulation factor XII (Hageman factor) | 45.13469375 | F12 | NM_000505 |
| interleukin 18 binding protein | 44.57019149 | IL18BP | NM_173042 |
| laminin, alpha 2 | 41.06181103 | LAMA2 | NM_000426 |
| mutS homolog 5 (E. coli) | 41.03878268 | MSH5 | NM_002441 ///NM_025259 |
| chemokine (C-C motif) ligand 3-like 3 | 39.8024495 | CCL3L3 | NM_001001437 |
| prostaglandin D2 synthase 21kDa (brain) | 38.61488626 | PTGDS | CR610092///NM_000954 |

Fig. 1J (CONTINUED)

| | | | |
|---|---|---|---|
| interleukin 6 receptor | 36.36562031 | IL6R | NM_000565 |
| CKLF-like MARVEL transmembrane domain containing 1 | 30.52049198 | CMTM1 | NM_052999 |
| nephroblastoma overexpressed gene | 30.24866415 | NOV | NM_002514 |
| R-spondin 3 | 28.01382427 | RSPO3 | NM_032784 |
| gastrokine 1 | 25.73552072 | GKN1 | NM_019617 |
| wingless-type MMTV integration site family, member 4 | 25.56496485 | WNT4 | NM_030761 |
| angiotensinogen (serpin peptidase inhibitor, clade A, member 8) | 23.35608784 | AGT | NM_000029 |
| advanced glycosylation end product-specific receptor | 22.24914723 | AGER | NM_001206954 ///NM_001206966 |
| dedicator of cytokinesis 2 | 22.01202412 | DOCK2 | NM_004946 |
| keratinocyte growth factor-like protein 1 | 21.06057189 | KGFLP1 | NR_003674 |
| neuron-derived neurotrophic factor | 15.36653325 | NDNF | NM_024574 |
| ovostatin 2 | 15.28938793 | OVOS2 | AL831947 ///XM_003120218 |
| angiopoietin-like 4 | 15.25681921 | ANGPTL4 | NM_139314 |
| UL16 binding protein 2 | 15.12748044 | ULBP2 | NM_025217 |
| epidermal growth factor receptor | 14.03965384 | EGFR | NM_201282 ///NM_201283 ///NM_005228 |
| solute carrier family 9 (sodium/hydrogen exchanger), member 3 regulator 2 | 13.68148347 | SLC9A3R2 | NM_004785 |
| proteinase 3 | 12.64903517 | PRTN3 | NM_002777 |
| inhibin, beta B | 12.03648281 | INHBB | NM_002193 |
| ADAMTS-like 4 | 11.13213335 | ADAMTSL4 | NM_025008 ///NM_019032 |
| inhibin, beta A | 9.449823565 | INHBA | NM_002192 |
| tubulin, alpha 3c | 8.918192656 | TUBA3C | NM_006001 |
| matrix metallopeptidase 21 | 8.866300776 | MMP21 | NM_147191 |
| nucleoporin 43kDa | 8.257302406 | NUP43 | NM_198887 |
| tubulin, alpha 1a | 7.612527947 | TUBA1A | NM_006009 |
| C-type lectin domain family 11, member A | 7.596562932 | CLEC11A | NM_002975 |
| multimerin 2 | 7.518596479 | MMRN2 | XR_111094 |
| collagen, type V, alpha 1 | 7.196249296 | COL5A1 | AK057231///NM_000093 |
| interleukin 27 | 6.957908288 | IL27 | NM_145659 |
| transforming growth factor, beta 1 | 6.719797719 | TGFB1 | NM_000660 |
| growth differentiation factor 6 | 6.076175371 | GDF6 | NM_001001557 |
| nucleoporin 188kDa | 5.928274161 | NUP188 | NM_015354 |
| renin | 5.735120404 | REN | NM_000537 |

Fig. 1J (CONTINUED)

| | | | |
|---|---|---|---|
| ficolin (collagen/fibrinogen domain containing) 3 (Hakata antigen) | 5.579305278 | FCN3 | AK309540///NM_003665 |
| jagged 1 | 5.463099369 | JAG1 | NM_000214 |
| phospholipase A2 receptor 1, 180kDa | 5.433942018 | PLA2R1 | NM_007366 |
| surfactant protein C | 5.410367555 | SFTPC | NM_003018 |
| nucleoporin like 1 | 5.398132496 | NUPL1 | CR605945 |
| oxidative stress induced growth inhibitor 1 | 5.382915594 | OSGIN1 | NM_013370 |
| purinergic receptor P2X, ligand-gated ion channel, 4 | 5.285294847 | P2RX4 | NM_002560 |
| four jointed box 1 (Drosophila) | 5.128219904 | FJX1 | NM_014344 |
| CD109 molecule | 4.935494815 | CD109 | NM_133493 |
| tumor necrosis factor (ligand) superfamily, member 9 | 4.914547082 | TNFSF9 | NM_003811 |
| caveolin 1, caveolae protein, 22kDa | 4.847462968 | CAV1 | NM_001753 |
| anti-Mullerian hormone | 4.635563131 | AMH | NM_000479 |
| dickkopf homolog 1 (Xenopus laevis) | 4.595810362 | DKK1 | NM_012242 |
| thyroglobulin | 4.586026923 | TG | NM_003235 |
| follistatin-like 1 | 4.335395276 | FSTL1 | NM_007085 |
| chemokine-like factor | 4.24138953 | CKLF | NM_181641///NM_016951 |
| interleukin 12A (natural killer cell stimulatory factor 1, cytotoxic lymphocyte maturation factor 1, p35) | 4.203997993 | IL12A | NM_000882 |
| serglycin | 4.200193514 | SRGN | NM_002727 |
| | 4.100725577 | | |
| laminin, beta 1 | 3.9929475 | LAMB1 | BC044633///NM_002291 |
| guanine nucleotide binding protein-like 1 | 3.921002327 | GNL1 | NM_005275 |
| endoglin | 3.90037622 | ENG | NM_000118 |
| bridging integrator 1 | 3.878638643 | BIN1 | NM_139346 |
| collagen, type VIII, alpha 1 | 3.852157185 | COL8A1 | NM_001850 |
| dedicator of cytokinesis 10 | 3.83181559 | DOCK10 | NM_014689 |
| mitochondrial trans-2-enoyl-CoA reductase | 3.75840537 | MECR | NM_001024732 |
| poliovirus receptor | 3.720182967 | PVR | NM_006505 |
| secreted LY6/PLAUR domain containing 1 | 3.711362369 | SLURP1 | NM_020427 |
| growth differentiation factor 5 | 3.513555354 | GDF5 | NM_000557 |
| meteorin, glial cell differentiation regulator | 3.474899111 | METRN | NM_024042 |
| epiregulin | 3.378501764 | EREG | NM_001432 |
| rabaptin, RAB GTPase binding effector protein 2 | 3.352418279 | RABEP2 | NM_024816 |
| neuregulin 1 | 3.336921299 | NRG1 | NM_004495 |

Fig. 1J (CONTINUED)

| Description | Value | Symbol | Accession |
|---|---|---|---|
| transforming growth factorβ3 | 3.336107888 | TGFB3 | NM_003239 |
| brain-derived neurotrophic factor | 3.188190769 | BDNF | NM_170735 |
| thiosulfate sulfurtransferase (rhodanese) | 3.162499897 | TST | NM_003312 |
| glucosidase, beta, acid | 3.152702564 | GBA | NM_001005741 |
| lymphotoxin alpha (TNF superfamily, member 1) | 3.041895567 | LTA | NM_000595 |
| tubulin, beta 8 | 3.032914448 | TUBB8 | NM_177987 |
| eukaryotic translation initiation factor 5A2 | 2.992937171 | EIF5A2 | NM_020390 |
| ectonucleoside triphosphate diphosphohydrolase 6 (putative) | 2.917940581 | ENTPD6 | NM_001247 |
| interferon, alpha 4 | 2.896271028 | IFNA4 | NM_021068 |
| interleukin 6 signal transducer (gp130, oncostatin M receptor) | 2.704125478 | IL6ST | NM_001190981 ///NM_002184 |
| EGF containing fibulin-like extracellular matrix protein 1 | 2.661340849 | EFEMP1 | NM_001039348 |
| tachykinin 4 (hemokinin) | 2.611744567 | TAC4 | NM_170685 |
| tumor necrosis factor (ligand) superfamily, member 13b | 2.600079337 | TNFSF13B | NM_006573 |
| collagen, type XXV, alpha 1 | 2.547336978 | COL25A1 | NM_198721 |
| chemokine (C-C motif) ligand1 | 2.498823606 | CCL1 | NM_002981 |
| interleukin 17D | 2.437773771 | IL17D | NM_138284 |
| Janus kinase 2 | 2.422259121 | JAK2 | NM_004972 |
| wingless-type MMTV integration site family, member 10B | 2.415007034 | WNT10B | NM_003394 |
| interleukin 6 (interferon β2) | 2.393918715 | IL6 | NM_000600///AK298077 |
| cerebral dopamine neurotrophic factor | 2.385407608 | CDNF | NM_001029954 |
| ADAM metallopeptidase domain 9 | 2.381497336 | ADAM9 | NM_003816 |
| interleukin 16 | 2.340589002 | IL16 | NM_004513/// NM_001172128/// BC040272///NM_172217 |
| slit homolog 2 (Drosophila) | 2.325355194 | SLIT2 | NM_004787 |
| proopiomelanocortin | 2.307668809 | POMC | NM_001035256 |
| eukaryotic translation initiation factor 5A-like 1 | 2.269680153 | EIF5AL1 | NM_001099692 |
| SWI/SNF related, matrix associated, actin dependent regulator of chromatin, subfamily d, member 3 | 2.201240932 | SMARCD3 | NM_003078 |
| contactin associated protein-like 3 | 2.157960545 | CNTNAP3 | AK024257///NM_033655 |
| MHC class I polypeptide-related sequence A | 2.072583804 | MICA | NM_000247 |
| annexin A1 | 2.033587436 | ANXA1 | NM_000700 |
| tumor necrosis factor receptor superfamily, member 4 | 2.024829129 | TNFRSF4 | NM_003327 |

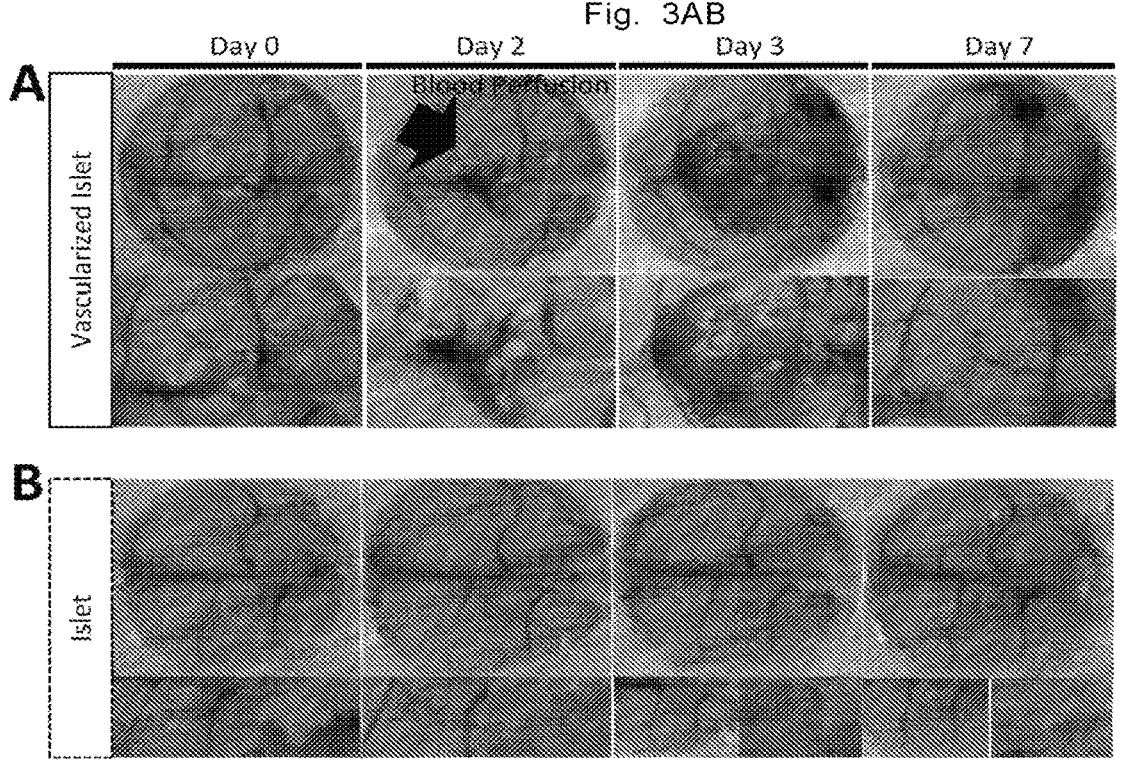

Fig. 5
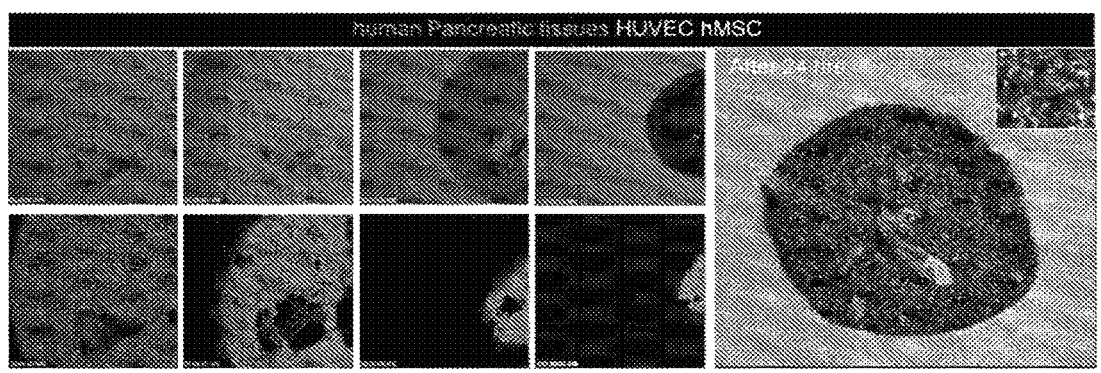
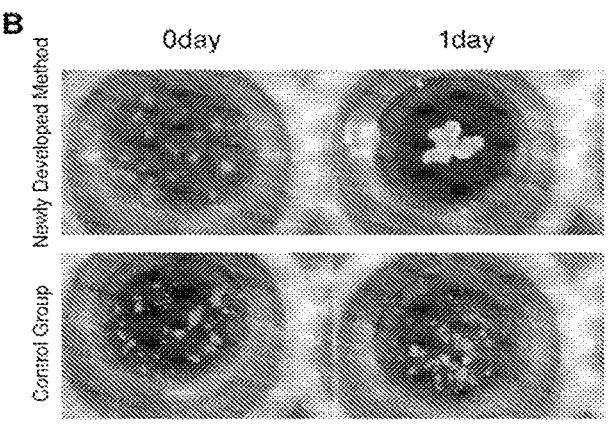
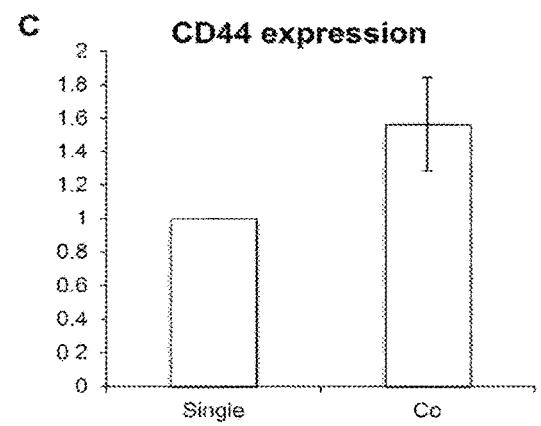

Fig. 6
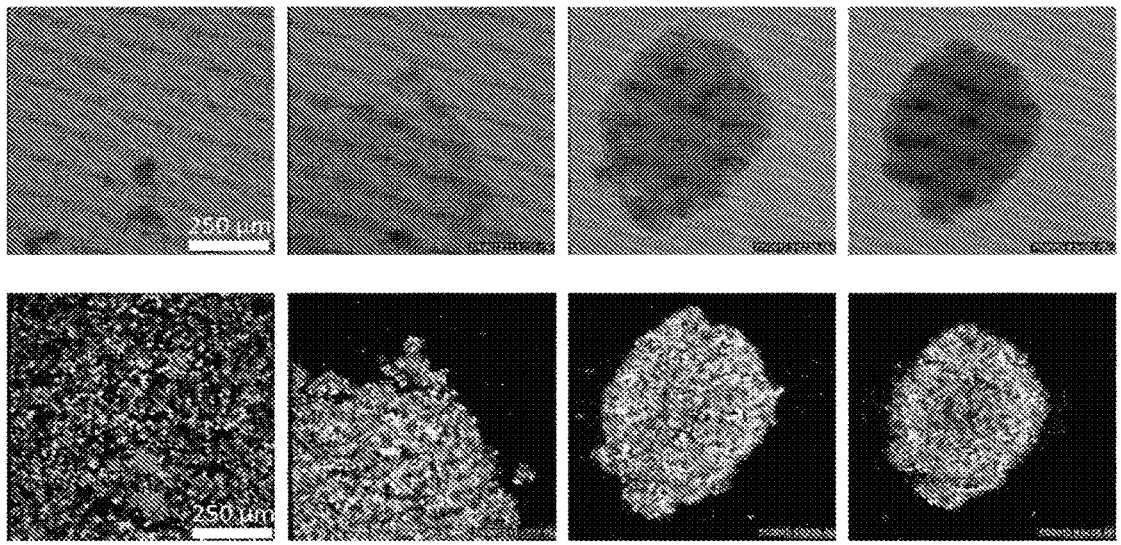
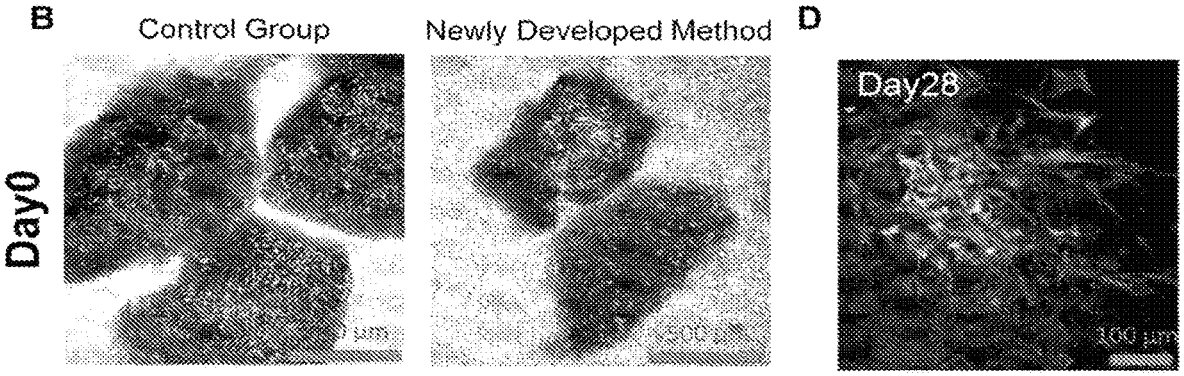
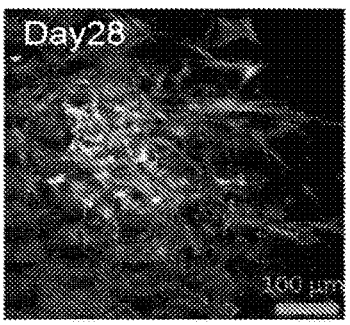
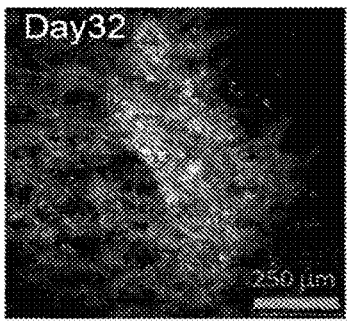
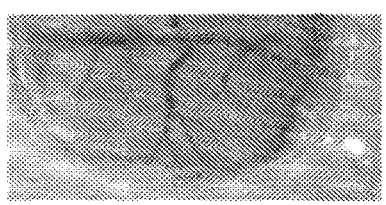 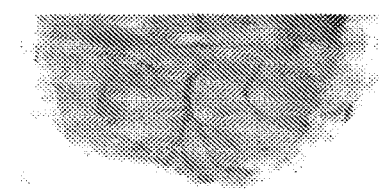 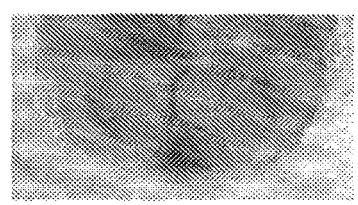

Fig. 9
A
iPS Cells → Directed Differentiation into Endodermal Cells
→ Formation of Tissue Fragment (100-200 μm) ⇒ Integration of Vascular Networks
B
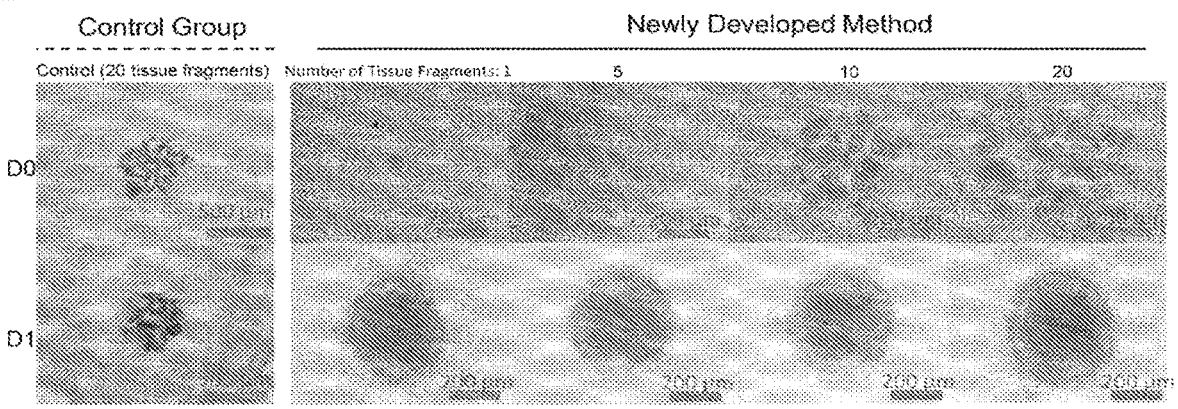
C
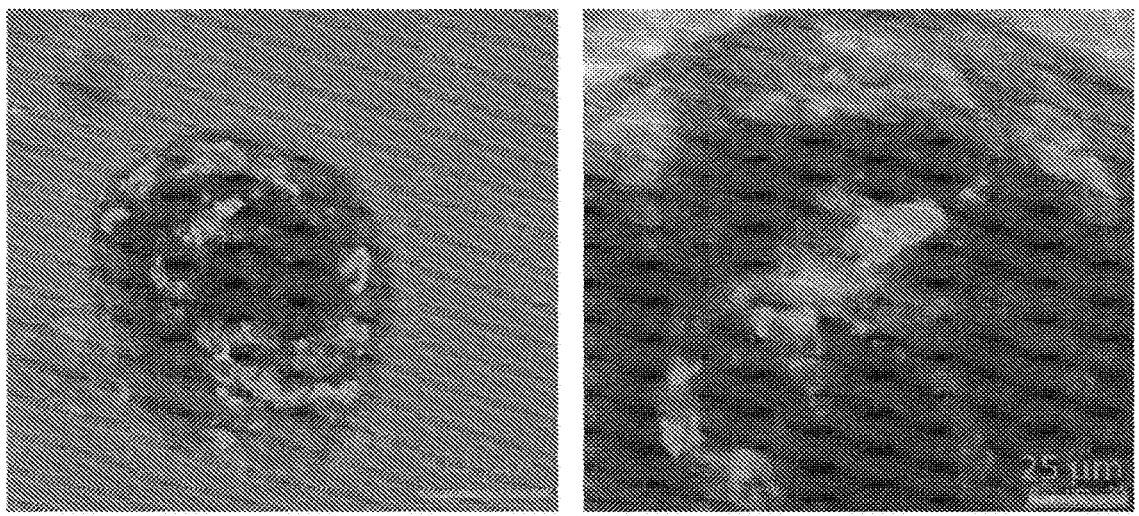

METHOD FOR INTEGRATING BIOLOGICAL TISSUES WITH A VASCULAR SYSTEM

The present application is a continuation application of U.S. patent application Ser. No. 14/906,699 filed Jan. 21, 2016, which is a national stage application of PCT/JP2014/068808 filed Jul. 15, 2014, claiming priority to Japanese Patent Application No. 2013-153056 filed Jul. 23, 2013.

TECHNICAL FIELD

The present invention relates to a method of biological tissues with a vascular system. More specifically, the present invention relates to a method of preparing three-dimensional tissues with vascular networks from tissues induced from pluripotent stem cells, etc. or tissues (such as normal or cancer tissue) isolated from individuals.

BACKGROUND ART

Recently, the use of normal/cancer tissues isolated from individuals or tissues induced from pluripotent stem cells has attracted a great deal of attention as a way to realize drug discovery screening to develop new pharmaceuticals, and regenerative medicine to compensate for the functions of lost organs.

As attempts to induce three-dimensional tissues from pluripotent stem cells or the like, studies have been reported in which spheroidal tissue fragments are formed and directed for cell differentiation in such areas as the liver, pancreas or nerve (Non-Patent Document No. 1: Takayama K, et al., Biomaterials. 2013 February; 34(7):1781-9; Non-Patent Document No. 2: Saito H, et al., PLoS ONE. 2011; 6(12): e28209; and Non-Patent Document No. 3: Eiraku M, et al., Nature 2011, 472, 51-56). However, none of the tissues induced by those methods have vasculatures. Vasculatures have such a role that, once transplanted, they supply the tissues with oxygen and nutrients that are necessary for their survival. What is more, it is believed that, even before blood flows into the tissue, recapitulating three-dimensional tissue structures with blood vessels and cell polarity as well is important for the differentiation, proliferation and maintenance of cells. Therefore, avascular tissues not only fail to engraft upon transplantation and suffer from inner necrosis, but also fail to achieve tissue maturation that is associated with vascularization. It has, therefore, been difficult for avascular tissues to exhibit adequate functions.

Accordingly, for the purpose of integrating vasculatures to a three-dimensional tissue, a method has been invented in which tissues (such as pancreatic islets) isolated from individuals are seeded on a carrier (scaffold material) and cocultured with vascular endothelial cells, fibroblast cells, or the like (Non-Patent Document No. 4: Kaufman-Francis K, et al., PLoS ONE 2012, 7(7): e40741).

However, this method has a limitation in spatial arrangement caused by scaffold materials and cell behavior is greatly affected. Therefore, it is difficult for this method to construct a precise structure like a biological tissue and appropriate interactions between cells are not recapitulated. Consequently, problems arise such as inhibited maturation and proliferation of cells in tissues, and delayed reconstitution of functional vascular networks that leads to poor engraftment after transplantation. There is yet another serious problem that may occur in transplantation and the like; the scaffold material used causes a foreign-body reaction which will result in inflammation or the like.

As described above, reconstitution of three-dimensional tissues having vascular networks is desirable if applications in industry and regenerative medicine are intended but, in fact, no method is yet to be established that is capable of constituting a tissue construct with vasculatures in vitro using a tissue without depending on scaffold materials.

PRIOR ART LITERATURE

Non-Patent Documents

Non-Patent Document No. 1: Takayama K, et al., Biomaterials. 2013 February; 34(7):1781-9
Non-Patent Document No. 2: Saito H, et al., PLoS ONE. 2011; 6(12): e28209
Non-Patent Document No. 3: Eiraku M, et al., Nature 2011, 472, 51-56
Non-Patent Document No. 4: Kaufman-Francis K, et al., PLoS ONE 2012, 7(7): e40741

DISCLOSURE OF THE INVENTION

Problem for Solution by the Invention

For the realization of drug development and regenerative medicine for diseases in the liver, pancreas, kidney, intestine, lung, etc., it is essential to recapitulate a three-dimensional tissue structure associated with vascularization, as well as cell polarity. Briefly, in order to maximize the function of a tissue induced from pluripotent stem cells or a tissue isolated from an individual, it is necessary to form a three-dimensional tissue construct that enables reconstitution of vascular networks.

In this connection, the present inventors have established an innovative three-dimensional culture technique which realized "directed differentiation of organ cells based on organ reconstitution", by utilizing spatiotemporal interactions between different cell lineages (Nature, 499:481-484, 2013; WO2013/047639 titled "Method for Producing Tissue and Organ"). Briefly, by recapitulating those intracellular interactions among organ cells, vascular cells and mesenchymal cells which are essential for early processes of organogenesis, a primordium of steric organ (an organ bud) is induced, thus providing a platform for enabling the generation of functional organs with vascular networks. However, this method starts with organ cells and it has not been elucidated as to whether a primordium of three-dimensional tissue with vascular networks can be generated by using a tissue fragment (tissue).

The present invention aims at providing a method of constituting a tissue construct with vasculatures in vitro from a tissue without depending on scaffold materials.

Means to Solve the Problem

The present inventors have found that close intercellular reactions between organ cells (from which organs develop) and vascular endothelial cells/mesenchymal cells direct the progress of steric tissue formation that involves autonomous tissue structure constitution and cell differentiation (Nature, 499:481-484, 2013; WO2013/047639 titled "Method for Producing Tissue and Organ"). However, it is yet to be made clear if vascular networks can be integrated into tissue fragments.

The present invention attempts to artificially generate steric tissues having vascular networks in vitro starting with tissues by artificially recapitulating such early processes of organogenesis. Further, by transplanting the steric tissues into living bodies, the present invention intends to create a vascularized steric tissue which, when transplanted into a living body after being induced in a culture system, restarts blood flow to enable the tissue function to achieve maturation and maintenance.

The present inventors have cocultured tissues isolated from individuals (up to approximately 10-3,000 μm) or tissues induced from pluripotent stem cells (up to approximately 10-3,000 μm) with vascular cells and mesenchymal cells at appropriate mixing ratios. The methods described below were used for inducing steric tissues.

1. Three-dimensional tissues are formed by coculturing tissues with vascular/mesenchymal cells on a carrier such as Matrigel.
2. Three-dimensional tissues are formed by coculturing tissues with vascular/mesenchymal cells on a plate of such a shape that cells gather in the bottom.

By culturing tissues for a short period according to the above-described methods, it was possible to induce in vitro steric tissues integrated with microvasculatures.

Further, the present inventors successfully created tissues/organs with a highly ordered tissue structure comparable to that of adult tissues; when the steric tissues induced in a culture system were by transplanted into living bodies, reconstruction of functional vascular networks was induced, whereupon blood perfusion was restarted to create the above-described tissues/organs.

This technique of attempting three-dimensional reconstitution of tissues/organs based on the induction of self-organization from tissues through intercellular interactions was not available in the past and is believed to provide a method whose novelty is extremely high.

A summary of the present invention is as described below.
(1) A method of integrating a biological tissue with a vascular system in vitro, comprising coculturing a biological tissue with vascular cells and mesenchymal cells.
(2) The method of (1) above, wherein the biological tissue is cocultured with vascular cells and mesenchymal cells without using scaffold materials.
(3) The method of (1) or (2) above, wherein by coculturing the biological tissue with vascular cells and mesenchymal cells, the biological tissue is integrated with a vascular system so that the function of the biological tissue is maintained and/or improved.
(4) A biological tissue which has been integrated with a vascular system by the method of any one of (1) to (3) above.
(5) A method of preparing a tissue or an organ, comprising transplanting the biological tissue of (4) above into a non-human animal and differentiating the biological tissue into a tissue or an organ in which vascular networks have been constructed.
(6) A method of regeneration or function recovery of a tissue or an organ, comprising transplanting the biological tissue of (4) above into a human or a non-human animal and differentiating the biological tissue into a tissue or an organ in which vascular networks have been constructed.
(7) A method of preparing a non-human chimeric animal, comprising transplanting the biological tissue of (4) above into a non-human animal and differentiating the biological tissue into a tissue or organ in which vascular networks have been constructed.
(8) A method of evaluating a drug, comprising using at least one member selected from the group consisting of the biological tissue of (4) above, the tissue or organ prepared by the method of (5) above, and the non-human chimeric animal prepared by the method of (7) above.
(9) A composition for regenerative medicine, comprising the biological tissue of (4) above.
(10) The composition of (9) above, which is used for preparing a tissue or an organ.
(11) The composition of (9) above, which is used for regeneration or function recovery of a tissue or an organ.
(12) The composition of any one of (9) to (11) above, wherein the biological tissue differentiates into a tissue or an organ with vascular networks upon transplantation into a living body.

According to the present invention, normal/cancer tissues isolated from individuals or tissues induced from pluripotent stem cells are cocultured with vascular cells and mesenchymal cells under appropriate environments, whereby it has become possible to constitute steric tissue constructs in vitro that are integrated with vascular networks. Since vascular networks which are essential for maturation, maintenance, repair, etc. of tissues are provided, highly functional tissues are reconstituted, potentially providing a platform for preparing tissue constructs useful for drug discovery screening and regenerative medicine.

Conventionally, tissue constructs obtained from pluripotent stem cells by directed differentiation remained less mature in the differentiation stage than functional cells that constitute adult tissues. This is because terminal differentiation of functional cells has not been achieved by the conventional directed differentiation method.

According to the present invention, it has become possible to reconstitute a tissue integrated with vascular networks and one may expect that a method of directing terminal differentiation of human functional cells will be established (for example, reconstitution of cell polarity in vasculature); hence, the present invention is highly valuable as a technique for creating human functional cells.

On the other hand, the tissues derived from organs removed from individuals markedly deteriorate in function immediately after they are isolated and it has been difficult to maintain their functions. If an improvement/maintenance of a tissue's function is achieved by integrating vascular networks to it according to the present invention, it may be possible to provide a transplantation technique with remarkable therapeutic efficacy for those patients who have not benefited adequately from the conventional tissue transplantation therapies for the reason that the transplant has no vascular system (e.g., islet transplantation therapy). Further, it will become possible to maximize the functions of various organs in vitro or in vivo and one may expect that the present invention will provide a platform useful for drug discovery screening.

Further, according to the present invention, it is possible to reconstitute a steric human tissue construct having a vascular system. Therefore, it will become possible to generate a tissue or an organ that permits a blood flow in an appropriately arranged vascular system and which has been entirely inachievable by conventional techniques. Consequently, one may expect that the present invention will provide a completely novel analysis system for evaluating the efficacy of pharmaceuticals by which the relationship between development of drug efficacy and blood vessels and other factors that have been difficult to analyze by existing evaluation systems can be evaluated.

Further, the advantages the present invention have over the previously disclosed method (Nature, 499:481-484, 2013; WO2013/047639) in which close intercellular reactions between organ cells and vascular endothelial cells/ mesenchymal cells are relied upon to direct the progress of steric tissue formation that involves autonomous tissue structure constitution and cell differentiation may be enumerated as follows.

1. It is possible to provide a vascular system even for those tissues which are constituted from difficult-to-expand cells (such as pancreatic (3 cells, renal glomerular epithelial/renal tubular epithelial cells, hepatic cells, intestinal epithelial cells, alveolar epithelial cells, tumor cells, trophectodermal cells, iPS cell-derived endodermal cells, iPS cell-derived mesodermal cells, iPS cell-derived from ectodermal cells and iPS cell-derived tissue stem/progenitor cells) and examples of such tissues include pancreatic islets, renal glomeruli, liver tissues, intestinal crypts, pulmonary alveoli, tumor tissues, trophectodermal tissues, iPS cell-derived endodermal cell-derived spheroids, iPS cell-derived mesodermal cell-derived spheroids, iPS cells-derived ectodermal cell-derived spheroids and iPS cell-derived tissue stem/progenitor cell-derived spheroids.

2. It is possible to provide a vascular system for larger tissues. Tissues can be generated by the method disclosed in Nature, 499:481-484, 2013; WO2013/047639 only in the case where isolated cells are used. The method of the present invention has been confirmed to be capable of integrating a vascular system for tissues, rather than cells, that are approximately 10-3,000 μm in size.

3. By integrating a vascular system for a tissue fragment derived from stem cells such as iPS cells, it is possible to recapitulate environments which are similar to the developmental processes of biological tissues and directed differentiation into functional cells that constitute a tissue of interest can be achieved efficiently.

Effect of the Invention

According to the present invention, normal or cancer tissues isolated from individuals or tissues induced from pluripotent stem cells or the like are cocultured with vascular cells and mesenchymal cells, whereby it has become possible to constitute steric tissue constructs in vitro that are integrated with vascular networks. This technique is applicable to, for example, generation of human functional cells; organ transplantation; drug discovery screening; novel analysis systems to evaluate the relationship between development of drug efficacy and blood vessels.

The present specification encompasses the contents disclosed in the specification and/or drawings of Japanese Patent Application No. 2013-153056 based on which the present application claims priority.

BRIEF DESCRIPTION OF THE DRAWINGS

FIG. 1J This figure shows the integration of vascular networks to islet tissues. Specifically, group of genes whose expressions are markedly enhanced by coculture with vascular endothelial cells and mesenchymal stem cells.

FIG. 3AB This figure shows validation of function upon transplantation of vascularized tissue.
A) Macroimaging of the site of transplantation of vascularized islets (yellow arrow indicates blood inflow).
B) Macroimaging of the site of transplantation of islets alone (control group).

FIG. 5 This figure shows the integration of vascular networks to tumor tissues.
A) Autonomous formation of a three-dimensional tissue derived from human pancreatic tumor tissue (red), vascular endothelial cells (green) and mesenchymal stem cells (colorless) using a 24-well dish.
B) Lapse imaging of a three-dimensional tissue formed autonomously from mouse pancreatic cancer tissue, vascular endothelial cells and mesenchymal stem cells at 24 hours of culture using a 24-well dish.
C) Enhanced expression of a cancer stem cell marker (CD44) by formation of vascularized tissue.

FIG. 6 This figure shows the integration of vascular networks to liver tissues.
A) Time-lapse imaging of the process of formation of a three-dimensional tissue derived from mouse liver tissues (green), vascular endothelial cells (red) and mesenchymal stem cells (colorless).
B) Autonomous formation of a three-dimensional tissue derived from mouse liver tissues (green), vascular endothelial cells (red) and mesenchymal stem cells (colorless) using a culture plate (substrate?) of such a shape that cells gather in the bottom.
C) Macroimaging of the site of transplantation of vascularized liver tissues.
D) Reconstitution of a vascular system inside the vascularized liver tissues.

FIG. 9 This figure shows the integration of vascular networks to iPS cell-derived endodermal tissues.
A) Outline of the method of application to human iPS cell-derived endodermal cell spheroids.
B) Autonomous formation of a three-dimensional tissue using human iPS cell-derived endodermal tissue fragments, vascular endothelial cells and mesenchymal stem cells.
C) Fluorescent image observation of a three-dimensional tissue constituted from human iPS cell-derived endodermal tissue fragments (colorless), vascular endothelial cells (red) and mesenchymal stem cells (colorless).

BEST MODES FOR CARRYING OUT THE INVENTION

Figure 1A:
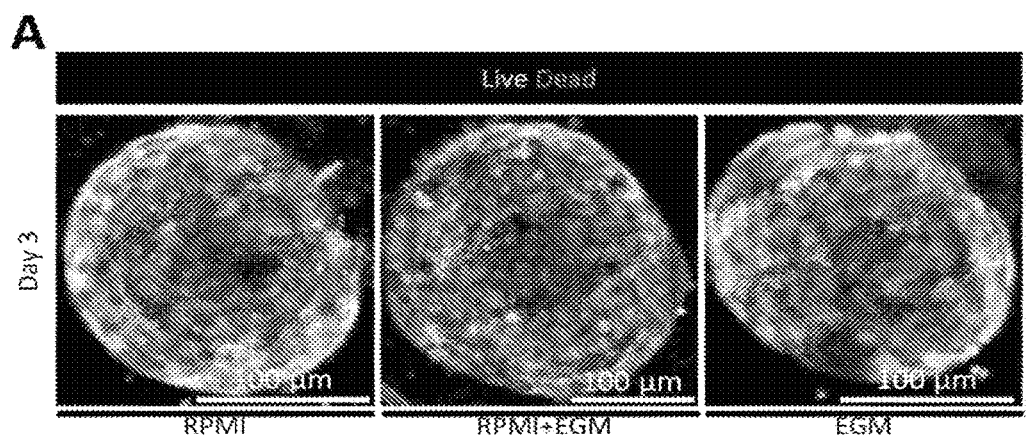
FIG. 1A This figure shows the integration of vascular networks to pancreatic islet (hereinafter, frequently referred to simply as "islet") tissues.
A) Validation of media for culturing mouse islets using Live/Dead' Cell Imaging Kit (green: viable cells, red: dead cells).

Hereinbelow, the present invention will be described in detail.

The present invention provides a method of integrating a vascular system for a biological tissue in vitro, comprising coculturing a biological tissue with vascular cells and mesenchymal cells.

In the present specification, the term "biological tissue" refers to a construct constituted from a plurality of cells. For example, normal/abnormal tissues or cancer tissues isolated from individuals as well as tissues induced from pluripotent stem cells (such as induced pluripotent stem cells (iPS cells) and embryonic stem cells (ES cells)), tissue stem/progenitor cells, differentiated cells or the like may be enumerated. As biological tissues, those derived from humans may primarily be used. Biological tissues derived from non-human animals (e.g., animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may also be used.

In the present specification, the term "vascular system" refers to a structure composed of vascular endothelial cells and its supporting cells. Vascular systems not only maintain tissues but also play an important role in the maturation process of tissues. Vascular structures have such a role that, once transplanted, they supply the tissues with oxygen and nutrients that are necessary for their survival. What is more, it is believed that even before blood flows into the tissue, recapitulating three-dimensional tissue structures with blood vessels and cell polarity as well as important for the differentiation, proliferation and maintenance of cells. Therefore, avascular tissues not only fail to engraft upon transplantation and suffer from inner necrosis, but also fail to achieve tissue maturation that is associated with vascularization. It has, therefore, been difficult for avascular tissues to exhibit adequate functions.

In the present specification, the terms "integrating a vasculature system" and "vascularization" mean that a vascular system composed of vascular endothelial cells and its supporting cells is integrated directly with a target tissue. When a biological tissue integrated with a vascular system is transplanted into a living body, maturation of blood vessels is observed and upon connecting to the host blood vessels, blood perfusion starts, enabling induction to a functional tissue/organ having vascular networks.

Vascular cells may be isolated from vascular tissues but they are in no way limited to those isolated therefrom. Vascular cells may be derived from totipotent or pluripotent cells (such as iPS cells and ES cells) by induction of differentiation. As vascular cells, vascular endothelial cells are preferable. In the present specification, the term "vascular endothelial cells" means cells constituting vascular endothelium or cells capable of differentiating into such cells (for example, vascular endothelial progenitor cells and vascular endothelial stem cells). Whether a cell is vascular endothelial cell or not can be determined by checking to see if they express marker proteins such as TIE2, VEGFR-1, VEGFR-2, VEGFR-3 and CD31 (if any one or more of the above-listed marker proteins are expressed, the cell can safely be regarded as a vascular endothelial cell). Further, as markers for vascular endothelial progenitor cells, c-kit, Sca-1, etc. have been reported. If these markers are expressed, the cell of interest can be confirmed as a vascular endothelial progenitor cell (S. Fang, et al., PLOS Biology, 2012; 10(10): e1001407). Among the terms used by those skilled in the art, the following are included in the "vascular endothelial cell" of the present invention: endothelial cells, umbilical vein endothelial cells, endothelial progenitor cells, endothelial precursor cells, vasculogenic progenitors, hemangioblast (H J. Joo, et al. Blood. 25; 118(8):2094-104 (2011)) and so on. As vascular cells, human-derived cells are mainly used. However, vascular cells derived from non-human animals (e.g., animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may also be used. Vascular cells may be obtained from cord blood, umbilical cord vessels, neonatal tissues, liver, aorta, brain, bone marrow, adipose tissues, and so forth.

In the present invention, the term "mesenchymal cells" means connective tissue cells that are mainly located in mesoderm-derived connective tissues and which form support structures for cells that function in tissues. The "mesenchymal cell" is a concept that encompasses those cells which are destined to, but are yet to, differentiate into mesenchymal cells. Mesenchymal cells to be used in the present invention may be either differentiated or undifferentiated. Preferably, undifferentiated mesenchymal cells are used. Whether a cell is an undifferentiated mesenchymal cell or not may be confirmed by checking to see if the cell expresses marker proteins such as Stro-1, CD29, CD44, CD73, CD90, CD105, CD133, CD271 or Nestin (if any one or more of the above-listed marker proteins are expressed, the cell can safely be regarded as an undifferentiated mesenchymal cell). A mesenchymal cell in which none of the above-listed markers is expressed can be judged as differentiated mesenchymal cell. Among the terms used by those skilled in the art, the following are included in the "mesenchymal cell" of the present invention: mesenchymal stem cells, mesenchymal progenitor cells, mesenchymal cells (R. Peters, et al. PLoS One. 30; 5(12):e15689 (2010)) and so on. As mesenchymal cells, human-derived cells are mainly used. However, mesenchymal cells derived from non-human animals (e.g., animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may also be used.

The size of a biological tissue to be cocultured with vascular cells and mesenchymal cells may be approximately 10-500 μm, but is not limited to this range. Preferably, the size is approximately 100-300 μm. More preferably, the size is approximately 100-150 μm.

The numbers of vascular cells and mesenchymal cells to be used for coculture may each be about $2 \times 10^2$-$1 \times 10^5$ cells, preferably, about $2 \times 10^2$-$5 \times 10^4$ cells, and more preferably, about $1 \times 10^4$ cells, per biological tissue of approx. 150 μm in size.

The culture ratio of vascular cells and mesenchymal cells in coculture is not particularly limited if it is within such a range that a vascular system is provided for biological tissues. A preferable cell count ratio as expressed by the vascular cell to mesenchymal cell is 10-3:3-1.

The number of biological tissues in coculture is not particularly limited if it is within such a range that a vascular system is provided for biological tissues. Preferably, 1-100 tissues approx. 100-150 μm in diameter are used for a mixture of $1 \times 10^4$ vascular cells and $1 \times 10^4$ mesenchymal cells.

Either one or both of vascular cells and mesenchymal cells may be substituted by substances such as factors secreted by vascular cells, factors secreted by mesenchymal cells, and factors secreted as a result of the presence of both vascular cells and mesenchymal cells.

Examples of the substances such as factors secreted by vascular cells, factors secreted by mesenchymal cells, and factors secreted as a result of the presence of both vascular cells and mesenchymal cells include, but are not limited to, FGF2, FGF5, BMF4, BMP6, CTGF, angiopoietin 2, chemokine (C—C motif) ligand 14 and von Willebrand factor.

With respect to the amount of addition of these substances, FGF2 may be added at 10-100 ng/ml, preferably at about 20 ng/ml, per $1\times10^6$ cells; and BMF4 may be added at 10-100 ng/ml, preferably at about 20 ng/ml, per $1\times10^6$ cells.

The medium used for culturing is not particularly limited. Any medium may be used as long as it enables the integration of a vascular system for biological tissues. Preferably, a medium for culturing vascular cells (in particular, vascular endothelial cells), a medium for culturing biological tissues or a mixture of these two media may be used. As a medium for culturing vascular cells (in particular, vascular endothelial cells), any medium may be used but, preferably, a medium containing at least one of the following substances may be used: hEGF (recombinant human epithelial growth factor), VEGF (vascular endothelial growth factor), hydrocortisone, bFGF, ascorbic acid, IGF1, FBS, antibiotics (e.g., gentamycin or amphotericin B), heparin, L-glutamine, phenol red and BBE. As a medium for culturing vascular endothelial cells, EGM-2 BulletKit (Lonza), EGM BulletKit (Lonza), VascuLife EnGS Comp Kit (LCT), Human Endothelial-SFM Basal Growth Medium (Invitrogen), human microvascular endothelial cell growth medium (Toyobo) or the like may be used. The medium used for culturing biological tissues is not particularly limited but, as a medium for culturing islet tissues, RPMI1640 (Wako) or EGM™ BulletKit™ (Lonza CC-4133) supplemented with 10% fetal bovine serum (BWT Lot.S-1560), 20 mmol/L L-glutamine (Gibco) and 100 µg/ml penicillin/streptomycin (Gibco) may preferably be used; as a medium for culturing renal tissues (such as renal glomeruli), RPMI1640 (Wako) supplemented with 20% fetal bovine serum (BWT Lot.S-1560), 100 µg/ml penicillin/streptomycin (Gibco) and Insulin-Transferrin-SeleniumX (Gibco) may preferably be used; as a medium for culturing intestinal tissues (such as crypt fragments), RPMI1640 (Wako) supplemented with 20% fetal bovine serum (BWT Lot.S-1560), 100 µg/ml penicillin/streptomycin (Gibco) and Insulin-Transferrin-SeleniumX (Gibco) may preferably be used; as a medium for culturing liver tissues, DMEM/F12 (Invitrogen) supplemented with 10% fetal bovine serum (ICN Lot. 7219F), 2 mmol/L L-glutamine (Gibco), 100 µg/mL penicillin/streptomycin (Gibco), 10 mmol/L nicotinamide (Sigma), 50 µmol/L 2-Mercaptoethanol, $1\times10^{-7}$ mol/L 6.5% dexamethasone (Sigma), $2.6\times10^{-4}$ M L-Ascorbic acid 2-phosphate sesquimagnesium salt hydrate (Sigma), 5 mmol/L HEPES (Dojindo), 1 µg/mL Human recombinant insulin expressed in yeast (Wako), 50 ng/mL Human recombinant HGF expressed in Sf21 insect cells (Sigma) and 20 ng/mL Mouse Submaxillary Glands EGF (Sigma) may preferably be used; as a medium for iPS cell-derived endodermal tissues, RPMI1640 (Wako) supplemented with 1% B27 SUPPLEMENT X50 (Invitrogen 17504-044), 10 nG/ML BFGF Recombinant Human (Wako 060-04543) and 20 nG/ML BMP4 Recombinant Human (R&D 314-BP) may preferably be used; as a medium for iPS cell-derived hepatic endodermal tissues, a medium kit for sole use with hepatocytes (HCM™ BulletKit™ lonza CC3198) freed of hEGF (recombinant human epithelial growth factor) and supplemented with 0.1 µM Dexamethasone (Sigma-Aldrich), 10 ng/ml Oncostatin M (R&D) and 10 ng/ml HGF (PromoKine) may preferably be used; and as a medium for cancer tissues or pulmonary tissues, the same media as that for vascular cells may preferably be used.

Preferably, biological tissues are seeded on a substrate such as gel and cocultured with vascular cells and mesenchymal cells. The substrate may be a base material having a stiffness of 0.5-25 kPa. Examples of such base material include, but are not limited to, gels (e.g., ranging from a stock solution to a 4-fold dilution of Matrigel™, agarose gel, acrylamide gel, hydrogel, collagen gel or urethane gel).

Alternatively, biological tissues may be cocultured with vascular cells and mesenchymal cells on a plate of such a shape that cells gather in the bottom. The plate used for this purpose is not particularly limited as long as it has such a shape that cells gather in the bottom. For example, PrimeSurface™ 96-well U plate (Sumitomo Bakelite) may be used.

The temperature at the time of culture is not particularly limited but it is preferably 30-40° C., more preferably 37° C.

The time period of culture is not particularly limited but it is preferably 12-144 hours. For vascularization of adult tissues such as islets, the culture period is more preferably about 12-24 hours. For vascularization of iPS cell-derived tissues, the culture period is more preferably about 48-72 hours. For vascularization of cancer tissues, the culture period is more preferably about 12-72 hours.

The biological tissue that has been integrated with a vascular system by the method of the present invention may be a construct characterized in that the complex tissue is autonomously formed by cells or tissues. Further, the biological tissue that has been integrated with a vascular system by the method of the present invention may be a complex tissue in which the vascular system directly integrates with (i.e., adheres to, connects to, or continues to) the tissue.

In the method of the present invention, it is possible to provide a vascular system for a biological tissue by coculturing the biological tissue with vascular cells and mesenchymal cells without using scaffold materials.

When a vascular system is provided for a biological tissue by coculturing the biological tissue with vascular cells and mesenchymal cells, the function of the biological tissue can be maintained and/or improved. In addition to the maintenance and improvement of the function of the biological tissue, transplantation efficiency is sufficiently improved to provide a treatment method having remarkable therapeutic effects.

Further, the present invention which enables reconstruction of a vascular system will leads to the establishment of a method by which terminally differentiated cells can be efficiently induced from tissues derived from pluripotent stem cells such as iPS cells and ES cells.

The biological tissue that has been integrated with a vascular system by the method of the present invention may be a complex tissue whose vascular system is capable of rapidly functioning in vivo. Briefly, when the biological tissue integrated with a vascular system by the method of the present invention is transplanted into a living body (host), the time it takes for anastomosis to host vessels to occur and for blood to flow in can be greatly shortened, compared to cases where scaffold materials are used [for example, when scaffold materials are used, 12 days are taken (Engineered blood vessel networks connect to host vasculature via wrapping-and-tapping anastomosis. Blood. 2011 Oct. 27; 118 (17):4740-9) whereas the method of the present invention takes only 1 to 2 days (see Examples described later)].

When the biological tissue integrated with a vascular system by the method of the present invention is transplanted into a non-human animal, vascular networks are constructed in the transplanted tissue and blood perfusion starts to enable the creation of a tissue or an organ having a highly ordered tissue structure. Therefore, the present invention provides a method of preparing a tissue or an organ, comprising transplanting a human or a non-human animal with a biological tissue that has been integrated with a vascular system by coculturing with vascular cells and mesenchymal cells, and differentiating the biological tissue into a tissue or an organ in which vascular networks have been constructed. Non-human animals to be used in this method include, but are not limited to, animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like may be used. Further, in order to avoid immunorejection, the non-human animal to be used herein is preferably an immunodeficient animal.

The site of transplantation of the biological tissue integrated with a vascular system may be any site as long as transplantation is possible. Specific examples of the transplantation site include, but are not limited to, the intracranial space, the mesentery, the liver, the spleen, the kidney, the subcapsular space of the kidney, and the supraportal space. When the biological tissue is to be transplanted into the intracranial space, about 1 to 12 biological tissues of 500 µm in size, prepared in vitro, may be transplanted. When the biological tissue is to be transplanted into the mesentery, about 1 to 12 biological tissues of 3-8 mm in size, prepared in vitro, may be transplanted. When the biological tissue is to be transplanted into the supraportal space, about 1 to 12 biological tissues of 3-8 mm in size, prepared in vitro, may be transplanted. When the biological tissue is to be transplanted into the subcapsular space of the kidney, about 1 to 6 biological tissues of 3-8 mm in size, prepared in vitro, may be transplanted. When the biological tissue is to be transplanted into the liver, spleen, kidney, lymph node or blood vessel, about 100-2000 biological tissues of 100-200 µm in size, prepared in vitro, may be transplanted.

The tissues and organs prepared as described above may be used in drug discovery screening and regenerative medicine.

Thus, the present invention provides a method of regeneration or function recovery or a tissue or an organ, comprising transplanting a human or a non-human animal with a biological tissue that has been integrated with a vascular system by coculturing with vascular cells and mesenchymal cells into, and differentiating the biological tissue into a tissue or an organ in which vascular networks have been constructed. Non-human animals to be used in this method include, but are not limited to, animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like may be used.

Further, the present invention provides a composition for regenerative medicine, comprising a biological tissue that has been integrated with a vascular system by coculturing with vascular cells and mesenchymal cells.

The composition of the present invention can be transplanted into a living body to prepare a tissue or an organ. The composition of the present invention can also be transplanted into a living body to regenerate a tissue or an organ or recover its function. As the living body, not only humans but also animals (such as ones used as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may be used.

After the composition of the present invention is transplanted into a living body, the biological tissue is capable of differentiating into a tissue or an organ having vascular networks. In the vascular networks, blood perfusion can occur. It is believed that the occurrence of blood perfusion in the vascular networks enables generation of a tissue or an organ having a highly ordered tissue structure either comparable or nearly comparable to the tissue structure of adult tissues.

The composition of the present invention may contain additives including, for example, tissue vascularization promoters such as FGF2, HGF and VEGF; gelatin sponge for hemostasis associated with transplantation (product name: Spongel; Astellas Pharma); and tissue adhesives used to fix transplanted tissues, such as Bolheal (Teijin Pharma), Beriplast™ (CSL Behring) and TachoComb™ (CSL Behring).

The present invention also provides a method of preparing a non-human chimeric animal, comprising transplanting a non-human animal with a biological tissue that has been integrated with a vascular system by coculturing with vascular cells and mesenchymal cells, and differentiating the biological tissue into a tissue or an organ in which vascular networks have been constructed. The non-human animal (such as mouse) transplanted with the biological tissue integrated with a vascular system can mimic the physiological function of the animal species (such as human) from which the vascularized biological tissue is derived. Non-human animals include, but are not limited to, animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like may be used. Further, in order to avoid immunorejection, the non-human animal to be used herein is preferably an immunodeficient animal.

Further, the present invention also provides a method of evaluating a drug, comprising using at least one member selected from the group consisting of the biological tissue integrated with a vascular system by the above-described method, the tissue or organ prepared from the vascularized biological tissue, and the non-human chimeric animal transplanted with the vascularized biological tissue. Specific examples of drug evaluation include, but are not limited to, evaluation of drug metabolism (e.g., prediction of drug metabolism profiles), evaluation of drug efficacy (e.g., screening for drugs that are effective as pharmaceuticals; confirmation of the effect of pharmaceuticals such as the relationship between drug efficiency and blood vessels; etc.), toxicity evaluation, and evaluation of drug interactions.

With respect to evaluation of drug efficacy, human-type drug metabolism profiles may be obtained as follows. Briefly, a biological human tissue integrated with a vascular system, a human tissue or organ prepared from a biological tissue integrated with a vascular system, or a non-human chimeric animal transplanted with a biological human tissue integrated with a vascular tissue is administered with a candidate compound for pharmaceuticals; then, biological samples are taken and analyzed. According to these processes, prediction of the distribution/metabolism/excretion process of pharmaceuticals in humans—which has been extremely difficult to achieve by conventional methods—becomes possible and one may. expect that the development of safe and efficacious pharmaceuticals can be remarkably accelerated.

Screening for drugs that are effective as pharmaceuticals is carried out as follows. Briefly, starting with a tissue induced from a cell/tissue established from a diseased patient, a biological tissue integrated with a vascular system, a tissue or an organ prepared from this vascularized biological tissue, or a non-human chimeric animal transplanted with this vascularized biological tissue is prepared. Then, a candidate compound for pharmaceuticals is administered for analyses. As a result, one may expect that the prediction accuracy of drug efficacy in actual administration to humans—which has been insufficient in conventional in vitro tests—can be greatly improved.

Confirmation of the relationship between drug efficacy and blood vessels is achieved as follows. Briefly, a biological tissue integrated with a vascular system, a tissue or an organ prepared from this vascularized biological tissue, or a non-human chimeric animal transplanted with this vascularized biological tissue is administered with a given drug. Then, the concentration distribution of the drug in tissues at the vicinity of blood vessels and the desired drug's effect on cells are measured.

In tumor tissues, for example, targeting cancer stem cells which are clinically considered a cause of recurrence or metastasis is believed to be an important therapeutic strategy. On the other hand, it is known that when cancer stem cells are present at the vicinity of blood vessels, vascular permeability is decreased and anticancer agents are difficult to infiltrate whereas if they are distant from blood vessels, diffusion of anticancer agents is insufficient. For developing drugs targeting at cancer stem cells, it has been important to reconstitute a three-dimensional tumor tissue that starts from blood vessels and use this tissue for evaluation. By using the method of the present invention, the evaluation of drug efficacy based on cell/tissue polarity with respect to blood vessels which has been entirely inachievable by conventional methods can be realized and development of drugs with higher therapeutic effects can be performed.

In the case of toxicity evaluation, a biological tissue integrated with a vascular system, a tissue or an organ prepared from this vascularized biological tissue or a non-human chimeric animal transplanted with this vascularized biological tissue is used as a target which is administered a test substance and thereafter the expressions of tissue disorder markers are measured, whereby the accuracy in disorder prediction can be improved.

Development of anticancer agents and other pharmaceuticals that may have toxicity problems has required huge costs and prolonged periods for evaluating drug toxicity. By creating a micro-environment mimicking the inside of a living body using vascularized tissues, toxicity tests on tissues—which have heretofore been difficult to evaluate—become available. Briefly, by carrying out toxicity evaluation on blood vessels, diseased cells and normal cells, one may expect that the research and development of new pharmaceuticals can be remarkably expedited.

Evaluation of drug interactions may be performed as follows. Briefly, a biological tissue integrated with a vascular system, a tissue or an organ prepared from this vascularized biological tissue or a non-human chimeric animal transplanted with this vascularized biological tissue is used as a target which is administered with a plurality of drugs; then, examination of each drug's pharmacokinetics (distribution/metabolism/excretion processes), toxicity evaluation, and drug efficacy evaluation are performed.

The function level of the cells obtained from pluripotent stem cells by conventional directed differentiation remained less mature in the differentiation stage than those functional cells that constitute adult tissues. If, by the method of the present invention, terminally differentiated functional cells are obtainable from tissues induced from pluripotent stem cells or the like, it will be a revolutionary technique of directed differentiation that serves as an important platform adapted for industrial production of human functional cells. For example, human hepatocytes or human hepatic stem cells isolated from the human liver tissues artificially prepared by the present invention will enable mass production of human adult hepatocytes which are necessary for drug discovery and development.

Further, by integrating cancer tissues or normal tissues with steric vascular networks, a revolutionary screening technique will be realized which can evaluate drug efficacy from a totally new viewpoint such as the correlation between development of drug efficacy and spatial arrangement of blood vessels—a problem that has remained unsolved in drug discovery and development.

Conventionally, medical transplantation targeting such diseases as diabetes was mainly tissue transplantation therapy involving the transplantation of islet tissues or the like extracted from bodies derived from brain-dead donors, for example. However, engraftment of transplants after the transplantation was remarkably low because the transplants used in tissue transplantation therapy had no vascular system. Thus, the therapeutic effect was rather limited. According to the present invention, it has become possible to supply vascularized transplants that can solve this problem. If industrial production of human tissues/organs for therapeutic purposes that are integrated with vascular networks becomes possible, new tissues/organs for transplantation which are expected to provide higher therapeutic effects can be supplied, potentially serving as a revolutionary medical technique.

EXAMPLES

Hereinbelow, the present invention will be described in more detail with reference to the following Examples.

[Example 1] Integration of Vascular Networks for Pancreatic Islet Tissues

[Methods]
1. Isolation of Mouse Pancreatic Islets

Isolation of mouse pancreatic islets (hereinafter, frequently referred to simply as "islets") was performed mainly according to the method of Dong et al. (Title of the document: A protocol for islet isolation from mouse pancreas). C57BL/6J mice (Japan SLC, Inc.) anesthetized with diethyl ether (Wako) were laparotomized after disinfection of the abdomen with 70% ethanol. The ampulla of Vater (that is a joint between the common bile duct and the duodenum) was ligated. Subsequently, a 27 G injection needle was inserted into the site of junction of the cystic duct and the hepatic duct, and 3 ml of collagenase XI solution (1,000 U/ml) (Sigma, cet. No. C7657) prepared with Hanks' buffer (HBSS, Gibco) was injected to fill the entire pancreas with collagenase XI solution. The pancreas was cut out and placed in a 50 ml tube containing collagenase XI solution, which was then shaken at 37.5° C. for 15 min. After digestion of the pancreas, 25 ml of ice-cooled HBSS (containing 1 mM $CaCl_2$) was added to the tube for washing. Then, the tube was centrifuged (290 g, 30 sec, 4° C.), followed by removal of the supernatant. After re-washing and re-centrifugation, 15 ml of HBSS was added to the tube. The resultant content was filtered with a 70 μm mesh cell strainer. The residue was entirely transferred into a petri dish using an originally prepared medium [EGM™ BulletKit™ (Lonza CC-4133) originally modified for the purpose of culturing islets].

2. Selection of Mouse Pancreatic Islets

When the mouse islets isolated in 1 above were observed under a stereomicroscope, orange-colored spherical mouse islets (150-250 μm in diameter) could be confirmed. These islets were transferred to an islet culture medium with a Pipetman.

3. Primary Culture of Mouse Pancreatic Islets

Mouse islets were cultured using an originally prepared medium [EGM™ BulletKit™ (Lonza CC-4133) supplemented with 10% fetal bovine serum (BWT Lot. S-1560), 20 mmol/L L-glutamine (Gibco) and 100 μg/ml penicillin/streptomycin (Gibco)] in a 37° C. 5% $CO_2$ incubator.

4. Cell Culture

Normal human umbilical vein endothelial cells (HUVECs) (Lonza CC-2517) were cultured using a medium prepared especially for culturing HUVECs [EGM™ BulletKit™ (Lonza CC-4133)] within a guaranteed passage number (5 passages). Human mesenchymal stem cells (hMSCs) (Lonza PT-2501) were cultured using a medium prepared especially for culturing hMSCs [MSCGM™ BulletKit™ (Lonza PT3001)] within a guaranteed passage number (5 passages). Both HUVECs and hMSCs were cultured in a 37° C., 5% $CO_2$ incubator.

5. Fluorescence Labeling with Retrovirus Vectors

All the gene recombination experiments were performed in P2 level safety cabinets under an approval of the Gene Recombination Committee of Yokohama City University.

Production of virus vectors pGCDΔNsamEGFP and pGCDΔNsamKO was performed by the method described below. Briefly, 293GPG/pGCDΔNsamEGFP cells (kindly provided by Mr. Masafumi Onodera) and 293GPG/pGCDΔNsamKO cells (kindly provided by Mr. Masafumi Onodera) were seeded on poly-L-lysine-coated dishes and cultured in an especially prepared medium (designated "293GPG medium"). Briefly, DMEM (Sigma) containing 10% fetal bovine serum (Gibco), 2 mmol/L L-glutamine (Gibco), 1×penicillin/streptomycin (Gibco), 1 μg/mL tetracycline hydrochloride (Sigma T-7660), 2 μg/mL puromycin (Sigma P-7255) and 0.3 mg/mL G418 (Sigma A-1720) was used. Cultivation was carried out in a 37° C., 10% $CO_2$ incubator. When cells reached about 80% confluence, the medium was exchanged with a different medium equivalent to 293GPG medium except that it was freed of tetracycline hydrochloride, puromycin and G418 (this medium is designated "293GP medium") (the day of exchange shall be day 0). After another medium exchange at day 3, the viruses were recovered together with the medium starting at day 4, followed by filling with 293GP medium again. The recovered medium was passed through a 0.45 μm filter and stored temporarily at 4° C. The medium recovered up to day 7 by the above-described procedures was centrifuged (6000 G, 4° C., 16 hr). To the resultant pellet, 400 μL of Stempro (Invitrogen) was added. After shaking at 4° C. for 72 hr, the resultant solution was recovered and stored at −80° C. (designated "100-fold concentrated virus solution").

HUVECs were cultured until they reached 30-50% confluence. Protamine (Sigma) was added to the medium to give a final concentration of 0.4 μm/mL. To HUVECs, pGCDΔNsamEGFP was added. Then, cells were infected in a 37° C., 5% $CO_2$ incubator for 4 hr and washed with PBS twice. The medium was exchanged with a fresh one, followed by incubation in a 37° C., 5% $CO_2$ incubator again. These operations were repeated four times and the cells were fluorescence labeled.

6. Examination of Media for Mouse Pancreatic Islets

Media for pancreatic islets were prepared using RPMI1640 (Wako) and an endothelial cell medium (EGM™ BulletKit™) (Lonza CC-4133) separately. One mouse islet was left standing in each well of PrimeSurface™ 96-well U plates (Sumitomo Bakelite) filled with respective media, followed by incubation in a 37° C. incubator. Subsequently, 20 μl of LIVE/DEAD™ Cell Imaging Kit (Life Technologies Japan) was added, followed by incubation in a 37° C., 5% $CO_2$ incubator for 15 min. Then, islets were observed under a confocal microscope (LEICA TCS-SP5).

7. Preparation of Three-Dimensional Tissues with Human Vasculatures Using 24-Well Flat Bottom Plate For the purpose of chronological observation, EGFP-HUVECs ($2.0 \times 10^6$ cells) and hMSCs ($4.0 \times 10^5$ cells) were mixed and centrifuged at 950 rpm for 5 min. After removal of the supernatant, cells were suspended in 20 μl of a medium for islets, and gel was solidified [Briefly, Matrigel (BD) and the medium for islets were mixed at 1:1; the resultant solution was poured into each well (300 μl/well); and the plate was left standing in a 37° C., 5% $CO_2$ incubator for 10 min or more until solidification occurred]. Cells were seeded on each well of a 24-well flat bottom plate (BD) in which 300 mouse islets/well had been left standing. After seeding, the plate was left standing in a 37° C. incubator for 10 min. After 10 minutes, 1 ml of the medium for islets was added gently down the well wall, followed by incubation in a 37° C. incubator for one day.

8. Preparation of Three-Dimensional Tissues with Human Vasculatures Using 96-Well U Plate Mouse islets were left standing in each well of PrimeSurface™ 96-Well U Plate (Sumitomo Bakelite) preliminarily filled with the medium for islets, and HUVECs and hMSCs were seeded in each well. The plate was subsequently incubated in a 37° C. incubator for one day.

9. Chronological Observation of Cocultured Cells Using Stereomicroscope

Coculture was performed for tracking chronological changes with a stereomicroscope. Briefly, 10 mouse islets were left standing in each well of PrimeSurface™ 96-Well U Plate. In each well, HUVECs ($1.0 \times 10^4$ cells) and hMSCs ($1.0 \times 10^3$ cells) were seeded. After seeding, the plate was mounted in a stereomicroscope (Leica DFC300FX) to observe morphological changes caused by coculture.

10. Validation of Islet Cell's Survival Rates Using Transwell Plate

Mouse islets (30) were left standing in the bottom of each well of 24-well Transwell plates. Inserts were placed in other 24-well plates. HUVECs ($1 \times 10^5$ cells), hMSCs ($2 \times 10^4$ cells) and a mixture of HUVECs ($1 \times 10^5$ cells) and hMSCs ($2 \times 10^4$ cells) were individually seeded in those inserts, which were then placed in the 24-well plates where mouse islets had been left standing. The plates were incubated in a 37° C., 5% $CO_2$ incubator overnight. Subsequently, 200 μl of LIVE/DEAD™ Cell Imaging Kit (Life Technologies, Japan) was added to each well of the 24-well plates where mouse islets had been left standing. Then, the plates were incubated in a 37° C., 5% $CO_2$ incubator for 15 min, followed by observation under a confocal microscope (LEICA TCS-SP5).

11. Validation of Islet Cell's Survival Rates Using 96-Well U Plate

Into the medium for the three-dimensional tissue prepared in section 8 above, 20 μl of LIVE/DEAD' Cell Imaging Kit (Life Technologies, Japan) was added, followed by incubation in a 37° C., 5% $CO_2$ incubator for 15 min. Subsequently, cells were observed under a confocal microscope.

12. Quantitative Determination of Insulin Secretion Using Transwell Plate

Mouse islets (100) were left standing in the bottom of each well of 24-well Transwell plates. Inserts were placed in other 24-well plates. Inserts in which a mixture of HUVEC ($1\times10^5$ cells) and hMSC ($2\times10^4$ cells) was seeded and inserts in which no cell was seeded were prepared. These inserts were placed in the 24-well plates where mouse islets had been left standing. Then, the plates were incubated in a 37° C., 5% $CO_2$ incubator overnight. Subsequently, supernatant was collected from the 24-well plates where mouse islets had been left standing, and subjected to measurement with an insulin measurement kit (Shibayagi; Cat. No. AKRIN-011H).

13. Glucose Tolerance Test In Vitro

Glucose-free RPMI1640 (Wako) was prepared as a medium for islets. By adding glucose, a low glucose medium (60 mg/100 ml) and a high glucose medium (360 mg/100 ml) were created. The low glucose medium was filled in the inserts of 24-well Transwell plate where mouse islets (100) had been left standing. The inserts were transferred to wells where a mixture of HUVECs ($1\times10^5$ cells) and hMSCs ($2\times10^4$ cells) had been seeded, followed by incubation in a 37° C., 5% $CO_2$ incubator for 1 hr. Subsequently, the medium in the inserts was exchanged with the high glucose medium, and the inserts were transferred to other wells, followed by incubation in an incubator for 1 hr. After incubation, supernatants from inserts and wells were collected and subjected to measurement with an insulin measurement kit (Shibayagi).

14. Experimental Animals

NOD/SCID mice (Sankyo Labo Service Co., Tokyo, Japan) used as transplantation animal were bred under a SPF environment with a light-dark cycle consisting of 10 hours for day and 14 hours for night. The breeding of experimental animals were entrusted to the Animal Experiment Center, Joint Research Support Section, Advanced Medical Research Center, Yokohama City University. Animal experiments were performed in accordance with the ethical guidelines stipulated by Yokohama City University.

15. Preparation of Cranial Window (CW) Mice for Continuous Observation

Preparation of CW mice was performed mainly according to the method of Yuan et al. (Document Title: Vascular permeability and microcirculation of gliomas and mammary carcinomas transplanted in rat and mouse cranial windows). For anesthetization, ketalar (Sankyo Yell Yakuhin Co., Tokyo, Japan) 90 mg/kg and xylazine (Sigma Chemical Co., St. Louis, Mo., USA) 9 mg/kg were mixed with sterilized PBS to give a dose of 200 µl per mouse and intraperitoneally injected (ketalar/xylazine mixed anesthesia). Ketalar was used according to the Narcotics Administration Law. After anesthetization, the hair on the head of NOD/SCID mice was removed with an electric clipper, and each head was sterilized with 70% ethanol. Then, the skin on the head was incised. The periosteum on the surface of the skull was removed with cotton swab. Subsequently, the skull was thinly cut with a dental microdrill (Fine Science Tools, USA) in a circular manner, and the resultant circular portion was removed carefully. Then, the dura was scraped off with tweezers. When bleeding occurred, hemostasis was performed with spongel (Astellas Co., Tokyo, Japan). After confirmation of the absence of bleeding, the surface of the brain was filled with physiological saline (Otsuka Pharmaceutical Co., Tokyo, Japan). Then, a custom-made circular slide glass 7 mm in diameter (Matsunami, Osaka, Japan) was mounted on the surface and sealed tightly with an adhesive prepared by mixing coatley plastic powder (Yoshida, Tokyo, Japan) with Aron Alpha (Toagosei Co., Tokyo, Japan) until the mixture became cementitious. One week after the preparation of CW, those mice which did not have any sign of bleeding or inflammation at the site of surgery were selected and used in the subsequent experiments.

16. Preparation of Diabetes Model Mice

Diabetes model mice were created by administering diphtheria toxin (DT) to SCID Ins-TRECK-Tg mice (kindly provided by Tokyo Metropolitan Institute for Clinical Medicine). DT 1 µg/kg was adjusted with physiological saline to give a dose of 200 µl per mouse and injected intraperitoneally. After administration, regular glucose level and body weight were measured every day at 17:00. Those mice which had a regular glucose level reading of 300 mg/dl for consecutive three days or more were used as diabetes model mice. Measurement of glucose levels was performed by Glutest neo Sensor™ (Panasonic, Tokyo) on blood samples taken from the tail vein.

17. Transplantation into CW Mice

The CW mice prepared in Section 15 above underwent transplantation after their brain surfaces were exposed by removing the glass of the cranial window. Those mice which did not have any sign of bleeding, inflammation or infection on their brain surfaces were used. After anesthetization, the area surrounding the cranial window was disinfected with 70% ethanol. The pointed end of an 18 G needle was inserted into the border line between the custom-made circular slide glass and Aron Alpha and so manipulated as to peel off the slide glass without damaging the brain surface. Thus, the brain surface was exposed. Subsequently, the brain surface was washed with physiological saline. A tissue transplant was left standing near the center of the brain surface, and the slide glass was remounted. To ensure no gap would be left, the space between the slide glass and the brain surface was filled with physiological saline and thereafter the slide glass was sealed tightly with an adhesive prepared from coatley plastic powder and Aron Alpha, in the same manner as performed at the time of preparation of CW mouse.

18. Transplantation into the Subcapsular Space of the Kidney

The diabetes model mice prepared in Section 16 above were anesthetized with isoflurane using an anesthetizing device for experimental animals (Shinano). Subsequently, the hair in the left half of the back of each mouse was removed with an electric clipper. After the shaven site was disinfected with 70% ethanol, the kidney was exposed by 1.5-2 cm incision. After exposure, the kidney was fixed and the capsule on the ventral side of the kidney was partially incised. Through the resultant opening, three-dimensional tissues prepared in Section 7 above were transplanted. After transplantation, the kidney was returned into the body. Then, the fascia and the skin were sutured.

19. Periodical Observation with Confocal Microscope of the Tissues Transplanted into CW Mice The three-dimensional tissues transplanted into CW mice in Section 17 above were observed.

Those mice which underwent transplantation were anesthetized by ketalar/xylazine mixed anesthesia in the same manner as in Section 11 above. Each mouse was fixed on a 25×60 mm micro cover glass (Matsunami) in the supine position so that the cranial window would become level. Morphological changes of the transplanted three-dimensional tissues with vascular networks were observed with a confocal microscope (LEICA TCS-SP5).

19-1 Visualization of Mouse Blood Flow

In order to visualize the blood flow from them, the host mice that underwent transplantation were anesthetized in the same manner as in Section 15 above. A fluorescent dye prepared by mixing fluorescein isothio-cyanate-dextran (Sigma, USA) with physiological saline was administered to each mouse at a rate of 100 μl per 20 g body weight from the tail vein using Myjector 29 G. Subsequently, observation was performed in the same manner as described in Section 19 above.

19-2 Visualization of Host Derived Vascular Endothelial Cells

In order to visualize host-derived blood vessels among the vascular networks constructed in the transplanted cells, mice were anesthetized in the same manner as in Section 15, followed by injection of Alexa-Flour 647 anti-mouse CD31 (Biolegend) antibody at a rate of 100 μl per 20 g body weight from the tail vein using a 29 G syringe. Subsequently, observation was performed in the same manner as described in Section 19 above.

20. Visualization of Normal Islet Tissues

The internal structure of normal islet tissues was visualized using Pdx-DsRed mice (kindly provided by Mr. Douglous Melton) and CAG-GFP mice (Japan SLC). The mice were anesthetized with isoflurane using an anesthetizing device for experimental animals. The hair on the back of each mouse was removed with an electric clipper. Then, each mouse was incised in the back by 0.5-1 cm so that the spleen was exposed to the outside, whereupon the pancreas adhering in the vicinity of the spleen became exposed. After this exposure, each mouse was held in a 10 cm dish such that the pancreas stuck to the bottom. With each mouse held in this position, 1.5% agarose gel solution cooled to 37° C. was poured into the dish to thereby fix the mouse as the pancreas remained exposed. Normal islet tissues in the fixed mouse were observed with a confocal microscope.

21. Glucose Tolerance Test In Vivo

A glucose solution 3 g/kg was adjusted with physiological saline to give a dose of 200 μl per mouse and administered by intraperitoneal injection. After administration, blood samples were taken from the tail vein every 15 min and measured for glucose levels with a Glutest neo Sensor™ (Panasonic, Tokyo).

22. Preparation of Frozen Sections

Transplanted samples were removed, washed with PBS and fixed in 4% paraformaldehyde for 1 day. Then, the sample tissue was transferred into 10% and 20% sucrose solutions, and kept there until it sank (sucrose replacement). The sinking tissue was transferred from the 20% sucrose solution to a 30% sucrose solution and kept there for 1 day for sucrose replacement. The resultant sample tissue was embedded in O.C.T. compound (Funakoshi Co.), followed by infiltration at 4° C. for 15 min. Subsequently, the sample tissue was mounted on a stand of aluminum foil floating on liquid nitrogen for freezing.

The resultant frozen block was sliced thinly into 5 μm thick sections with a cryostat (Lwica CM1950) and adhered onto a slide glass (Matsunami). Frozen sections were air-dried before use.

23. Preparation of Paraffin Sections

Transplanted samples were removed, washed with PBS and fixed in 4% PFA for 1 day. After fixation, the sample was washed with PBS three times, and dehydrated with 50, 70, 80, 90, 95 or 100% ethanol for 1 hr at each concentration. After 1 hr dehydration with 100% ethanol, the sample was dehydrated with fresh 100% ethanol for 1 day. The resultant sample was subjected to xylene replacement three times, each for 1 hr and transferred into a thermostat bath for paraffin embedding that was set at 65° C., where the sample was infiltrated with a paraffin:xylene (1:1) mixture for 1 hr and with paraffin three times, each for 2 hr. After infiltration, the sample was embedded in paraffin to prepare a paraffin block.

The thus prepared paraffin block was sliced on a microtome thinly into 5 μm thick sections, which were used as paraffin sections.

24. HE (Haematoxylin/Eosin) Staining

Frozen sections were washed with tap water for 2 min to remove the OCT compound. After washing with deionized water, tissue sections were nuclear-stained with haematoxylin (Wako) for 9 min. Subsequently, the stain solution was washed out with deionized water. The resultant tissue sections were soaked in tap water for 10 min to effect water extraction. Subsequently, after washing with deionized water, the cytoplasm of tissue sections was stained with eosin (Muto Chemical) for 10 min. After removing the excessive eosin with deionized water, tissue sections were dehydrated with a series of ethanol baths at increasing concentrations, cleared with xylene, and shielded.

Paraffin sections were infiltrated with 100% xylene three times, each for 5 min and then soaked in 100, 90, 80, 70, 60 or 50% ethanol for 3 min at each concentration to effect deparaffinization that rendered the sections hydrophilic. Subsequently, similar to the frozen sections described above, the hydrophilic sections were washed with deionized water and, thereafter, HE staining was performed.

25. Immunohistochemical Staining

After OCT removal and deparaffinization, tissue sections were each washed with PBS three times for 5 min and fixed in 4% PFA for 10 min at 4° C. Subsequently, the tissue sections were washed with PBS three times for 5 min, and blocked at 4° C. overnight with a blocking solution containing 10% normal serum of an animal used for secondary antibody preparation (goat). Then, a primary antibody diluted 200-fold with PBS was added and after reaction at 4° C. overnight, the sections were washed with PBS three times for 5 min. As the primary monoclonal antibody, a combination of anti-mouse/guinea pig insulin antibody, anti-human/mouse CD31, anti-mouse/rat CD31, anti-human/mouse collagen 4, anti-human/rabbit laminin antibody, and anti-mouse/rabbit caspase-3 antibody was used. Further, a secondary antibody diluted 500-fold with PBS was added to the tissue sections and after reaction at room temperature under shading conditions for 1 hr, the tissue sections were washed with PBS three times for 5 min, shielded with a mounting medium containing 4',6-diamidino-2-phenylindole dihydrochloride (DAPI; Invitrogen), and observed and photographed with a fluorescence microscope. As the secondary antibody (Molecular Probe), a combination of the following antibodies was used: Alexa 488-, 555-labeled goat anti-rabbit $IgG_{(H+L)}$ antibody, Alexa 488-, 555-, 647-labeled goat anti-rat $IgG_{(H+L)}$ antibody, Alexa 488-, 555-labeled goat anti-guinea pig $IgG_{(H+L)}$ antibody, and Alexa 488-, 555-, 647-labeled goat anti-mouse $IgG_{(H+L)}$ antibody.

26. Immunohistological Analysis by Whole Mount Method

Vascularized islets as generated were recovered and fixed in a 4% PFA solution for 1 day, followed by washing with PBS three times for 10 min. After fixation, the islets were placed in a 0.1% Triton-PBS solution containing 3% BSA and blocked at room temperature for 1 hr. After blocking, the islets were washed with a 0.1% Triton-PBS solution three times for 10 min. A transplant was placed in a solution of primary antibody diluted with a 0.1% Triton-PBS solution and reaction was performed at 4° C. for 1 day. After the reaction, the transplant was washed with a 0.1% Triton-PBS solution three times for 10 min and then placed in a solution of secondary antibody diluted with a 0.1% Triton-PBS solution, followed by reaction at room temperature for 4 hr. After the reaction, the transplant was washed with a 0.1% Triton-PBS solution three times for 10 min. A mounting medium containing DAPI was added to the transplant, which was then observed with a confocal microscope.

[Results]

Figure 1B:
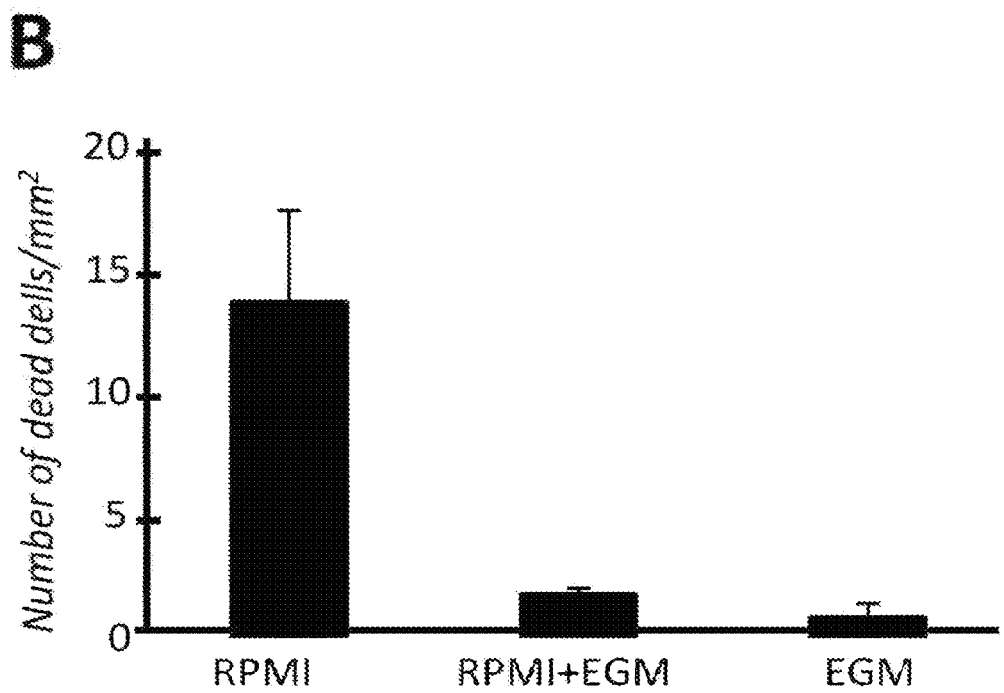
FIG. 1B This figure shows the integration of vascular networks to islet tissues.
B) Quantification data for A).

1. Generation of Three-Dimensional Tissues by Coculturing Mouse Islets, Vascular Endothelial Cells and Mesenchymal Stem Cells Media were validated using the survival rate of islet cells as an indicator (FIG. 1A). At 72 hours of culture, dead cell numbers per islet area under respective conditions were 14 cells/mm$^2$ in RPMI1640 medium; 1.8 cells/mm$^2$ in the mixed medium of RPMI1640 and the endothelial cell medium; and 0.8 cells/mm$^2$ in the endothelial cell medium (FIG. 1B).

Figure 1C:
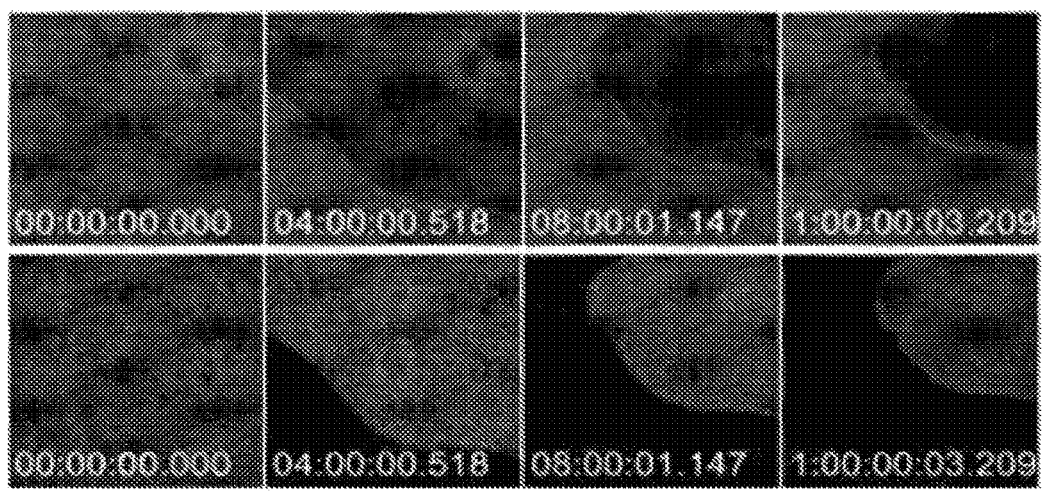
FIG. 1C This figure shows the integration of vascular networks to islet tissues.
C) Time-lapse imaging of three-dimensional tissue constituting processes using mouse islets (colorless), vascular endothelial cells (green) and mesenchymal stem cells (red).
Figure 1D:
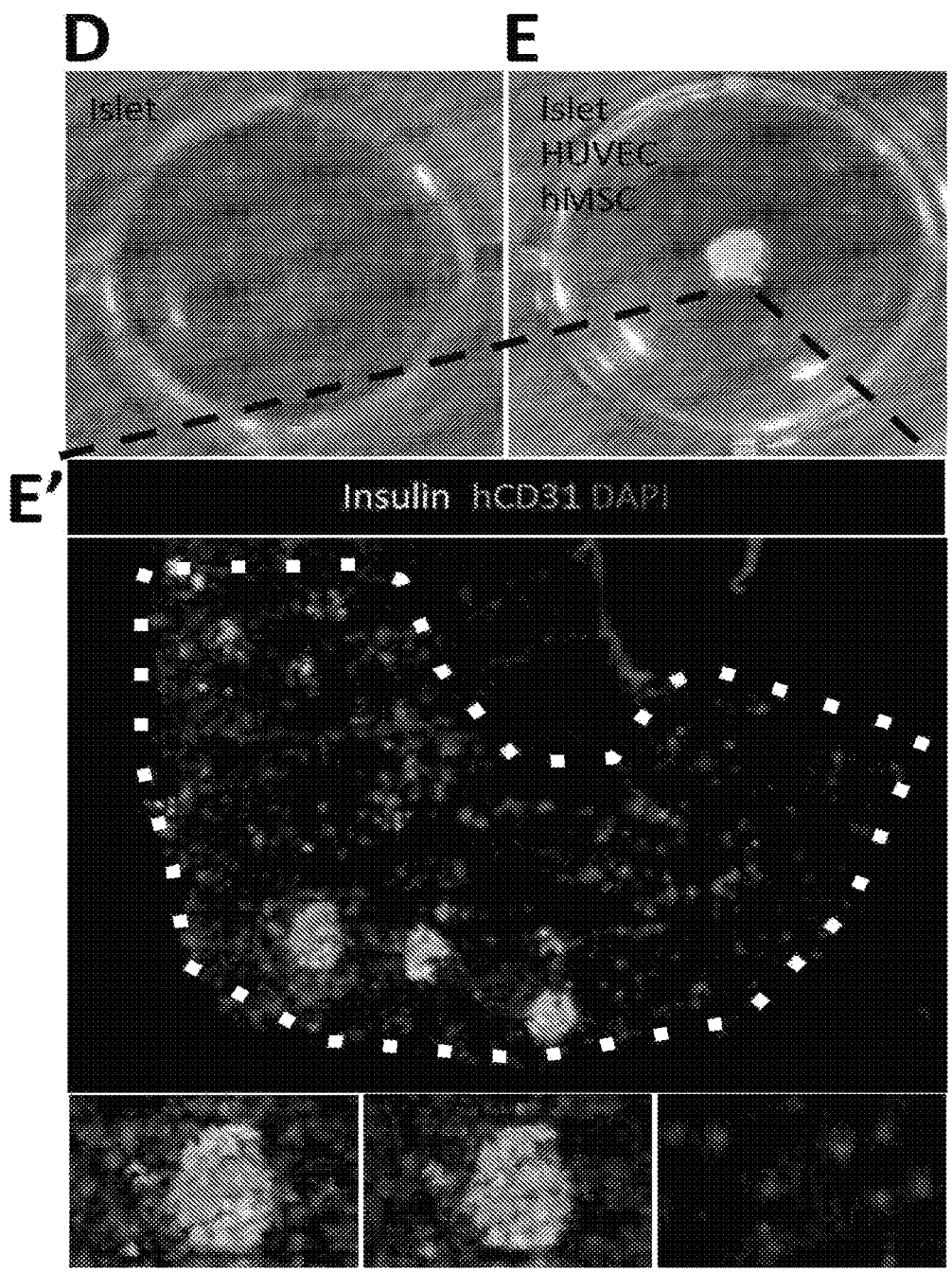
FIG. 1DE This figure shows the integration of vascular networks to islet tissues.
D) Mouse islets at 24 hours of culture.
E) Mouse islets, vascular endothelial cells and mesenchymal stem cells at 24 hours of coculture.
E') Immunohistological analysis of the three-dimensional tissue generated in E) (green: insulin, red: human CD31).

Culture was performed as described in Section 7 of Methods above. Immediately after the beginning of culture, cells were scattered around islets and no three-dimensional tissues visible with eyes were recognized. At 4 hours of culture, however, interactions between cells started, and scattered cells began to gather closely. At 8 hours of culture, cells so aggregated as to cover islets and gradually constituted a three-dimensional structure. Finally, at 24 hours of culture, self-organization progressed further and a vascularized three-dimensional tissue was constituted (FIG. 1C, upper panel; FIG. 1E). On the other hand, when coculture was not performed but islets alone were cultured, neither vascularization nor formation of three-dimensional tissues was recognized (FIG. 1D).

Figure 2A:
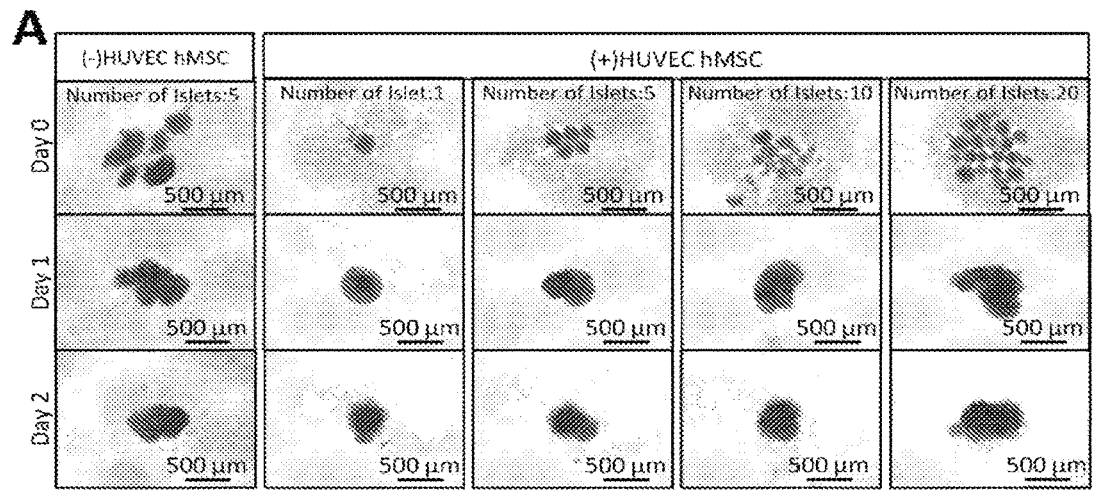
FIG. 2A This figure shows preparation of vascularized islet fragments.
A) Autonomous formation of vascularized islet fragments using a culture plate of such a shape that cells gather in the bottom (vascularized tissues are formed even when the number of mouse islets is changed).
Figure 2B:
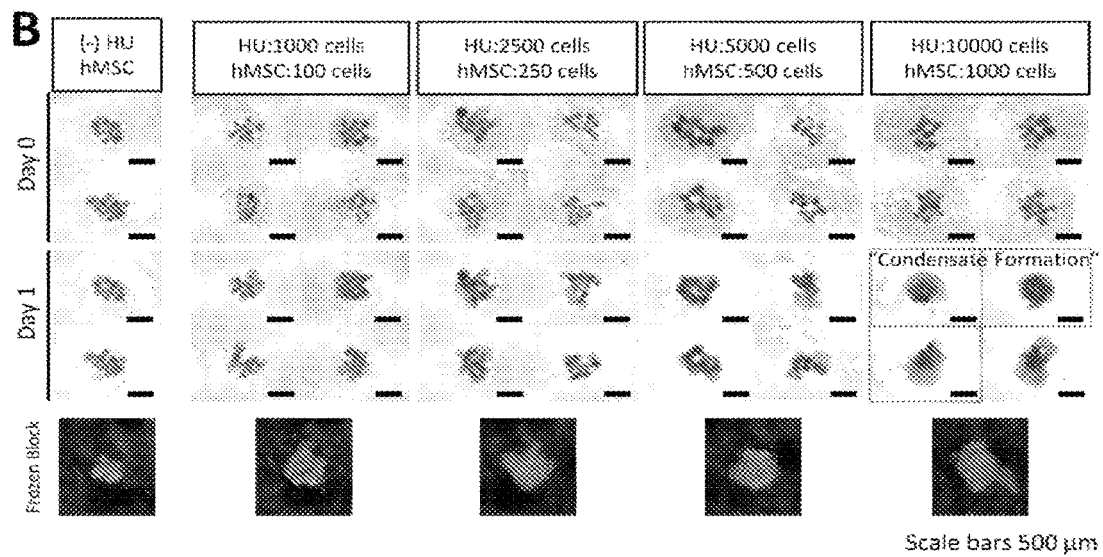
FIG. 2B This figure shows preparation of vascularized islet fragments.
B) Reviewing the conditions of vascular endothelial cell number and mesenchymal stem cell number.
Figure 2C:
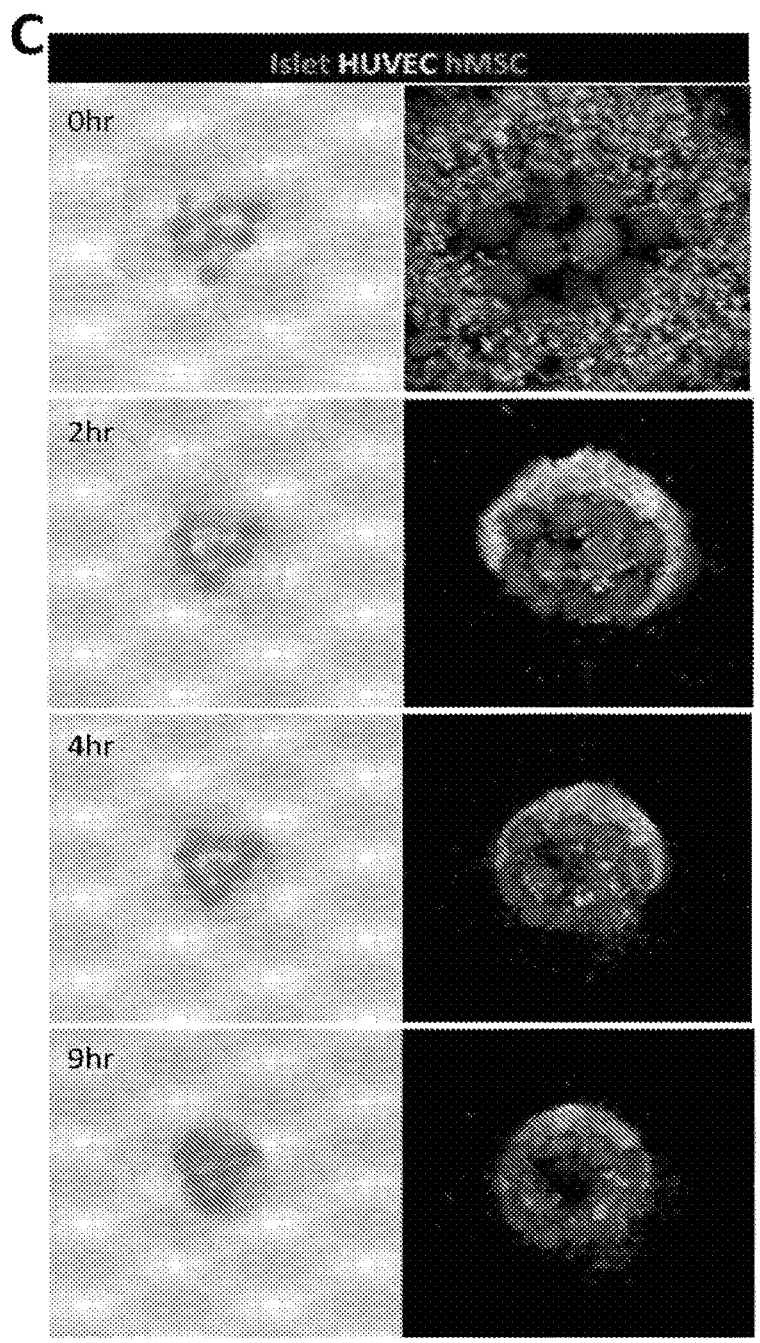
FIG. 2C This figure shows preparation of vascularized islet fragments.
C) Time-lapse imaging of the processes of formation of vascularized islet fragments (changes in cell morphology caused by coculture; mouse islets: blue; vascular endothelial cells: green; mesenchymal stem cells: red).
Figure 2D:
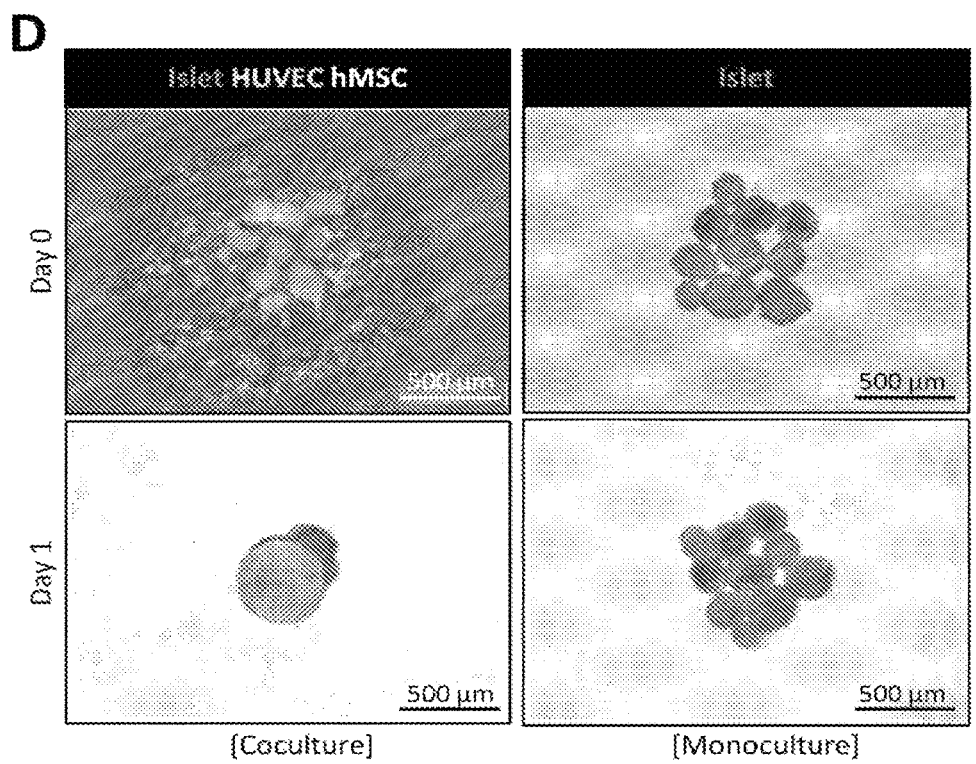
FIG. 2D This figure shows preparation of vascularized islet fragments.
D) Prepared vascularized islet fragments; mouse islets (red), vascular endothelial cells (green) and mesenchymal stem cells (colorless).
Figure 2E:
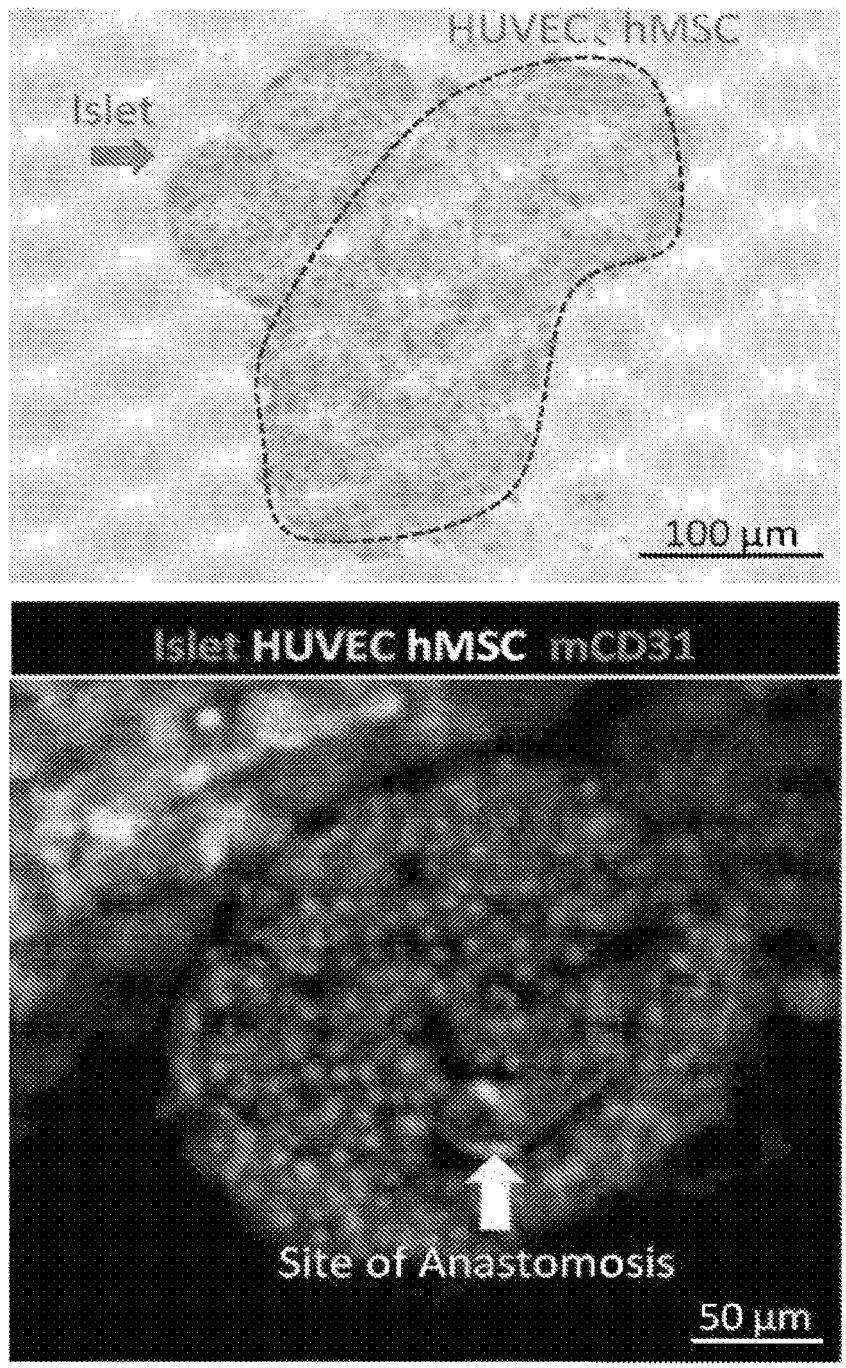
FIG. 2E This figure shows preparation of vascularized islet fragments.
E) Histological analysis of vascularized islet fragments; mouse islets (red), vascular endothelial cells (green), mesenchymal stem cells (colorless) and mouse CD31 (blue).

Further, by culturing islets as described in Section 8 of Methods above, an attempt was made to decrease the size of vascularized three-dimensional tissues in a culture plate (substrate?) of such a shape that cells/tissues would gather in the bottom (FIG. 2A-FIG. 2E). When 1, 5, 10 and 20 mouse islet tissues were cocultured with HUVECs and MSCs, three-dimensional tissues were formed at 24 hours of culture and their morphology was retained even at 48 hours of culture (FIG. 2A). Further, minimum cell numbers of HUVECs and MSCs required for constitution of a vascularized three-dimensional tissue were examined (FIG. 2B). When 10 mouse islets were cocultured with $1.0 \times 10^4$ HUVECs and $1.0 \times 10^3$ MSCs, scattered cells began to aggregate due to the intercellular adhesion at 2 hours of culture. At 9 hours of culture in an advanced stage, cells so aggregated as to cover islets until they constituted a three-dimensional tissue (FIG. 2C, left panel). In order to track morphological changes in cells, coculture experiments were performed using fluorescence-labeled mouse islets and various kinds of cells (FIG. 1A, lower panel; FIG. 2C, right panel; FIG. 2D). Briefly, islets isolated from Pdx-DsRed mice (FIG. 1A; 2D: red; 2C: blue), HUVECs into which green fluorescent protein (GFP) had been introduced (FIG. 1A, 2C, 2D: green) and MSC (FIG. 2C: red) were cocultured, followed by observation of cell morphology under a confocal microscope. Immediately after the beginning of culture, HUVECs were found to be scattered evenly around islets. Further, HUVECs were shown not only to adhere directly to islet tissues; some of them were also shown to connect to vascular endothelial cells inside the islets (FIG. 2E).

From the foregoing, it was revealed that a vascularized three-dimensional tissue was autonomously generated by coculturing the three types of cells, i.e., mouse islet, HUVEC and MSC, under appropriate conditions.

Figure 1F:
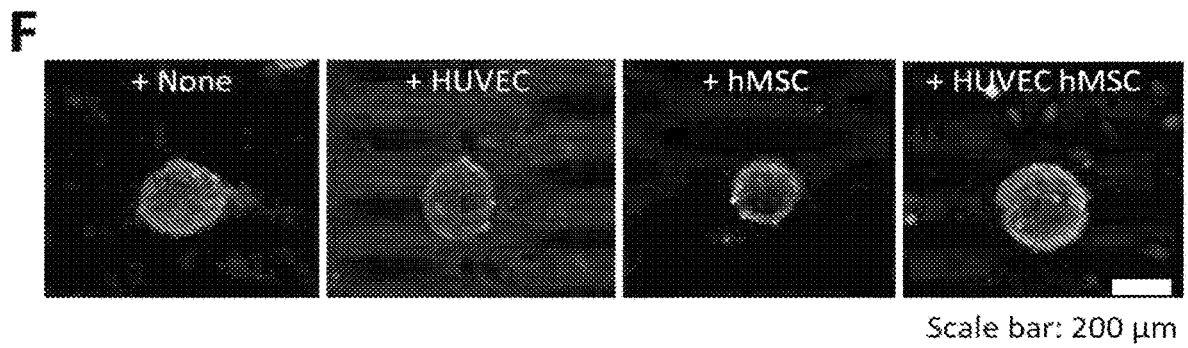
FIG. 1F This figure shows the integration of vascular networks to islet tissues.
F) Determination of survival or death of mouse islet cells using Live/Dead™ Cell Imaging Kit (green: viable cells, red: dead cells).
Figure 1G:
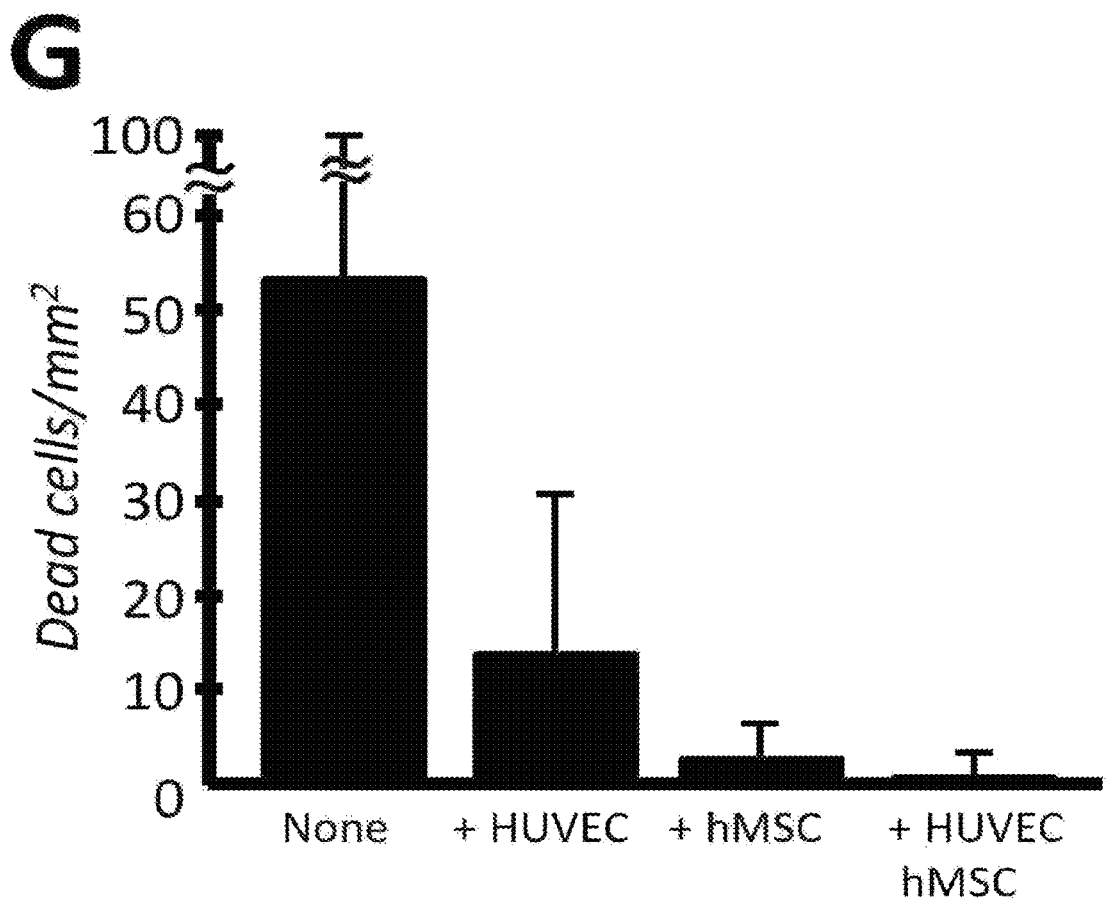
FIG. 1G This figure shows the integration of vascular networks to islet tissues.
G) Quantification data for F).

2. Improvement of the Function of Mouse Islet by Coculture with Vascular Endothelial Cells and Mesenchymal Stem Cells Mouse islets were cultured as described in Section 10 of Methods above and their survival rates under various conditions were compared (FIG. 1F, viable cell: green; dead cell: red). At 24 hours of culture, dead cell numbers per islet area under the respective conditions were 53 cells/mm$^2$ in monoculture of islets alone, 14 cells/mm$^2$ in coculture with HUVECs, 2 cells/mm$^2$ in coculture with MSCs, and 0.1 cells/mm$^2$ in coculture with HUVECs and MSCs (FIG. 1G). From these results, it was shown that the survival rate of mouse islet cells was improved by coculturing with HUVECs and MSCs.

Figure 1H:
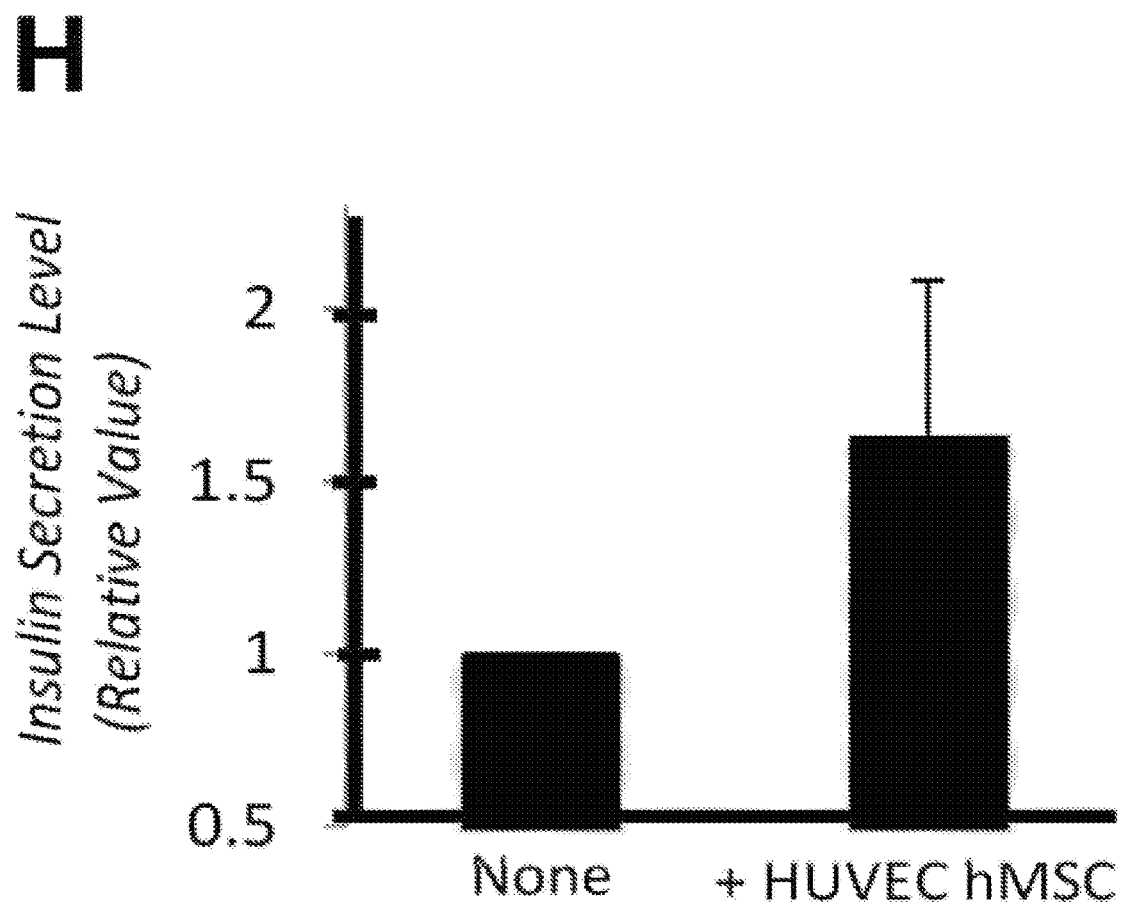
FIG. 1H This figure shows the integration of vascular networks to islet tissues.
H) Increase of insulin concentration released from cocultured mouse islets.
Figure 1I:
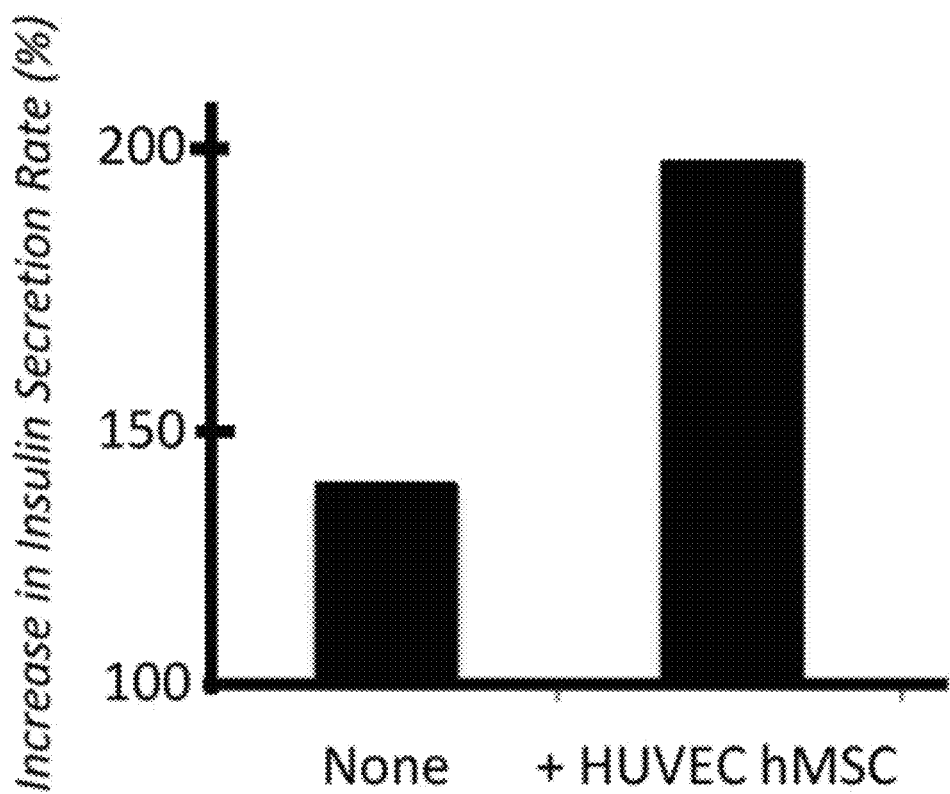
FIG. 1I This figure shows the integration of vascular networks to islet tissues.
I) Glucose tolerance test in vitro.

Further, culture was performed as described in Section 12 of Methods above and insulin levels secreted from the mouse islets were measured (FIG. 1H). At 24 hours of culture, the insulin secretion from the mouse islets cocultured with HUVECs and MSCs was greater than that from the monocultured mouse islets. When a glucose tolerance test was performed in vitro, insulin secretion increased 1.37-fold in the islet monoculture group and 1.97-fold in the coculture group (FIG. 1I). In order to specify the group of molecules contributing to such improvement of islet function, changes in gene expressions before and after coculture with HUVCs and MSCs were analyzed comprehensively by microarray analysis. As a result, 214 candidate genes were extracted as genes whose expression was enhanced by coculture by a factor of two or more. It was therefore suggested that coculturing mouse islets with HUVECs and MSCs initiated changes in the expression of various genes, leading to an improvement of the function of the mouse islets.

3. Periodical Observation of Vascularized Islet Transplantation

Figure 3C:
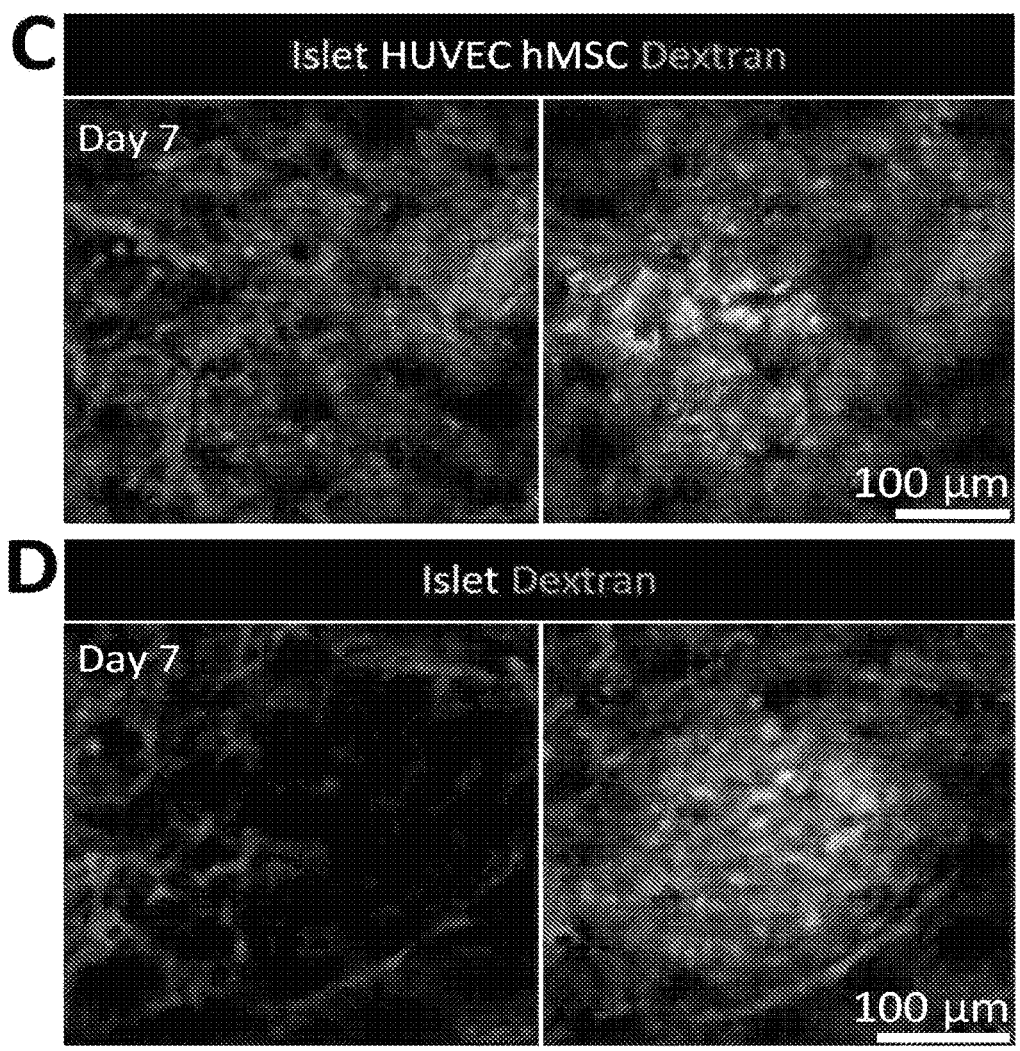
FIG. 3CD This figure shows validation of function upon transplantation of vascularized tissue.
C) Blood perfusion into vascularized islets; mouse islets (green), vascular endothelial cells (colorless), mesenchymal stem cells (colorless), dextran (red).
D) Blood perfusion around transplanted islets; mouse islets (green), vascular endothelial cells (colorless), mesenchymal stem cells (colorless), dextran (red).
Figure 3E:
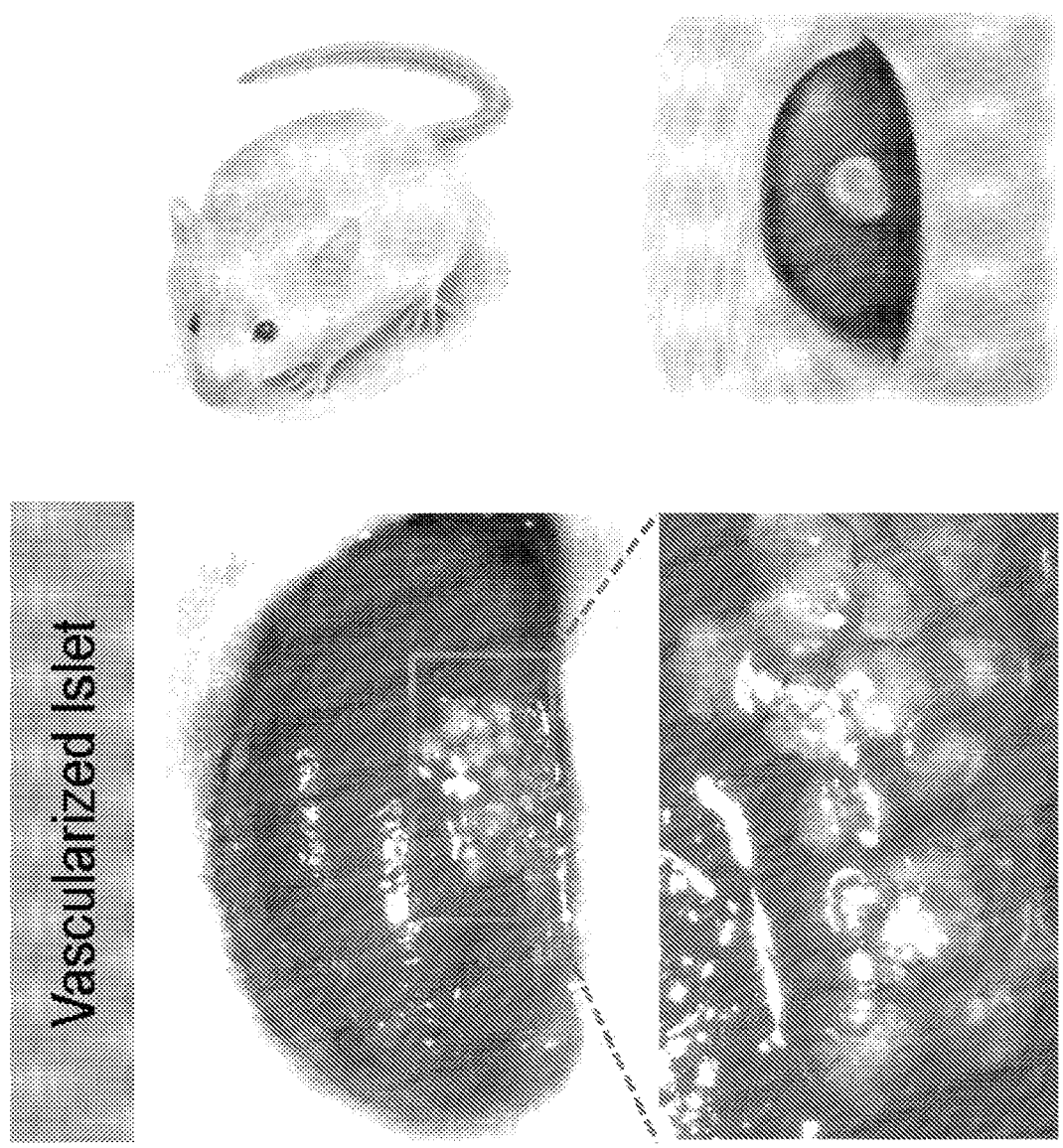
FIG. 3E This figure shows validation of function upon transplantation of vascularized tissue.
E) Transplantation of vascularized islets into the subcapsular space of the kidney using diabetes model mice; blood glucose transition.
Figure 3F:
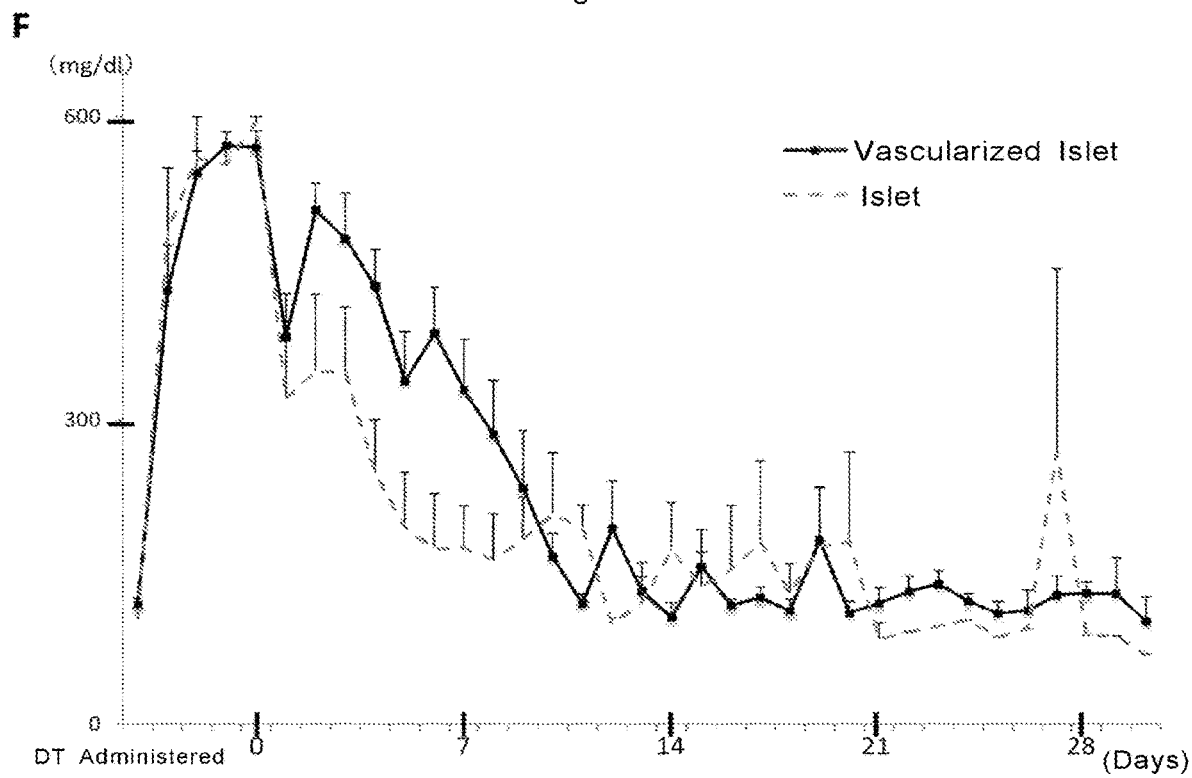
FIG. 3F This figure shows validation of function upon transplantation of vascularized tissue.
F) Blood glucose transition in diabetes model mice.
Figure 3G:
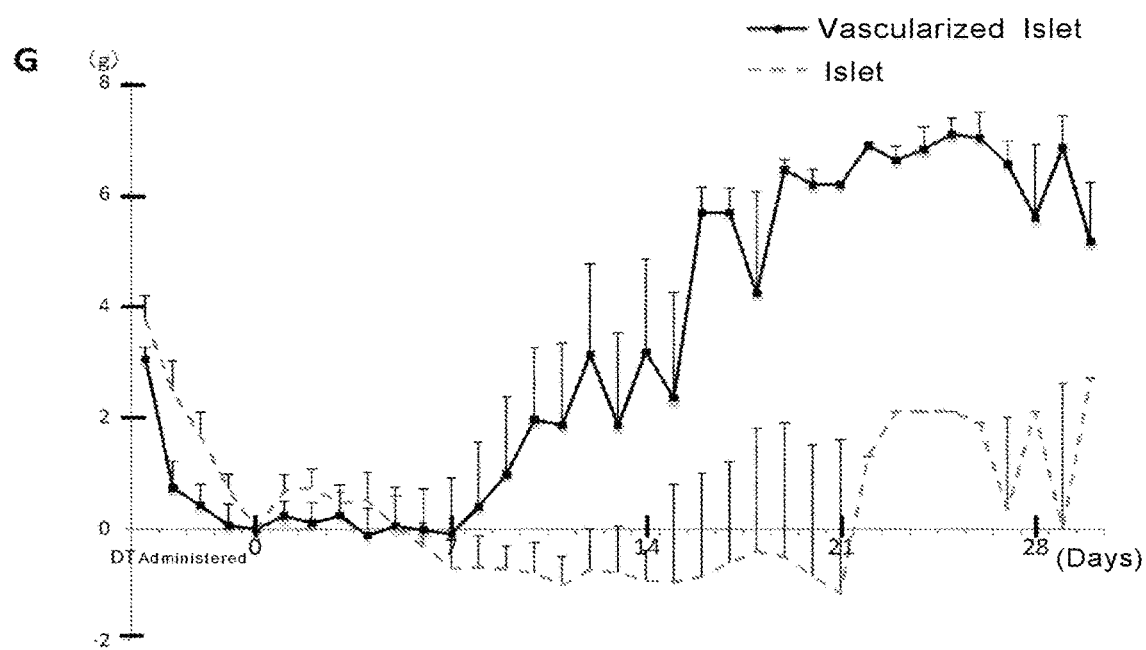
FIG. 3G This figure shows validation of function upon transplantation of vascularized tissue.
G) Body weight transition in diabetes model mice.
Figure 3H:
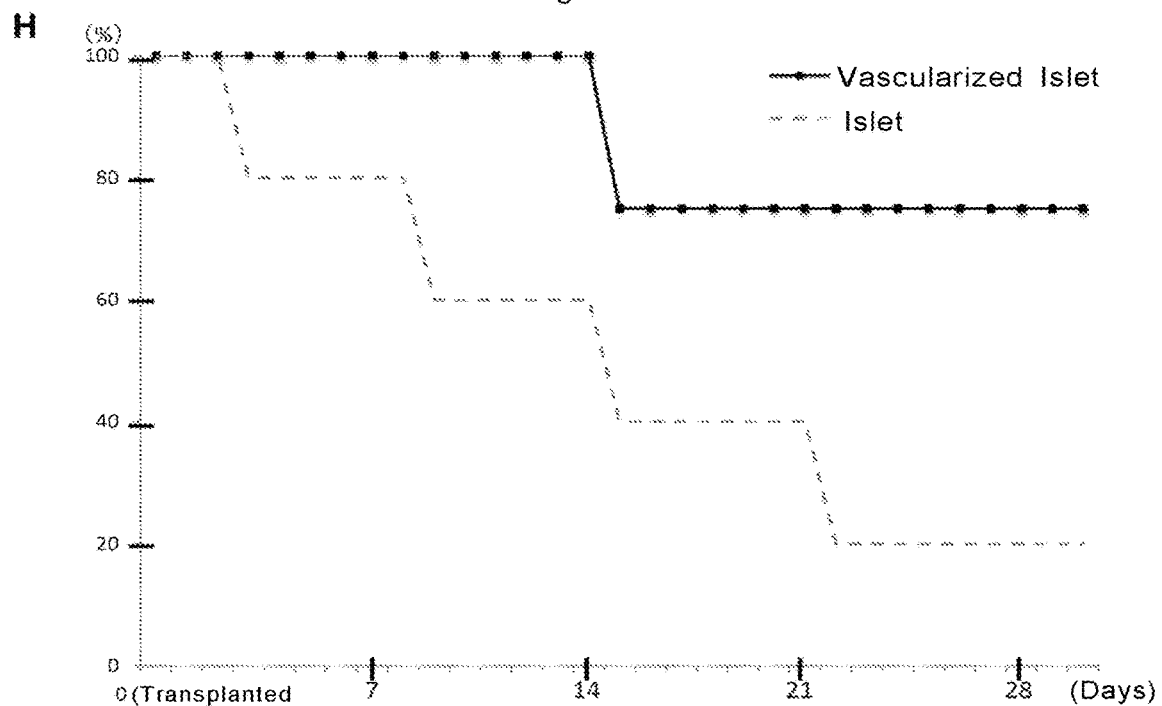
FIG. 3H This figure shows validation of function upon transplantation of vascularized tissue.
H) Survival ratios in diabetes model mice.
Figure 3I:
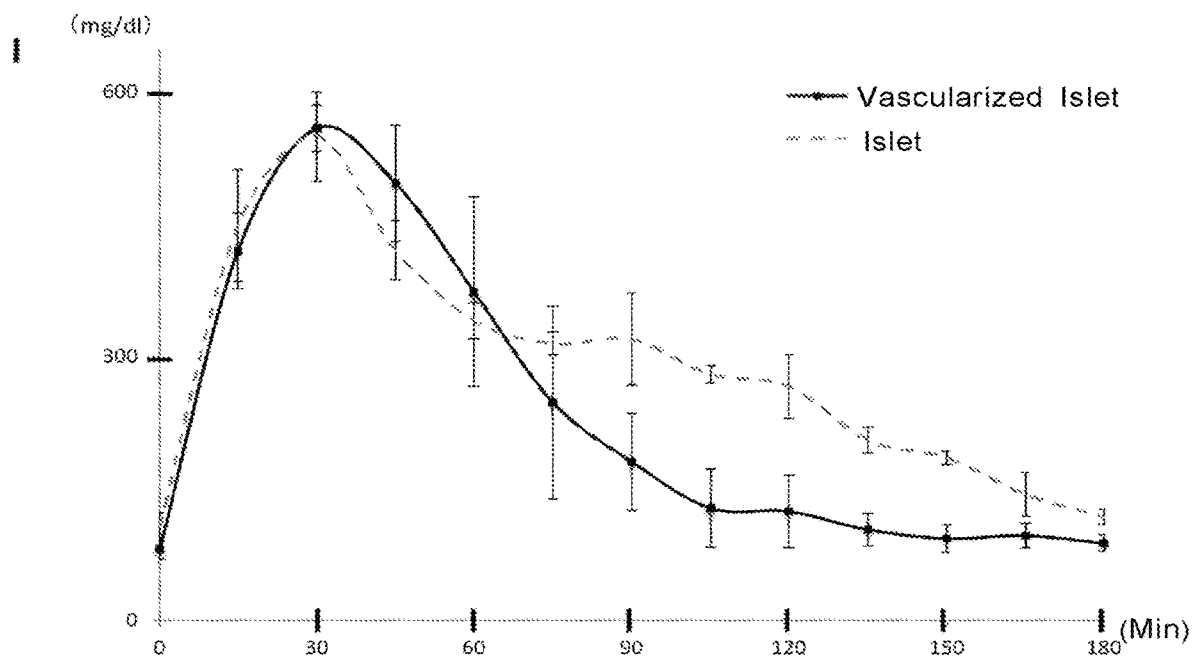
FIG. 3I This figure shows validation of function upon transplantation of vascularized tissue.
I) In vivo glucose tolerance test.
Figure 3J:
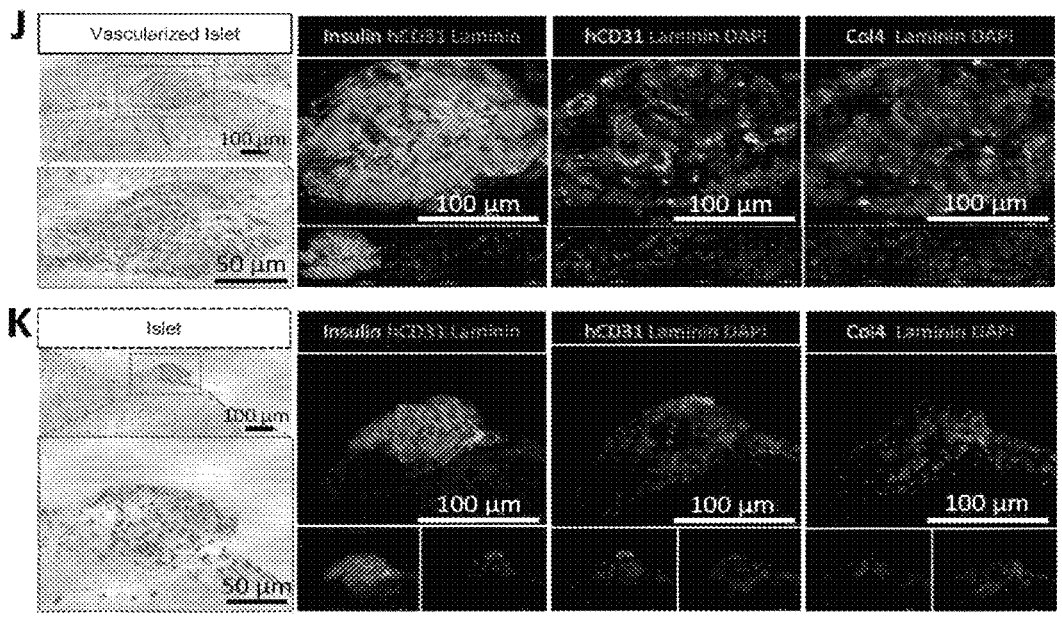
FIG. 3JK This figure shows validation of function upon transplantation of vascularized tissue.
J) Histological analysis of vascularized islets transplanted into CW.
K) Histological analysis of islets transplanted into CW.
Figure 3L:
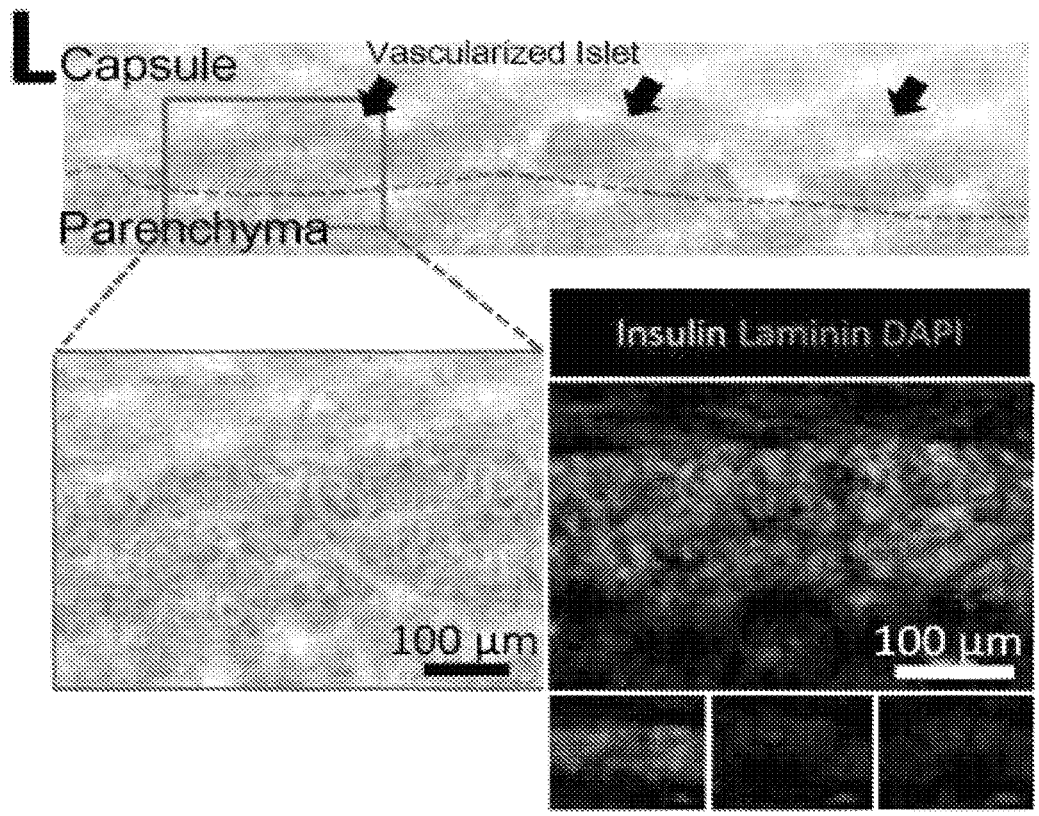
FIG. 3L This figure shows validation of function upon transplantation of vascularized tissue.
L) Histological analysis of vascularized islets transplanted into the subcapsular space of the kidney; insulin (green), laminin (red), DAPI (blue).
Figure 3M:
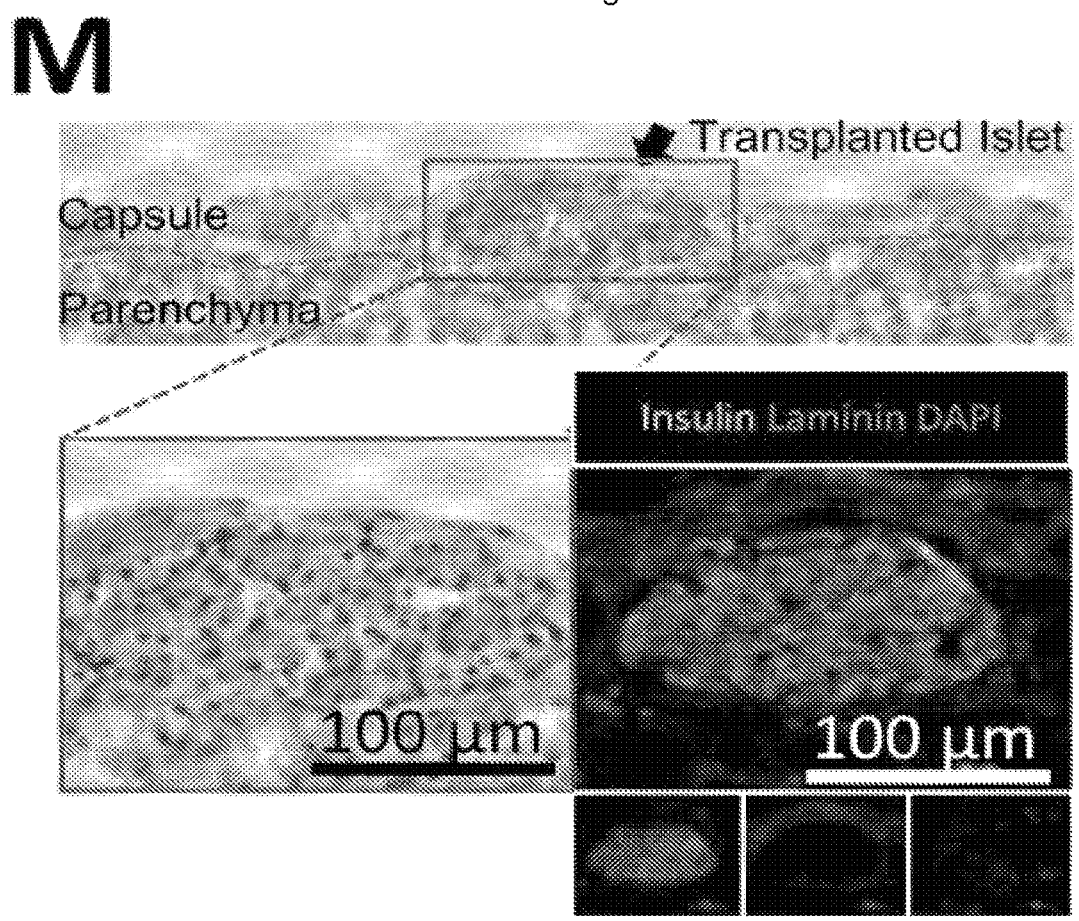
FIG. 3M This figure shows validation of function upon transplantation of vascularized tissue.
M) Histological analysis of islets transplanted into the subcapsular space of the kidney; insulin (green), laminin (red), DAPI (blue).

The vascularized islet generated in Section 1 of Results above was transplanted into mice and morphological changes in tissues were tracked (FIG. 3AB, FIG. 3CD, FIG. 3E, FIG. 3F, FIG. 3G, FIG. 3H, FIG. 3I, FIG. 3JK, FIG. 3L, FIG. 3M). Further, in order to examine the necessity of vascularization for generating tissues, mouse islets alone were transplanted into mice for comparison. Vascularized islets were transplanted into cranial window (CW) mice as described in Section 17 of Methods, and morphological changes were tracked as described in Section 19 of Methods.

After transplantation of mouse islets alone, no macroscopic changes were observed in mouse heads until day 2 post-transplantation. Also, no blood perfusion into transplanted islets was observed. As time passed after transplantation, viable islets decreased (FIG. 3AB). When fluorescence labeling was used to observe changes in cell morphology, there were no changes, either, but the number of islets gradually decreased. Further, when blood flow was visualized, no blood perfusion into the inside of islets occurred at day 7 post-transplantation (FIG. 3D, islet: green; blood flow: red). However, in the mouse heads transplanted with vascularized islets, blood perfusion to all over the transplantation site occurred at day 2 post-transplantation (FIG. 3AB). Further, according to an observation with a confocal microscope, blood perfusion into the inside of islets was confirmed at day 7 post-transplantation (FIG. 3CD, islet: green; blood flow: red).

It was shown by these results that transplantation of vascularized islets induced early resumption of blood flow into the inside of the transplanted islets and improved the islet survival rate after transplantation.

4. Validation of Therapeutic Effect on Diabetes by Transplantation of Vascularized Islets Forty vascularized islets cocultured under the condition of 5 islets were transplanted into the subcapsular space of the kidney of diabetes model mice and evaluated for their therapeutic effects (FIG. 3E). Decrease in glucose level was seen at day 1 post-transplantation, and normal glucose level was kept stably retained at week 2 post-transplantation and thereafter (FIG. 3F). Further, a great increase in body weight was seen (FIG. 3G) and survival rate improved (FIG. 3H). The results of a glucose tolerance test in vivo revealed that the diabetes model mice showed a insulin secretion response which was almost equal to that of normal mice (FIG. 3I).

As described above, therapeutic effects on diabetes were shown by transplanting vascularized islets.

5. Histological Analysis of Vascularized Islets

Vascularized islets at day 1 of coculture were analyzed histologically and immunohistologically. When HE staining was performed, islet tissues were observed that had no central necrosis and which adjoined HUVECs and MSCs (FIG. 2E, upper panel). Further, immunostaining was performed as follows (FIG. 1DE item E'; 2E, lower panel). Briefly, islets were stained with insulin antibodies (FIG. 1DE item E': green; 2E: red); HUVECs were stained with human vascular endothelial cell antibodies (FIG. 1DE item E': red; 2E: green); and mouse blood vessels were stained with mouse vascular endothelial cell antibodies (FIG. 2E: blue). The presence of HUVECs was confirmed in the inside of insulin-positive islets, and HUVECs and mouse blood vessels were connected together.

Further, vascularized islets (FIG. 3J) and islets (FIG. 3K) at day 30 post-transplantation into cranial windows were individually analyzed histologically and immunohistologically. As a result of HE staining, islets engrafting onto the brain tissue were confirmed. As a result of immunostaining, it was found that human vascular endothelial cells were present at insulin-positive sites in the vascularized islets, and that such human vascular endothelial cells were stable human blood vessels that would secrete laminin and collagen IV (extracellular matrices). However, when islets alone were transplanted, no vascular endothelial cells were found inside the islets.

Further, vascularized islets (FIG. 3L) and islets (FIG. 3M) at day 28 post-transplantation into the subcapsular space of the kidney were individually analyzed histologically and immunohistologically. As a result of HE staining, islets present between the renal parenchyma and the capsule were confirmed (FIG. 3L, lower left panel; FIG. 3M, lower left panel). Further, immunostaining was performed to stain islets (green) with an insulin antibody and vascular endothelial cells (red) with a laminin antibody (FIG. 3L, lower right panel; FIG. 3M, lower right panel). In the vascularized inlets, expression of laminin-positive vascular endothelial cells was confirmed inside insulin-positive islets. However, in those islets which were transplanted with inlets alone, no vascular endothelial cells were observed.

As described above, it was shown from histological and immunohistological viewpoints that the vascularized islets were islet tissues associated with human blood vessels.

[Example 2] Integration of Vascular Networks for Renal Glomeruli

[Methods]
1. Isolation of Mouse Glomeruli

C57BL/6-Tg mice (Japan SLC, Inc.) anesthetized with diethyl ether (Wako) were laparotomized after disinfection of the abdomen with 70% ethanol. The kidney was cut out and the capsule was removed therefrom. After washing with physiological saline, the kidney was cut in round slices with a scalpel. The renal pelvis and the medulla were removed with scissors, and the cortex was recovered. The recovered cortex was minced on ice and filtered with a 100 µm mesh cell strainer while adding Hanks' buffer (HBSS, Gibco) containing 0.1% albumin from bovine serum (BSA, Sigma) little by little. The flow-through was filtered with a 70 µm mesh cell strainer, and finally the flow-through was filtered with a 40 µm mesh cell strainer. The cell mass retained on the 40 µm mesh cell strainer was recovered with 0.1% BSA-containing Hanks' buffer. The thus recovered material was filtered with a 100 µm mesh cell strainer.

2. Selection of Mouse Glomeruli

When the mouse glomeruli isolated in Section 1 of Methods above were observed under a stereomicroscope, spherical mouse glomeruli (diameter: 50-100 µm) could be confirmed. These glomeruli were recovered and transferred to a medium for glomeruli with a Pipetman.

3. Primary Culture of Mouse Glomeruli

Mouse glomeruli were cultured using RPMI1640 (Wako) supplemented with 20% fetal bovine serum (BWT Lot. S-1560), 100 µg/ml penicillin/streptomycin (Gibco) and Insulin-Transferrin-SeleniumX (Gibco) in a 37° C., 5% $CO_2$ incubator.

4. Cell Culture

Normal human umbilical vein endothelial cells (HUVECs) (Lonza CC-2517) were cultured using a medium prepared especially for culturing HUVEC [EGM™ BulletKit™ (Lonza CC-4133)] within a guaranteed passage number (5 passages). Human mesenchymal stem cells (hMSCs) (Lonza PT-2501) were cultured using a medium prepared especially for culturing hMSCs [MSCGM™ BulletKit™ (Lonza PT3001)] within a guaranteed passage number (5 passages). Both HUVECs and hMSCs were cultured in a 37° C., 5% $CO_2$ incubator.

5. Preparation of Three-Dimensional Tissues Having a Vascular System

For the purpose of chronological observation, 1, 5 and 10 mouse glomeruli/well were left standing in each well of PrimeSurface™ 96-Well U Plate (Sumitomo Bakelite) preliminarily filled with a medium for glomeruli, and $5 \times 10^4$ HUVECs and $5 \times 10^3$ hMSCs were seeded in each well. Subsequently, the plate was incubated in a 37° C. incubator for one day. Further, 100 mouse glomeruli/well were left standing in each well of a 24-well plate, and $2 \times 10^6$ HUVECs and $2 \times 10^5$ hMSCs were seeded in each well.

6. Chronological Observation Using Stereomicroscope

Coculture was performed for tracking chronological changes with a stereomicroscope. Briefly, 20 mouse glomeruli/well were left standing in each well of a 24-well plate, and $2 \times 10^6$ HUVECs and $2 \times 10^5$ hMSCs were seeded in each well. After seeding, the plate was set in a stereomicroscope (Leica DFC300FX) and morphological changes caused by coculture were observed.

7. Experimental Animals

NOD/SCID mice (Sankyo Labo Service Co., Tokyo, Japan) used as transplantation animal were bred under a SPF environment with a light-dark cycle consisting of 10 hours for day and 14 hours for night. The breeding of experimental animals were entrusted to the Animal Experiment Center, Joint Research Support Section, Advanced Medical Research Center, Yokohama City University. Animal experiments were performed in accordance with the ethical guidelines stipulated by Yokohama City University.

8. Transplantation into CW Mice

The CW mice prepared underwent transplantation after their brain surfaces were exposed by removing the glass of the cranial window. Those mice which did not have any sign of bleeding, inflammation or infection on their brain surfaces were used. After anesthetization, the area surrounding the cranial window was disinfected with 70% ethanol. The pointed end of an 18 G needle was inserted into the border between the custom-made circular slide glass and Aron Alpha and so manipulated to peel off the slide glass without damaging the brain surface. Thus, the brain surface was exposed. Subsequently, the brain surface was washed with physiological saline. A tissue transplant was left standing near the center of the brain surface, and the custom-made slide glass was remounted. To ensure no gap would be left, the space between the slide glass and the brain surface was filled with physiological saline and thereafter the slide glass was sealed tightly with an adhesive prepared from coatley plastic powder and Aron Alpha, in the same manner as performed at the time of preparation of CW mice.

9. Periodical Observation with Confocal Microscope of the Tissues Transplanted into CW Mice The three-dimensional tissues transplanted into the CW mice in the preceding Section 8 were observed.

Those mice which underwent transplantation were anesthetized by ketalar/xylazine mixed anesthesia in the same manner as in Section 11 above. Each mouse was fixed on a 25×60 mm micro cover glass (Matsunami) in the supine position so that the cranial window would become level. Morphological changes of the transplanted three-dimensional tissues with vascular networks were observed with a confocal microscope (LEICA TCS-SP5).

[Results]

Figure 4:
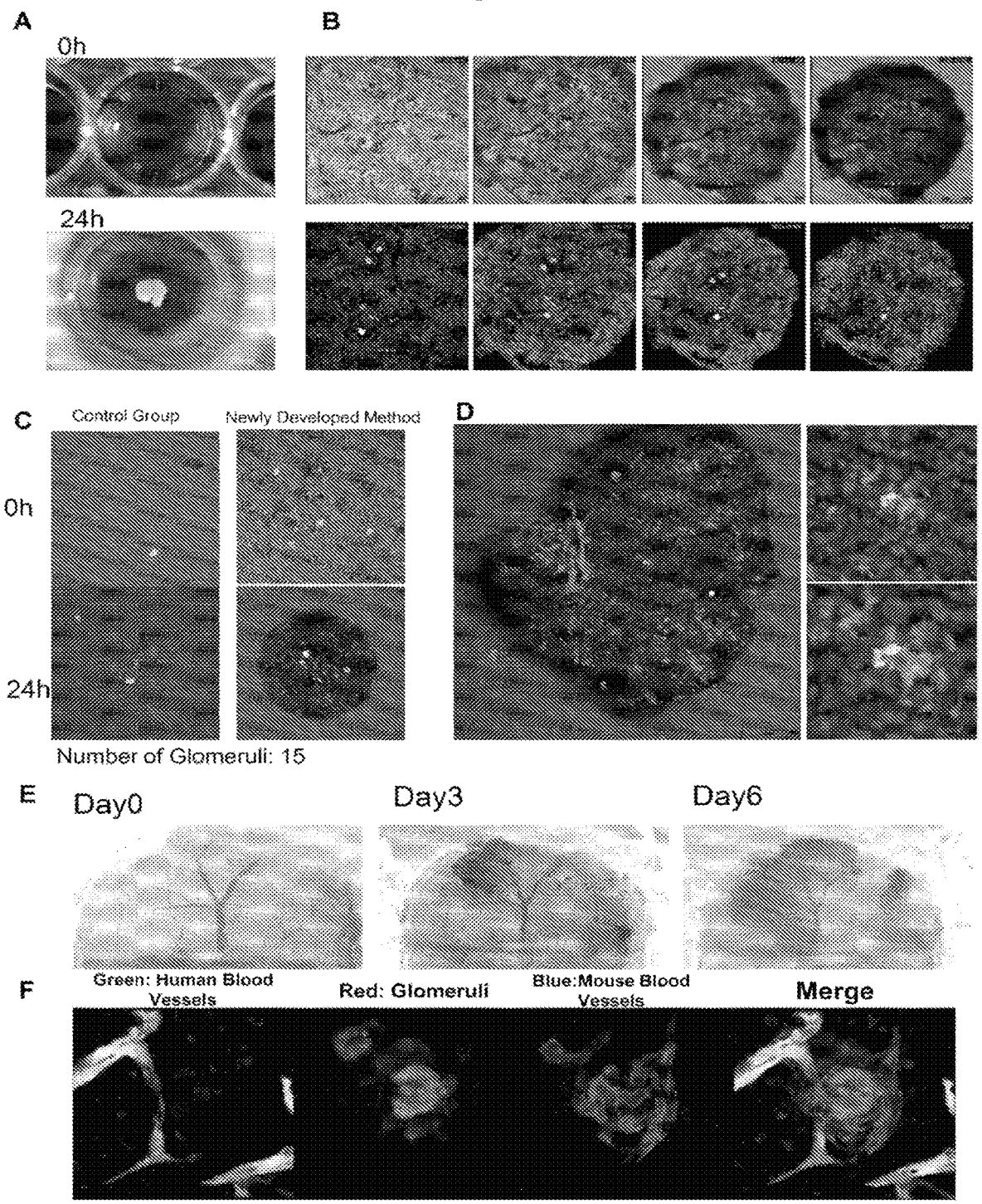
FIG. 4 This figure shows the integration of vascular networks to renal glomeruli.
A) Autonomous formation of a three-dimensional tissue derived from mouse renal glomeruli, vascular endothelial cells and mesenchymal stem cells using a 24-well dish.
B) Autonomous formation of a three-dimensional tissue derived from mouse renal glomeruli, vascular endothelial cells and mesenchymal stem cells using a culture plate (substrate?) of such a shape that cells gather in the bottom (time-lapse imaging of the three-dimensional tissue using mouse renal glomeruli (green), vascular endothelial cells (red) and mesenchymal stem cells (blue)).
C) Macroscopic image of vascularized three-dimensional mouse renal glomerular tissue at 24 hours of culture using a 24-well dish.
D) Macroscopic image of vascularized three-dimensional mouse renal glomerular tissue at 24 hours of culture using a 96-well dish.
E) Confirmation of vascularization and engraftment at the site of transplantation of vascularized renal glomeruli.
F) Live imaging of the site of transplantation of vascularized renal glomeruli (mouse renal glomeruli (red), human vascular endothelial cells (green), mouse vascular endothelial cells (blue)).

1. Generation of Vascularized Three-Dimensional Tissues by Coculture of Mouse Glomeruli, Vascular Endothelial Cells and Mesenchymal Stem Cells Culture was performed as described in Section 6 of Methods above. Immediately after the beginning of culture, cells were scattered around glomeruli and no three-dimensional tissues visible with eyes were recognized. At 4 hours of culture, however, interactions between cells started, and scattered cells began to gather closely. At 8 hours of culture in an advanced stage, cells so aggregated as to cover glomeruli and gradually constituted a three-dimensional structure. Finally, at 24 hours of culture, self-organization progressed further and a vascularized three-dimensional tissue was constituted (FIG. 4, panel A, FIG. 4, panel B). On the other hand, when coculture was not performed but glomeruli alone were cultured, neither vascularization nor formation of three-dimensional tissues was recognized (FIG. 4, panel C).

Further, by culturing glomeruli as described in Section 5 of Methods above, an attempt was made to decrease the size of vascularized three-dimensional tissues in a culture plate (substrate?) of such a shape that cells/tissues would gather in the bottom (FIG. 4, panel C). When 5, 10 and 15 mouse glomeruli were individually cocultured with HUVECs and MSCs, three-dimensional tissues were formed at 24 hours of culture. In order to track morphological changes in cells, fluorescence-labeled mouse glomeruli were cocultured with various kinds of cells (FIG. 4, panel B, FIG. 4, panel C and FIG. 4, panel D). Briefly, glomeruli isolated from mice (green), HUVECs into which Kusabira Orange had been introduced (FIG. 4, panel B, FIG. 4, panel C and FIG. 4, panel D: red) and MSCs (FIG. 4, panel B and FIG. 4, panel D: blue) were cocultured, and cell morphology was observed with a confocal microscope. It was observed that, immediately after the beginning of culture, HUVECs were found to be scattered evenly around glomeruli.

From the foregoing, it was revealed that a vascularized three-dimensional tissue was autonomously generated by coculturing the three types of cells, i.e. mouse glomeruli, HUVEC and MSC, under appropriate conditions.

2. Periodical Observation of Vascularized Glomeruli Transplantation

The vascularized glomeruli generated in Section 1 of Results above were transplanted into mice and morphological changes in tissues were tracked (FIG. 4, panel E). Vascularized glomeruli were transplanted into cranial window (CW) mice as described in Section 8 of Methods, and morphological changes were tracked as described in Section 9 of Methods.

In the mouse heads transplanted with the vascularized glomeruli, blood perfusion to all over the transplantation site occurred at day 3 post-transplantation (FIG. 4, panel E). Further, the results of live observation with a confocal microscope at day 10 post-transplantation not only revealed that the glomerular structure was retained even after transplantation; it was also found that mouse blood vessels inside glomeruli were directly anastomosed to human blood vessels (HUVECs), letting blood flow inside the glomeruli (FIG. 4, panel F). These results show that transplantation of vascularized glomeruli induced early resumption of blood flow into the glomeruli and enabled efficient engraftment.

[Example 3] Integration of Vascular Networks for Tumor Tissues

[Methods]

1. Recovery of Human Pancreatic Tumor Tissues

Human pancreatic tumor tissues removed from nesidioblastosis patients were washed with PBS under a clean bench environment, transferred to a 6 cm dish containing a HBSS medium and sliced into 1 mm-square sections, which were used in the subsequent experiments.

2. Integration of Vascular Networks for Human Pancreatic Tumor Tissues

Human pancreatic tumor tissues sliced into 1 mm-square sections were recovered with a Pipetman (20 sections) and mixed with $2 \times 10^6$ EGFP-HUVECs and $2 \times 10^5$ MSCs. The mixture was centrifuged at 950 rpm. The resultant supernatant was removed, and the cells were suspended in 1 ml of EGM medium and seeded on 24-well plate in which Matrigel was placed in advance. Then, morphological changes were tracked with a confocal microscope.

3. Recovery of Mouse Pancreatic Cancer Tissues

Pancreatic cancer tissues were recovered from pancreatic cancer model mice (Pdx1-cre; LSL-Kras$^{G12D}$; CDKN2A$^{-/-}$: purchased from NCI) which are held to be capable of recapitulating the multistep carcinogenesis of pancreatic cancer. The cancer tissues were washed with PBS and transferred to a 6 cm dish containing a HBSS medium under a clean bench environment. The recovered cancer tissues were chopped into 1 mm-square sections, which were used in the subsequent experiments.

4. Integration of Vascular Networks for Mouse Pancreatic Cancer Tissues

Pancreatic cancer tissues chopped into 1 mm-square sections were recovered with a Pipetman (20 sections) and mixed with $2\times10^6$ EGFP-HUVECs and $2\times10^5$ MSCs. The mixture was centrifuged at 950 rpm for 5 min. The resultant supernatant was removed, and the cells were suspended in 1 ml of EGM™ BulletKit™ (Lonza CC4133) medium and seeded on 24-well plate in which Matrigel was placed in advance. The plate was incubated in a 37° C. incubator for 4 days while exchanging the medium every day.

The 24-well plate was prepared as follows. Briefly, 300 µl of a solution prepared by mixing EGM medium and BD Matrigel™ basement membrane matrix (BD Japan 356234) at 1:1 was added to each well of a 24-well plate, which was then incubated in a 37° C. incubator for 10 min to solidify the gel.

[Results]
1. Vascularization of Human Pancreatic Tumor Tissues

The results of observation with a confocal microscope confirmed that by means of coculture, vascularized three-dimensional tissues were autonomously generated in about 24-48 hours while vascular networks were constituted around the human pancreatic tissues chopped into 1 mm-square sections (FIG. 5, panel A).

2. Vascularization of Mouse Pancreatic Cancer Tissues

When the pancreatic cancer tissue chopped into 1 mm-square sections was cocultured with HUVECs and MSCs on the Matrigel™ solidified in 24-well plate, vascularized three-dimensional tissues could successfully be generated (FIG. 5, panel B, upper panel). As a control experiment, 1 mm-square sections of the pancreatic cancer tissue alone were cultured on solidified Matrigel™; neither formation of three-dimensional tissues nor vascularization was confirmed and there occurred no changes worth particular mention (FIG. 5, panel B, lower panel).

At 4 days of culture, gene expressions in the vascularized three-dimensional tissues formed were analyzed by quantitative PCR. The result revealed that the expression of CD44 gene known as an important cancer stem cell marker increased to a level about 1.6 times as high as the level of expression in the monoculture group (FIG. 5, panel C).

It was therefore suggested that cancer stem cells—which were conventionally difficult to maintain in vitro—were amplified. Conventional two-dimensional culture systems were difficult to use as a system for pre-evaluating the efficacy of anticancer agents because the two-dimensional system has such an environment that the reactivity of anticancer agents differs greatly from the case where they are administered in vivo. By using the method of the present invention, it is expected to reproduce the reactivity in cancer tissues (including vascular systems) in living bodies. This is a culture technique that is potentially highly useful as a drug screening system applicable to the development of novel anticancer agents.

[Example 4] Integration of Vascular Networks for Liver Tissues

[Methods]
1. Isolation of Mouse Liver Tissues

C57BL/6-Tg mice (Japan SLC, Inc.) anesthetized with diethyl ether (Wako) were laparotomized after disinfection of the abdomen with 70% ethanol, followed by transcardial perfusion. The liver was cut out, washed with physiological saline and minced with scissors. The minced liver was filtered with a 100 µm mesh cell strainer while adding Hanks' buffer (HBSS, Gibco) containing 0.1% albumin from bovine serum (BSA, Sigma) little by little. The flow-through was filtered with a 70 µm mesh cell strainer. The cell mass retained on the 70 µm mesh cell strainer was recovered with a 0.1% BSA-containing Hanks' buffer.

2. Primary Culture of Mouse Liver Tissues

Mouse liver tissues were cultured in DMEM/F12 (Invitrogen) supplemented with 10% fetal bovine serum (ICN Lot. 7219F), 2 mmol/L L-glutamine (Gibco), 100 µg/mL penicillin/streptomycin (Gibco), 10 mmol/L nicotinamide (Sigma), 50 µmol/L 2-Mercaptoethanol, $1\times10^{-7}$ mol/L 6.5% dexamethasone (Sigma), $2.6\times10^{-4}$ M L-Ascorbic acid 2-phosphate sesquimagnesium salt hydrate (Sigma), 5 mmol/L HEPES (DOJINDO), 1 µg/mL Human recombinant insulin expressed in yeast (Wako), 50 ng/mL Human recombinant HGF expressed in Sf21 insect cells (Sigma) and 20 ng/mL Mouse Submaxillary Glands EGF (Sigma) in a 37° C., 5% $CO_2$ incubator.

3. Cell Culture

Normal human umbilical vein endothelial cells (HUVECs) (Lonza CC-2517) were cultured using a medium prepared especially for culturing HUVECs [EGM™ BulletKit™ (Lonza CC-4133)] within a guaranteed passage number (5 passages). Human mesenchymal stem cells (hMSCs) (Lonza PT-2501) were cultured using a medium prepared especially for culturing hMSCs [MSCGM™ BulletKit™ (Lonza PT3001)] within a guaranteed passage number (5 passages). Both HUVECs and hMSCs were cultured in a 37° C., 5% $CO_2$ incubator.

4. Preparation of Three-Dimensional Tissues with Vascular Networks

For chronological observation, two mouse liver tissues were left standing in each well of PrimeSurface™ 96-well U plate (Sumitomo Bakelite) preliminarily filled with a medium for liver tissues. Then, $5\times10^4$ HUVECs and $5\times10^3$ hMSCs were seeded in each well. The plate was then incubated in a 37° C. incubator for 1 day.

5. Experimental Animals

NOD/SCID mice (Sankyo Labo Service Co., Tokyo, Japan) used as transplantation animal were bred under a SPF environment with a light-dark cycle consisting of 10 hours for day and 14 hours for night. The breeding of experimental animals were entrusted to the Animal Experiment Center, Joint Research Support Section, Advanced Medical Research Center, Yokohama City University. Animal experiments were performed in accordance with the ethical guidelines stipulated by Yokohama City University.

6. Transplantation into CW Mice

The CW mice prepared in Section 8 above underwent transplantation after their brain surfaces were exposed by removing the glass of the cranial window. Those mice which did not have any sign of bleeding, inflammation or infection on their brain surfaces were used. After anesthetization, the area surrounding the cranial window was disinfected with 70% ethanol. The pointed end of an 18 G needle was inserted into the border line between the custom-made circular slide glass and Aron Alpha and so manipulated as to peel off the slide glass without damaging the brain surface. Thus, the brain surface was exposed. Subsequently, the brain surface was washed with physiological saline. A tissue transplant was left standing near the center of the brain surface, and the slide glass was remounted. To ensure no gap would be left, the space between the slide glass and the brain surface was filled with physiological saline and, thereafter, the slide glass was sealed tightly with an adhesive prepared from coatley plastic powder and Aron Alpha, in the same manner as performed at the time of preparation of CW mouse.

7. Periodical Observation with Confocal Microscope of the Tissues Transplanted into CW Mice The three-dimensional tissues transplanted into CW mice in Section 6 above were observed.

Those mice which underwent transplantation were anesthetized by ketalar/xylazine mixed anesthesia in the same manner as in Section 11 above. Each mouse was fixed on a 25×60 mm micro cover glass (Matsunami) in the supine position so that the cranial window would become level. Morphological changes of the transplanted three-dimensional tissues with vascular networks were observed with a confocal microscope (LEICA TCS-SP5).

[Results]

1. Generation of Three-Dimensional Tissues by Coculturing Mouse Liver Tissues, Vascular Endothelial Cells and Mesenchymal Stem Cells Culture was performed as described in Section 4 of Methods above. Immediately after the beginning of culture, cells were scattered around liver tissues, and no three-dimensional tissues visible with eyes were recognized. At 4 hours of culture, however, interactions between cells started, and scattered cells began to gather closely. At 8 hours of culture in an advanced stage, cells so aggregated as to cover liver tissues and gradually constituted a three-dimensional structure. Finally, at 24 hours of culture, self-organization progressed further and a vascularized three-dimensional tissue was constituted (FIG. 6, panel A, FIG. 6, panel B). On the other hand, when coculture was not performed but liver tissues alone were cultured, neither vascularization nor formation of three-dimensional tissues was recognized (FIG. 6, panel B).

Further, by culturing cells as described in Section 4 of Methods above, an attempt was made to decrease the size of vascularized three-dimensional tissues in a culture plate (substrate?) of such a shape that cells/tissues would gather in the bottom (FIG. 6, panel A). When mouse liver tissues were cocultured with HUVECs and MSCs, three-dimensional tissues were formed at 24 hours of culture. In order to track morphological changes in cells, coculture experiments were performed using fluorescence-labeled mouse liver tissues and various kinds of cells (FIG. 6, panel A: red; FIG. 6, panel B, FIG. 6, panel D: green), HUVECs into which green fluorescent protein (GFP) had been introduced (FIG. 6, panel B) and MSCs were cocultured, followed by observation of cell morphology under a confocal microscope. Immediately after the beginning of culture, HUVECs were confirmed to be scattered evenly around liver tissues.

From the foregoing, it was revealed that a vascularized three-dimensional tissue was autonomously generated by coculturing the three types of cells, i.e., mouse liver tissue, HUVEC and MSC, under appropriate conditions.

2. Periodical Observation of Vascularized Liver Tissue Transplantation

The vascularized liver tissues generated in Section 1 of Results above were transplanted into mice, and morphological changes in tissues were tracked (FIG. 6, panel C). Transplantation into CW mice was performed as described in Section 6 of Methods, and morphological changes were tracked as described in Section 7 of Methods.

In the heads of mice transplanted with vascularized liver tissues, blood perfusion to all over the transplantation site occurred at day 3 post-transplantation (FIG. 6, panel C). Further, when observed with a confocal microscope, blood perfusion into the inside of transplanted liver tissues was confirmed (FIG. 6, panel D).

It was shown by these results that transplantation of vascularized liver tissues induced early resumption of blood flow into the inside of transplanted liver tissues.

[Example 5] Integration of Vascular Networks for Intestinal Tissues

[Methods]

1. Isolation of Mouse Intestinal Tissues

C57BL/6-Tg mice (Japan SLC, Inc.) anesthetized with diethyl ether (Wako) were laparotomized after disinfection of the abdomen with 70% ethanol. The inlet of the small intestine was cut off by a length of about 20 cm. The lumen of the small intestine thus cut off was washed with 50 ml of physiological saline and then cut lengthwise to expose the mucosa which was cut into small sections of about 5 cm. Subsequently, the resultant small sections were treated in PBS containing 2 mM Ethylenediaminetetraacetic acid (EDTA; Dojinkagaku) and 0.5 mM Dithiothreitol (DTT; Sigma Chemical Company) at 37° C. for 20 min. The resultant supernatant was passed through a 100 μm mesh cell strainer and washed with PBS three times. Finally, the flow-through was filtered with a 40 μm mesh cell strainer. The cell mass retained on the 40 μm mesh cell strainer was recovered with a 0.1% BSA-containing Hanks' buffer.

3. Primary Culture of Mouse Intestinal Tissues

Mouse intestinal tissues were cultured using RPMI1640 (Wako) supplemented with 20% fetal bovine serum (BWT Lot. S-1560), 100 μg/ml penicillin/streptomycin (Gibco) and Insulin-Transferrin-SeleniumX (Gibco) in a 37° C., 5% $CO_2$ incubator.

4. Cell Culture

Normal human umbilical vein endothelial cells (HUVECs) (Lonza CC-2517) were cultured using a medium prepared especially for culturing HUVECs [EGM™ BulletKit™ (Lonza CC-4133)] within a guaranteed passage number (5 passages). Human mesenchymal stem cells (hMSCs) (Lonza PT-2501) were cultured using a medium prepared especially for culturing hMSCs [MSCGM™ BulletKit™ (Lonza PT3001)] within a guaranteed passage number (5 passages). Both HUVECs and hMSCs were cultured in a 37° C., 5% $CO_2$ incubator.

5. Preparation of Three-Dimensional Tissues with Vascular Networks

For chronological observation, 20 mouse intestinal tissues were left standing in each well of PrimeSurface™ 96-well U plate (Sumitomo Bakelite) preliminarily filled with a medium for intestinal tissues. Then, $5\times10^4$ HUVECs and $5\times10^3$ hMSCs were seeded in each well. The plate was then incubated in a 37° C. incubator for 1 day. 6. Chronological Observation of Cell Coculture with Stereomicroscope Coculture was performed for tracking chronological changes with a stereomicroscope. Briefly, mouse intestinal tissues were left standing in each well of a 24-well plate, and $2\times10^6$ HUVECs and $2\times10^5$ hMSCs were seeded in each well. After seeding, the plate was set in a stereomicroscope (Leica DFC300FX) and morphological changes caused by coculture were observed.

7. Experimental Animals

NOD/SCID mice (Sankyo Labo Service Co., Tokyo, Japan) used as transplantation animal were bred under a SPF environment with a light-dark cycle consisting of 10 hours for day and 14 hours for night. The breeding of experimental animals were entrusted to the Animal Experiment Center, Joint Research Support Section, Advanced Medical Research Center, Yokohama City University. Animal experiments were performed in accordance with the ethical guidelines stipulated by Yokohama City University.

8. Transplantation into CW Mice

The CW mice prepared underwent transplantation after their brain surfaces were exposed by removing the glass of the cranial window. Those mice which did not have any sign of bleeding, inflammation or infection on their brain surfaces were used. After anesthetization, the area surrounding the cranial window was disinfected with 70% ethanol. The pointed end of an 18 G needle was inserted into the border between the custom-made circular slide glass and Aron Alpha and so manipulated as to peel off the slide glass without damaging the brain surface. Thus, the brain surface was exposed. Subsequently, the brain surface was washed with physiological saline. A transplant was left standing near the center of the brain surface, and the custom-made slide glass was remounted. To ensure no gap would be left, the space between the slide glass and the brain surface was filled with physiological saline and, thereafter, the slide glass was sealed tightly with an adhesive prepared from coatley plastic powder and Aron Alpha, in the same manner as performed at the time of preparation of CW mice.

9. Periodical Observation with Confocal Microscope of the Tissues Transplanted into CW Mice The three-dimensional tissues transplanted into CW mice in the preceding Section 8 were observed.

Those mice which underwent transplantation were anesthetized by ketalar/xylazine mixed anesthesia in the same manner as in Section 11 above. Each mouse was fixed on a 25×60 mm micro cover glass (Matsunami) in the supine position so that the cranial window would become level. Morphological changes of the transplanted three-dimensional tissues with vascular networks were observed with a confocal microscope (LEICA TCS-SP5).

[Results]

Figure 7:
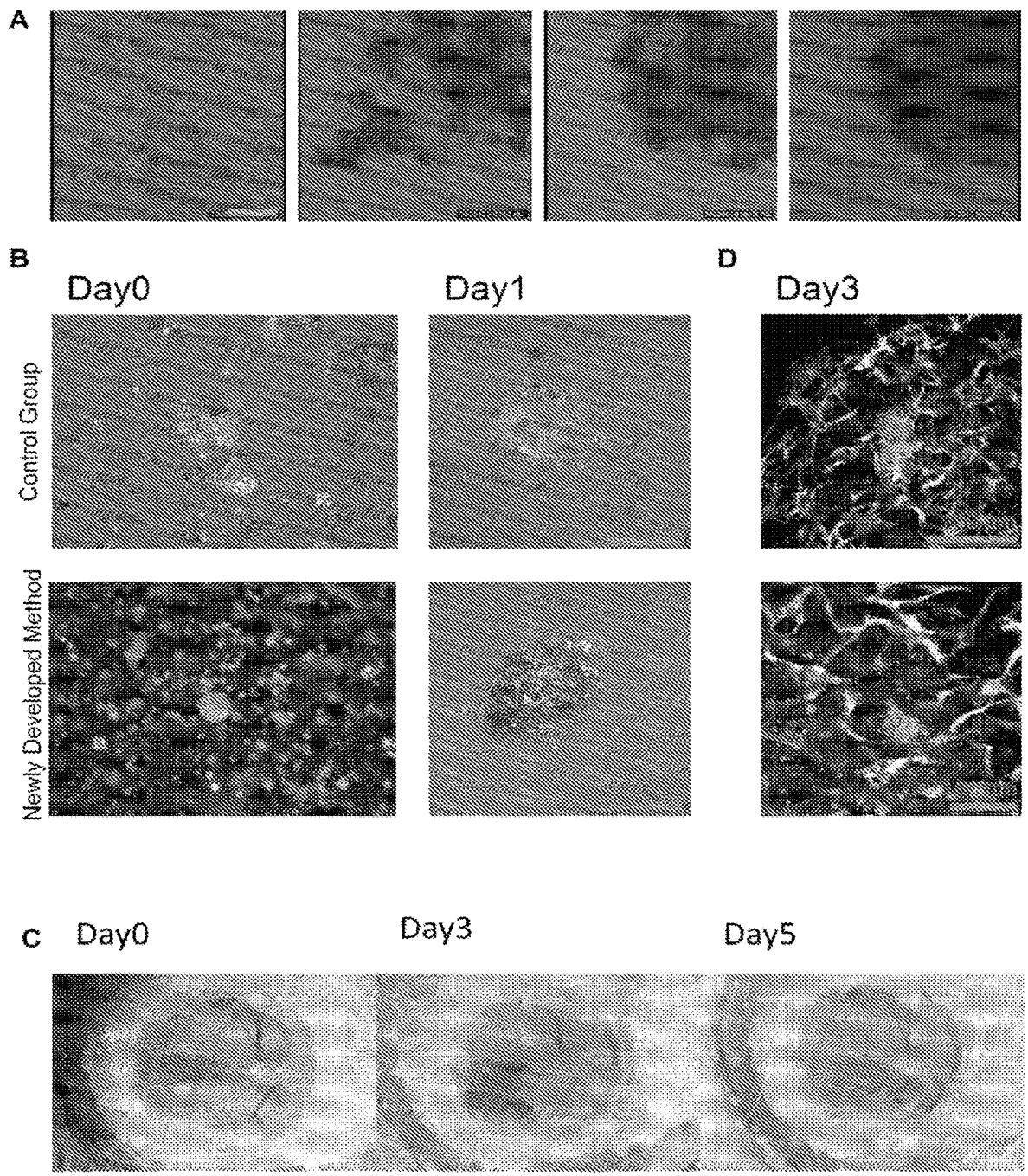
FIG. 7 This figure shows the integration of vascular networks to intestinal tissues.
A) Time-lapse imaging of the process of formation of a three-dimensional tissue using mouse intestinal tissues (red), vascular endothelial cells (green) and mesenchymal stem cells (colorless).
B) Autonomous formation of a three-dimensional tissue derived from intestinal tissues (red), vascular endothelial cells (green) and mesenchymal stem cells (colorless) using a culture plate (substrate?) of such a shape that cells gather in the bottom.
C) Macroimaging of the site of transplantation of vascularized intestinal tissues.
D) In vivo live imaging of the site of transplantation of vascularized intestinal tissues (mouse intestinal tissues (red), vascular endothelial cells (green) and mesenchymal stem cells (colorless)).

1. Generation of Vascularized Three-Dimensional Tissues by Coculture of Mouse Intestinal Tissues, Vascular Endothelial Cells and Mesenchymal Stem Cells Culture was performed as described in Section 4 of Methods above. Immediately after the beginning of culture, cells were scattered around intestinal tissues, and no three-dimensional tissues visible with eyes were recognized. At 4 hours of culture, however, interactions between cells started, and scattered cells began to gather closely. At 8 hours of culture in an advanced stage, cells so aggregated as to cover intestinal tissues and gradually constituted a three-dimensional structure. Finally, at 24 hours of culture, self-organization progressed further and a vascularized three-dimensional tissue was constituted (FIG. 7, panel A, FIG. 7, panel B). On the other hand, when coculture was not performed but intestinal tissues alone were cultured, neither vascularization nor formation of three-dimensional tissues was recognized (FIG. 7, panel B).

Further, by culturing as described in Section 4 of Methods above, an attempt was made to decrease the size of vascularized three-dimensional tissues in a culture plate (substrate?) of such a shape that cells/tissues would gather in the bottom (FIG. 7, panel B). When mouse intestinal tissues were cocultured with HUVECs and MSCs, three-dimensional tissues were formed at 24 hours of culture. In order to track morphological changes in cells, fluorescence-labeled mouse intestinal tissues were cocultured with various kinds of cells (FIG. 7, panel B). Briefly, intestinal tissues isolated from mice (FIG. 7, panel B: red), HUVECs into which green fluorescent protein (GFP) had been introduced (FIG. 7, panel B) and MSCs were cocultured, and cell morphology was observed with a confocal microscope. Immediately after the beginning of culture, HUVECs were confirmed to be scattered evenly around intestinal tissues.

From the foregoing, it was revealed that a vascularized three-dimensional tissue was autonomously generated by coculturing the three types of cells, i.e., mouse intestinal tissue, HUVEC and MSC, under appropriate conditions.

2. Periodical Observation of Vascularized Intestinal Tissue Transplantation

The vascularized intestinal tissues generated in Section 1 of Results above were transplanted into mice and morphological changes in tissue were tracked (FIG. 7, panel C). Vascularized intestinal tissues were transplanted into cranial window (CW) mice as described in Section 6 of Methods, and morphological changes were tracked as described in Section 7 of Methods.

In the mouse heads transplanted with vascularized intestinal tissues, blood perfusion to all over the transplantation site occurred at day 3 post-transplantation (FIG. 7, panel C). Further, observation with a confocal microscope confirmed that blood perfusion into the inside of the transplanted intestinal tissues occurred at day 3 post-transplantation. (FIG. 7, panel D).

It was shown by these results that transplantation of vascularized intestinal tissues induced early resumption of blood flow into the inside of the transplanted intestinal tissues.

[Example 6] Integration of Vascular Networks for Pulmonary Tissues

[Methods]

1. Isolation of Mouse Pulmonary Tissues

C57BL/6-Tg mice (Japan SLC, Inc.) anesthetized with diethyl ether (Wako) were laparotomized after disinfection of the abdomen with 70% ethanol, and the lungs were cut out. The lungs were washed with physiological saline and minced with scissors. The minced lung was filtered with a 100 μm mesh cell strainer while adding Hanks' buffer (HBSS, Gibco) containing 0.1% albumin from bovine serum (BSA, Sigma) little by little. The flow-through was filtered with a 40 μm mesh cell strainer. The cell mass retained on the 40 μm mesh cell strainer was recovered with a 0.1% BSA-containing Hanks' buffer.

2. Cell Culture

Normal human umbilical vein endothelial cells (HUVECs) (Lonza CC-2517) were cultured using a medium prepared especially for culturing HUVECs [EGM™ BulletKit™ (Lonza CC-4133)] within a guaranteed passage number (5 passages). Human mesenchymal stem cells (hMSCs) (Lonza PT-2501) were cultured using a medium prepared especially for culturing hMSCs [MSCGM™ BulletKit™ (Lonza PT3001)] within a guaranteed passage number (5 passages). Both HUVECs and hMSCs were cultured in a 37° C., 5% $CO_2$ incubator.

3. Preparation of Three-Dimensional Tissues with Vascular Networks

For chronological observation, 20 mouse pulmonary tissues were left standing in each well of PrimeSurface™ 96-well U plate (Sumitomo Bakelite) filled with a medium for pulmonary tissues. Then, $5 \times 10^4$ HUVECs and $5 \times 10^3$ hMSCs were seeded in each well. The plate was then incubated in a 37° C. incubator for 1 day. Further, mouse pulmonary tissues were left standing in each well of a 24-well plate. Then, $2 \times 10^6$ HUVECs and $2 \times 10^5$ hMSCs were seeded in each well.

4. Chronological Observation of Cell Coculture with Stereomicroscope

Coculture was performed for tracking chronological changes with a stereomicroscope. Briefly, 20 mouse pulmonary tissues were left standing in each well of a 24-well plate. HUVECs ($2\times10^6$ cells) and hMSCs ($2\times10^5$ cells) were seeded in each well. After seeding, the plate was set in a stereomicroscope (Leica DFC300FX) and morphological changes caused by coculture were observed.

5. Experimental Animals

NOD/SCID mice (Sankyo Labo Service Co., Tokyo, Japan) used as transplantation animal were bred under a SPF environment with a light-dark cycle consisting of 10 hours for day and 14 hours for night. The breeding of experimental animals were entrusted to the Animal Experiment Center, Joint Research Support Section, Advanced Medical Research Center, Yokohama City University. Animal experiments were performed in accordance with the ethical guidelines stipulated by Yokohama City University.

6. Transplantation into CW Mice

The CW mice prepared in Section 8 underwent transplantation after their brain surfaces were exposed by removing the glass of the cranial window. Those mice which did not have any sign of bleeding, inflammation or infection on their brain surfaces were used. After anesthetization, the area surrounding the cranial window was disinfected with 70% ethanol. The pointed end of an 18 G needle was inserted into the border line between the custom-made circular slide glass and Aron Alpha and so manipulated as to peel off the slide glass without damaging the brain surface. Thus, the brain surface was exposed. Subsequently, the brain surface was washed with physiological saline. A tissue transplant was left standing near the center of the brain surface, and the slide glass was remounted. To ensure no gap would be left, the space between the slide glass and the brain surface was filled with physiological saline and, thereafter, the slide glass was sealed tightly with an adhesive prepared from coatley plastic powder and Aron Alpha, in the same manner as performed at the time of preparation of CW mouse.

7. Periodical observation with Confocal Microscope of the Tissues Transplanted into CW Mice The three-dimensional tissues transplanted into CW mice in Section 9 were observed.

Those mice which underwent transplantation were anesthetized by ketalar/xylazine mixed anesthesia in the same manner as in Section 11 above. Each mouse was fixed on a 25×60 mm micro cover glass (Matsunami) in the supine position so that the cranial window would become level. Morphological changes of the transplanted three-dimensional tissues with vascular networks were observed with a confocal microscope (LEICA TCS-SP5).

[Results]

Figure 8:
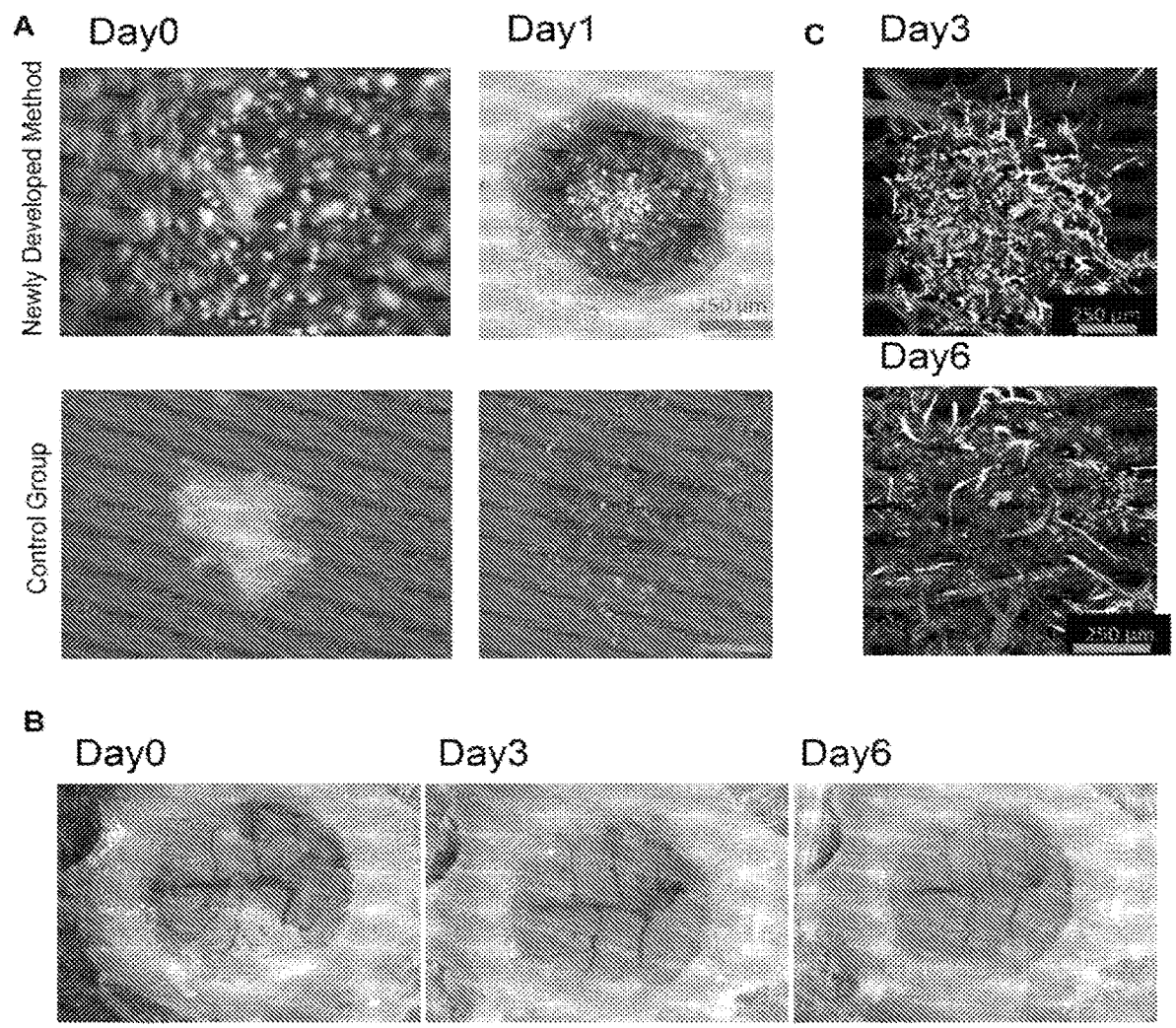
FIG. 8 This figure shows the integration of vascular networks to pulmonary tissues.
A) Autonomous formation of a three-dimensional tissue using mouse pulmonary tissues (red), vascular endothelial cells (green) and mesenchymal stem cells (colorless).
B) Macroimaging of the site of transplantation of vascularized pulmonary tissue.
C) In vivo live imaging of the site of transplantation of vascularized pulmonary tissue (mouse pulmonary tissues (red), vascular endothelial cells (green), mesenchymal stem cells (colorless) and mouse CD31 (blue)).

1. Generation of Three-Dimensional Tissues by Coculturing Mouse Pulmonary Tissues, Vascular Endothelial Cells and Mesenchymal Stem Cells Culture was performed as described in Section 6 of Methods above. Immediately after the beginning of culture, cells were scattered around pulmonary tissues, and no three-dimensional tissues visible with eyes were recognized. At 4 hours of culture, however, interactions between cells started, and scattered cells began to gather closely. At 8 hours of culture in an advanced stage, cells so aggregated as to cover pulmonary tissues and gradually constituted a three-dimensional structure. Finally, at 24 hours of culture, self-organization progressed further and a vascularized three-dimensional tissue was constituted (FIG. 8, panel A). On the other hand, when coculture was not performed but pulmonary tissues alone were cultured, neither vascularization nor formation of three-dimensional tissues was recognized (FIG. 8, panel A).

Further, by culturing cells as described in Section 4 of Methods above, an attempt was made to decrease the size of vascularized three-dimensional tissues in a culture plate (substrate?) of such a shape that cells/tissues would gather in the bottom (FIG. 2A, FIG. 2B, FIG. 2C, FIG. 2D, FIG. 2E). When mouse pulmonary tissues were cocultured with HUVEC and MSC, three-dimensional tissues were formed at 24 hours of culture. In order to track morphological changes in cells, coculture experiments were performed using fluorescence-labeled mouse pulmonary tissues and various kinds of cells (FIG. 8, panel A). Briefly, pulmonary tissues isolated from mice (FIG. 8, panel A: red), HUVECs into which green fluorescent protein (GFP) had been introduced (FIG. 8, panel A: green) and MSC were cocultured, followed by observation of cell morphology under a confocal microscope. Immediately after the beginning of culture, HUVECs were confirmed to be scattered evenly around pulmonary tissues.

From the foregoing, it was revealed that a vascularized three-dimensional tissue was autonomously generated by coculturing the three types of cells, i.e., mouse pulmonary tissue, HUVEC and MSC, under appropriate conditions.

2. Periodical Observation of Vascularized Pulmonary Tissue Transplantation

The vascularized pulmonary tissues generated in Section 1 of Results above were transplanted into mice, and morphological changes in tissues were tracked (FIG. 8, panel B). Transplantation into CW mice was performed as described in Section 16 of Methods, and morphological changes were tracked as described in Section 7 of Methods.

In the heads of mice transplanted with vascularized pulmonary tissues, blood perfusion to all over the transplantation site occurred at day 3 post-transplantation (FIG. 8, panel B). Further, when observed with a confocal microscope, blood perfusion into the inside of transplanted liver tissues was confirmed at day 7 post-transplantation (FIG. 8, panel C).

It was shown by these results that transplantation of vascularized pulmonary tissues induced early resumption of blood flow into the inside of transplanted pulmonary tissues.

[Example 7] Integration of Vascular Networks for iPS Cell-Derived Endodermal Tissues

[Methods and Results]

1. Directed Differentiation of iPS Cells

Expanded but undifferentiated iPS cells (kindly provided by Dr. Nakauchi, Tokyo University; TkDA3 clone; established from dermal fibroblasts) were washed once with a washing medium (DMEM/F12; Life Technologies 11320). A cultured cell dissociating solution (Funakoshi AT104) was added to 100 mm dishes in an amount of 1 ml per dish. Cells were recovered into 50 ml centrifugal tubes and subjected to centrifugation at 900 rpm for 5 min. After taking a cell count, cells were seeded on Matrigel™-coated 60 mm dishes at a density of $1.5\times10^6$ cells per dish. Matrigel™-coating was performed as follows. Briefly, BD Matrigel™ basement membrane matrix (BD Japan 356231) was diluted 30-fold with DMEM (Life Technologies 1196118). The thus diluted gel was added to 60 mm dishes (2 ml/dish), which were left standing at room temperature for 2 hr. As a culture broth, an iPS culture medium supplemented with ROCK inhibitor Y-27632 (Calbiochem 688000) was used. Cells were incubated in a 37° C. incubator for 24 hr to induce cell adhesion.

Subsequently, the culture broth was exchanged with a directed differentiation medium. This medium was RPMI-1640 (Wako Pure Chemicals 189-02025) supplemented with B-27™ Supplement Minus Insulin (Life Technologies 0050129SA) (1/100 dilution) and 100 ng/μl Activin A (Ajinomoto). While exchanging the medium every 2 days, cells were cultured for 6 days to allow directed differentiation into definitive endoderms. The degree of differentiation into endodermal lineage was confirmed by quantitative PCR and immunostaining.

2. Preparation of iPS Cell-Derived Endodermal Tissues

Human iPS cells which had undergone directed differentiation into definitive endoderms were seeded in each well of EZSPHERE™ (Asahi Glass 4810-900 6-well-Flat bottom) at a density of $1.0 \times 10^6$ cells/well. As a culture broth, a 1:1 mixture of a medium kit for sole use with hepatocytes (HCM™ BulletKit™; Lonza CC3198) and EGM™ BulletKit™ (Lonza CC-4133) was used. Cells were cultured in a 37° C. incubator for 8 days, with half of the medium exchanged every 2 days, to thereby prepare steric endodermal tissues of 50-500 μm in diameter.

3. Preparation of Three-Dimensional Tissues with Human Vasculatures Using 96-Well U Plate One to twenty iPS cell-derived endodermal tissues were left standing in each well of PrimeSurface™ 96-Well U Plate (Sumitomo Bakelite) preliminarily filled with the medium for culturing iPS cell-derived endodermal tissues described in Section 2 above. Then, $1.0 \times 10^4$ HUVECs and $1.0 \times 10^3$ hMSCs were seeded in each well. Subsequently, the cells were incubated in a 37° C. incubator for 4 days.

As a result, it became clear that endodermal tissues, when cocultured with human vascular endothelial cells and mesenchymal stem cells, autonomously induced a three-dimensional tissue (FIG. 9, panel B). It was also found that in the thus induced tissue, human vascular endothelial cells formed lumen-like structures to form a vascularized tissue (FIG. 9, panel C). Since the formation of such a three-dimensional tissue was never confirmed in the monoculture group of iPS cell-derived endodermal tissues, it was demonstrated that use of the method of the present invention is essential for preparing vascularized tissues (FIG. 9, panel B).

All publications, patents and patent applications cited herein are incorporated herein by reference in their entirety.

INDUSTRIAL APPLICABILITY

Biological tissues integrated with a vascular system according to the present invention are applicable to generation of human functional cells, organ transplantation, drug discovery screening, new analytical systems for evaluating such factors as the relationship between development of drug efficacy and blood vessels.

The invention claimed is:

1. A method of preparing a vascularized tissue in vitro, the method comprising
    coculturing a biological tissue with vascular cells and mesenchymal cells,
    wherein a cell count ratio of the vascular cell to mesenchymal cell is 10-3:1.

2. The method according to claim 1, wherein the biological tissue is cocultured with the vascular cells and the mesenchymal cells on a U-shaped plate.

3. The method according to claim 1, wherein the biological tissue is a pancreatic tissue.

4. The method according to claim 1, wherein the biological tissue is a cancer tissue isolated from an individual.

5. The method according to claim 4, wherein the cancer tissue is a tissue derived from a pancreas, kidney, liver, intestine or lung.

6. The method according to claim 4, wherein the cancer tissue is a tissue derived from a pancreatic islet tissue or renal glomeruli.

7. The method according to claim 1, wherein the biological tissue is a pancreas, kidney, liver, intestine or lung tissue isolated from an individual.

8. The method according to claim 1, wherein the biological tissue is a pancreatic islet tissue or renal glomeruli tissue.

9. The method according to claim 1, wherein the biological tissue is a tissue induced from pluripotent stem cells, or tissue stem/progenitor cells.

10. The method according to claim 9, wherein the tissue induced from pluripotent stem cells is a tissue induced from iPS cells.

11. The method according to claim 9, wherein the tissue induced from pluripotent stem cells is an iPS cell-derived endodermal tissue.

12. The method according to claim 1, wherein the biological tissue is a tissue induced from differentiated cells.

* * * * *